United States Patent
Moussy et al.

(10) Patent No.: US 10,202,370 B2
(45) Date of Patent: Feb. 12, 2019

(54) BENZIMIDAZOLE DERIVATIVES AS SELECTIVE PROTEINE KINASE INHIBITORS

(71) Applicant: AB SCIENCE, Paris (FR)

(72) Inventors: Alain Moussy, Paris (FR); Abdellah Benjahad, Champigny sur Marne (FR); Claire Schalon, Gif-sur-Yvette (FR); Didier Pez, Nievroz (FR); Emmanuel Chevenier, Les Ulis (FR); Franck Sandrinelli, Balan (FR); Jason Martin, L'Hay-les-Roses (FR); Willy Picoul, Lyons (FR)

(73) Assignee: AB SCIENCE, Paris (FR)

( * ) Notice: Subject to any disclaimer, the term of this patent is extended or adjusted under 35 U.S.C. 154(b) by 197 days.

(21) Appl. No.: 14/900,008

(22) PCT Filed: Jun. 20, 2014

(86) PCT No.: PCT/EP2014/063045
§ 371 (c)(1),
(2) Date: Dec. 18, 2015

(87) PCT Pub. No.: WO2014/202763
PCT Pub. Date: Dec. 24, 2014

(65) Prior Publication Data
US 2016/0152608 A1    Jun. 2, 2016

(30) Foreign Application Priority Data
Jun. 20, 2013   (EP) ...................... 13305837

(51) Int. Cl.
| | |
|---|---|
| *C07D 417/14* | (2006.01) |
| *A61K 8/49* | (2006.01) |
| *A61K 31/427* | (2006.01) |
| *A61K 31/4439* | (2006.01) |
| *A61K 31/506* | (2006.01) |
| *A61K 31/5377* | (2006.01) |
| *A61K 45/06* | (2006.01) |
| *A61Q 19/00* | (2006.01) |
| *C07D 401/14* | (2006.01) |
| *C07D 413/14* | (2006.01) |
| *C07D 417/12* | (2006.01) |

(52) U.S. Cl.
CPC ............. *C07D 417/14* (2013.01); *A61K 8/49* (2013.01); *A61K 31/427* (2013.01); *A61K 31/4439* (2013.01); *A61K 31/506* (2013.01); *A61K 31/5377* (2013.01); *A61K 45/06* (2013.01); *A61Q 19/00* (2013.01); *C07D 401/14* (2013.01); *C07D 413/14* (2013.01); *C07D 417/12* (2013.01)

(58) Field of Classification Search
None
See application file for complete search history.

(56) References Cited

FOREIGN PATENT DOCUMENTS

| | | |
|---|---|---|
| EP | 0820990 A2 | 1/1998 |
| EP | 1878733 A1 | 1/2008 |
| EP | 2226315 A1 | 9/2010 |
| WO | 9703069 A1 | 1/1997 |
| WO | 9719065 A1 | 5/1997 |
| WO | 9802438 A1 | 1/1998 |
| WO | 9811095 A1 | 3/1998 |
| WO | 9924440 A1 | 5/1999 |
| WO | WO-0062778 A1 * 10/2000 ........... C07C 237/40 |
| WO | 2004014903 A1 | 2/2004 |
| WO | 2004087699 A2 | 10/2004 |
| WO | 2005021537 A1 | 3/2005 |
| WO | 2006073610 A2 | 7/2006 |
| WO | 2006086539 A1 | 8/2006 |
| WO | 2007076092 A2 | 7/2007 |
| WO | 2007081630 A2 | 7/2007 |
| WO | 2008083367 A2 | 7/2008 |

(Continued)

OTHER PUBLICATIONS

Cockerill et al., Bioorganic & Medicinal Chemistry Letters, vol. 11, No. 11, Jan. 2001, pp. 1401-1405.

(Continued)

*Primary Examiner* — Kortney L. Klinkel
*Assistant Examiner* — Tori Strong
(74) *Attorney, Agent, or Firm* — Young & Thompson

(57) ABSTRACT

Disclosed are compounds of formula I or pharmaceutically acceptable salts thereof:

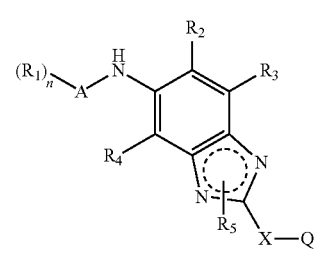

Wherein n, $R_1$, $R_2$, $R_3$, $R_4$, $R_5$, A, Q and X are as defined in the description. These compounds selectively modulate, regulate, and/or inhibit signal transduction mediated by certain native and/or mutant protein kinases implicated in a variety of human and animal diseases such as cell proliferative, metabolic, allergic, and degenerative disorders. More particularly, these compounds are potent and selective native and/or mutant c-kit inhibitors.

8 Claims, No Drawings

(56) References Cited

FOREIGN PATENT DOCUMENTS

| WO | 2009063240 A1 | 5/2009 |
| WO | 2009134750 A1 | 11/2009 |
| WO | 2010027500 A1 | 3/2010 |
| WO | 2010070022 A1 | 6/2010 |
| WO | 2010106333 A1 | 9/2010 |
| WO | 2010138578 A1 | 12/2010 |
| WO | 2011144742 A1 | 11/2011 |
| WO | 2012044090 A2 | 4/2012 |
| WO | 2012101013 A1 | 8/2012 |
| WO | 2012127032 A1 | 9/2012 |
| WO | 2012143144 A1 | 10/2012 |

OTHER PUBLICATIONS

Gaba, M. et al., European Journal of Medicinal Chemistry, vol. 45, No. 6, Jun. 2010, pp. 2245-2249.
Lopez-Alvarodo, P. et al., The Journal of Organic Chemistry, vol. 60, No. 17, Jan. 1995, pp. 5678-5682.
Syed Abuzard et al., Indian Journal of Chemistry B, vol. 19B, No. 1, Jul. 1980, pp. 599-600.
Philip A. Harris et al., Journal of Medicinal Chemistry, vol. 51, No. 15, Aug. 2008, pp. 4632-4640.
Shiro Takahashi et al., Chemical & Pharmaceutical Bulletin, vol. 14, No. 11, Jan. 1966, pp. 1219-1227.

\* cited by examiner

BENZIMIDAZOLE DERIVATIVES AS SELECTIVE PROTEINE KINASE INHIBITORS

The present invention is directed to compounds of formula I or pharmaceutically acceptable salts thereof that selectively modulate, regulate, and/or inhibit signal transduction mediated by certain native and/or mutant protein kinases implicated in a variety of human and animal diseases such as cell proliferative, metabolic, allergic, and degenerative disorders. More particularly, these compounds are potent and selective native and/or mutant c-kit inhibitors.

BACKGROUND OF THE INVENTION

Protein Kinases are receptor type or non-receptor type proteins, which transfer the terminal phosphate of ATP to aminoacid residues, such as tyrosine, threonine, serine residues, of proteins, thereby activating or inactivating signal transduction pathways. These proteins are known to be involved in many cellular mechanisms, which in case of disruption, lead to disorders such as abnormal cell proliferation and migration as well as inflammation.

As of today, there are over 500 known Protein kinases. Included are the well-known Abl, Akt1, Akt2, Akt3, ALK, Alk5, A-Raf, Axl, B-Raf, Brk, Btk, Cdk2, Cdk4, Cdk5, Cdk6, CHK1, c-Raf-1, Csk, EGFR, EphA1, EphA2, EphB2, EphB4, Erk2, Fak, Fes, Fer, FGFR1, FGFR2, FGFR3, FGFR4, Flt-3, Fms, Frk, Fyn, Gsk3α, Gsk3β, HCK, Her2/Erbb2, Her4/Erbb4, IGF1R, IKK beta, Irak4, Itk, Jak1, Jak2, Jak3, Jnk1, Jnk2, Jnk3, KDR, Kit, Lck, Lyn, MAP2K1, MAP2K2, MAP4K4, MAPKAPK2, Met, Mer, MNK1, MLK1, mTOR, p38, PDGFRα, PDGFRβ, PDPK1, PI3Kα, PI3Kβ, PI3Kγ, PI3Kδ, Pim1, Pim2, Pim3, PKC alpha, PKC beta, PKC theta, Plk1, Pyk2, Ret, ROCK1, ROCK2, RON, Src, Stk6, Syk, TEC, Tie2, TrkA, TrkB, Tyk2, VEGFR1/Flt-1, VEGFR2/Kdr, VEGFR3/Flt-4, Yes, and Zap70.

Abnormal cellular responses triggered by protein kinase-mediated events produce a variety of diseases. These include autoimmune diseases, inflammatory diseases, neurological and neurodegenerative diseases, cancers, cardiovascular diseases, allergies and asthma, Alzheimer's disease and hormone-related diseases.

Tyrosine kinases are receptor type or non-receptor type proteins, which transfer the terminal phosphate of ATP to tyrosine residues of proteins thereby activating or inactivating signal transduction pathways. These proteins are known to be involved in many cellular mechanisms, which in case of disruption, lead to disorders such as abnormal cell proliferation and migration as well as inflammation.

As of today, there are about 58 known receptor tyrosine kinases. Included are the well-known VEGF receptors (Kim et al., Nature 362, pp. 841-844, 1993), PDGF receptors, c-kit, Flt-3 and the FLK family. These receptors can transmit signals to other tyrosine kinases including Src, Raf, Frk, Btk, Csk, Abl, Fes/Fps, Fak, Jak, Ack, etc.

Among tyrosine kinase receptors, c-kit is of special interest. Indeed, c-kit is a key receptor activating mast cells, which have proved to be directly or indirectly implicated in numerous pathologies for which the Applicant filed WO 03/004007, WO 03/004006, WO 03/003006, WO 03/003004, WO 03/002114, WO 03/002109, WO 03/002108, WO 03/002107, WO 03/002106, WO 03/002105, WO 03/039550, WO 03/035050, WO 03/035049, U.S. 60/359,652, U.S. 60/359,651 and U.S. 60/449,861, WO 04/080462, WO 05/039586, WO 06/135721, WO 07/089069, WO 07/124369, WO 08/137794, WO 08/063888, WO 08/011080, WO 09/109071, WO 10/096395, WO 13/014170.

It was found that mast cells present in tissues of patients are implicated in or contribute to the genesis of diseases such as autoimmune diseases (rheumatoid arthritis, inflammatory bowel diseases (IBD)), allergic diseases, bone loss, cancers such as solid tumors, leukaemia and GIST, tumor angiogenesis, inflammatory diseases, interstitial cystitis, mastocytosis, graft-versus-host diseases, infection diseases, metabolic disorders, fibrosis, diabetes and CNS diseases. In these diseases, it has been shown that mast cells participate in the destruction of tissues by releasing a cocktail of different proteases and mediators such as histamine, neutral proteases, lipid-derived mediators (prostaglandins, thromboxanes and leukotrienes), and various cytokines (IL-1, IL-2, IL-3, IL-4, IL-5, IL-6, IL-8, TNF-α, GM-CSF, MIP-1a, MIP-1b, MIP-2 and IFN-γ).

The c-kit receptor also can be constitutively activated by mutations leading to abnormal cell proliferation and development of diseases such as mastocytosis (D816V mutation) and various cancers such as GIST (c-kitΔ27, a juxtamembrane deletion).

Sixty to 70% of patients presenting with AML have blasts which express c-kit, the receptor for stem cell factor (SCF) (Broudy, 1997). SCF promotes growth of hematopoietic progenitors, and acts as a survival factor for AML blasts. In some cases (1 to 2%) of AML, a mutation in a conserved residue of the kinase domain (Kit816) resulting in constitutive activation of c-kit has been described (Beghini et al., 2000; Longley et al., 2001). This gain of function mutation (Asp to Val/Tyr substitution) has been identified in mast cell leukemic cell lines and in samples derived from patients with mastocytosis (Longley et al., 1996). Preliminary results show that this mutation is expressed in most cases of systemic mastocytosis ([~60%], P Dubreuil, AFIRMM, study in progress on about 300 patients).

Goal of the Invention

The main objective underlying the present invention is therefore to find potent and selective compounds capable of inhibiting wild type and/or mutated protein kinases, in particular wild type and/or mutated tyrosine kinases, and more particularly wild type and/or mutated c-kit.

The invention aims to find a class of compounds as good candidates for use as active ingredients in a medicament, more particularly for the treatment of autoimmunes diseases, inflammatory diseases, neurological diseases cancers, and diseases implicating wild type and/or mutated c-Kit over-activation.

In connection with the present invention, we have discovered that compounds of formula I are potent and selective inhibitors of certain protein kinases such as wild type and/or mutated c-kit. These compounds are good candidates for treating diseases such as autoimmunes diseases, inflammatory diseases, neurological diseases, cancers and diseases implicating wild type and/or mutated c-Kit over-activation.

DESCRIPTION OF THE INVENTION

Compounds of the present invention were screened for their ability to inhibit a protein kinase and in particular a tyrosine kinase, and more particularly c-Kit and/or mutant c-Kit.

In a first embodiment, the invention is directed to compounds of formula I, which may represent either free base forms of the substances, tautomers or pharmaceutically acceptable salts, or solvate thereof:

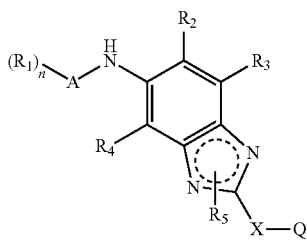

Wherein
- A is an aryl group or an heteroaryl group;
- n is 1, 2, 3, 4 or 5;
- each $R_1$, independently, is a hydrogen, a halogen, a $NH_2$, an OH, a CN, an alkyl group or an aryl group or a heteroaryl group, wherein the alkyl group, aryl group and heteroaryl group are unsubstituted or substituted by one or more substituents selected from a halogen, a linear or branched $C_1$-$C_6$ alkyl group, a $C_1$-$C_4$ alkoxy group, a $C_1$-$C_4$ haloalkyl group, a $C_1$-$C_4$ hydroxyalkyl group, a $C_3$-$C_7$ cycloalkyl group, an aryl group, aheteroaryl group, a heterocycloalkyl group, a hydroxyl, a thioalkyl, a cyano, a haloalkoxy, a solubilising group, —NRR', —NR—CO—R', —CONRR', —SO$_2$NRR', —NRSO$_2$R' group wherein R and R' are each independently selected from hydrogen, alkyl group or aryl group or heteroaryl group;
- $R_2$, $R_3$ and $R_4$ are each independently selected from hydrogen, halogen, cyano, a $C_1$-$C_6$ alkyl group, a $C_3$-$C_7$ cycloalkyl group, a $C_1$-$C_4$ alkoxy group, a $C_1$-$C_4$ haloalkyl group, —NRR', —NR—CO—R', —CONRR' group wherein R and R' are each independently selected from hydrogen or a $C_1$-$C_6$ alkyl group;
- $R_5$ is hydrogen, a $C_1$-$C_6$ alkyl group or a solubilising group;
- X is —(C=O)—, —O—, —S—, —NR$_6$— or —(CH$_2$)$_n$— wherein n is 0, 1 or 2 and $R_6$ represent a hydrogen, a $C_1$-$C_6$ alkyl group or a solubilising group;
- Q is an alkyl group or aryl group or heteroaryl group or heterocycloalkyl group, wherein the alkyl group, aryl group, heteroaryl group and heterocycloalkyl group are unsubstituted or substituted by one or more substituents selected from a halogen, a halomethyl, a linear or branched $C_1$-$C_6$ alkyl group, a $C_1$-$C_4$ alkoxy group, an $C_1$-$C_4$ haloalkyl group, a $C_1$-$C_4$ hydroxyalkyl group, a $C_3$-$C_7$ cycloalkyl group, an aryl group, a heteroaryl group, a heterocycloalkyl group, a hydroxyl, a thioalkyl, a cyano, a haloalkoxy, a —C≡C—R, a solubilising group, —NRR', —NR—CO—R', —CONRR', SO$_2$R, —SO$_2$NRR', —NRSO$_2$R', —(CH$_2$)$_p$—NRR', —O—(CH$_2$)$_q$—NRR', —(CH$_2$)$_p$—R", —O—(CH$_2$)$_q$—R" group wherein R and R' are each independently selected from hydrogen, an alkyl group, or an aryl group or an heteroaryl group, R" is an heteroaryl or an heterocycloalkyl group, p is 1 or 2 and q is 2 or 3.

The invention covers prodrugs of the compounds of the invention.

"Prodrug" means any compound administered in an inactive or significantly less active form than after its bioactivation. Once administered, the prodrug is metabolised in vivo, in one or more steps, into a therapeutically active compound (drug). A prodrug is usually not a therapeutically active compound itself and will usually not elicit in vitro the biological response of the corresponding therapeutically active compound after bioactivation.

Unless otherwise specified, the below terms used herein are defined as follows.

As used herein, the term "alkyl" means a saturated straight chain or branched non-cyclic hydrocarbon having from 1 to 10 carbon atoms, preferably from 1 to 6 carbon atoms, more preferably from 1 to 4 carbon atoms. Representative saturated straight chain alkyls include methyl, ethyl, n-propyl, n-butyl, n-pentyl, n-hexyl, n-heptyl, n-octyl, n-nonyl and n-decyl; while saturated branched alkyls include isopropyl, sec-butyl, isobutyl, tert-butyl, isopentyl, 2-methylbutyl, 3-methylbutyl, 2-methylpentyl, 3-methylpentyl, 4-methylpentyl, 2-methylhexyl, 3-methylhexyl, 4-methylhexyl, 5-methylhexyl, 2,3-dimethylbutyl, 2,3-dimethylpentyl, 2,4-dimethylpentyl, 2,3-dimethylhexyl, 2,4-dimethylhexyl, 2,5-dimethylhexyl, 2,2-dimethylpentyl, 2,2-dimethylhexyl, 3,3-dimethylpentyl, 3,3-dimethylhexyl, 4,4-dimethylhexyl, 2-ethylpentyl, 3-ethylpentyl, 2-ethylhexyl, 3-ethylhexyl, 4-ethylhexyl, 2-methyl-2-ethylpentyl, 2-methyl-3-ethylpentyl, 2-methyl-4-ethylpentyl, 2-methyl-2-ethylhexyl, 2-methyl-3-ethylhexyl, 2-methyl-4-ethylhexyl, 2,2-diethylpentyl, 3,3-diethylhexyl, 2,2-diethylhexyl, 3,3-diethylhexyl and the like. Alkyl groups included in compounds of this invention may be optionally substituted with one or more substituents. Alkyl groups included in compounds of this invention may be optionally substituted with a solubilising group.

As used herein, the term "aryl" means a monocyclic or polycyclic-aromatic radical comprising carbon and hydrogen atoms. Examples of suitable aryl groups include, but are not limited to, phenyl, tolyl, anthracenyl, fluorenyl, indenyl, azulenyl, and naphthyl, as well as benzo-fused carbocyclic moieties such as 5,6,7,8-tetrahydronaphthyl. An aryl group can be unsubstituted or substituted with one or more substituents. Aryl groups included in compounds of this invention may be optionally substituted with a solubilising group.

As used herein, the term "alkoxy" refers to an alkyl group as defined above which is attached to another moiety by an oxygen atom. Examples of alkoxy groups include methoxy, isopropoxy, ethoxy, tert-butoxy, and the like. Alkoxy groups may be optionally substituted with one or more substituents. Alkoxy groups included in compounds of this invention may be optionally substituted with a solubilising group.

As used herein, the term "thioalkyl" refers to an alkyl group as defined above which is attached to another moiety by a sulfur atom. Thioalkyl groups may be optionally substituted with one or more substituents. Thioalkyl groups included in compounds of this invention may be optionally substituted with a solubilising group.

As used herein, the term "heterocycloalkyl" means a monocyclic or polycyclic group having at least one heteroatom selected from O, N or S, and which has from 2 to 11 carbon atoms, which may be saturated or unsaturated, but is not aromatic. Examples of heterocycloalkyl groups including (but not limited to): piperidinyl, piperazinyl, N-methylpiperazinyl, 2-oxopiperazinyl, 2-oxopiperidinyl, 2-oxopyrrolidinyl, 4-piperidonyl, pyrrolidinyl, hydantoinyl, valerolactamyl, oxiranyl, oxetanyl, tetrahydropyranyl, tetrahydrothiopyranyl, tetrahydropyrindinyl, tetrahydropyrimidinyl, tetrahydrothiopyranyl sulfone, tetrahydrothiopyranyl sulfoxide, morpholinyl, thiomorpholinyl, thiomorpholinyl sulfoxide, thiomorpholinyl sulfone, 1,3-dioxolane, tetrahydrofuranyl, dihydrofuranyl-2-one, tetrahydrothienyl, and tetrahydro-1,1-dioxothienyl. Typically, monocyclic heterocycloalkyl groups have 3 to 7 members. Preferred 3 to 7 membered monocyclic heterocycloalkyl groups are those having 5 or 6 ring atoms. A heteroatom may be substituted with a protecting group known to those of ordinary skill in the art, for example, the hydrogen on a nitrogen may be substituted with a tert-butoxycarbonyl group. Furthermore, heterocycloalkyl groups may be optionally substituted with one or more substituents. In addition, the point of attachment of a heterocyclic ring to another group may be at either a carbon atom or a heteroatom of a heterocyclic ring. Only stable isomers of such substituted heterocyclic groups are contemplated in this definition.

As used herein, the term "heteroaryl" or like terms mean a monocyclic or polycyclic heteroaromatic ring comprising carbon atom ring members and one or more heteroatom ring members (such as, for example, oxygen, sulfur or nitrogen). Typically, a heteroaryl group has from 1 to about 5 heteroatom ring members and from 1 to about 14 carbon atom ring members. Representative heteroaryl groups include pyridyl, 1-oxo-pyridyl, furanyl, benzo[1,3]dioxolyl, benzo[1,4]dioxinyl, thienyl, pyrrolyl, oxazolyl, imidazolyl, thiazolyl, isoxazolyl, quinolinyl, pyrazolyl, isothiazolyl, pyridazinyl, pyrimidinyl, pyrazinyl, triazinyl, triazolyl, thiadiazolyl, isoquinolinyl, indazolyl, benzoxazolyl, benzofuryl, indolizinyl, imidazopyridyl, tetrazolyl, benzimidazolyl, benzothiazolyl, benzothiadiazolyl, benzoxadiazolyl, indolyl, tetrahydroindolyl, azaindolyl, imidazopyridyl, quinazolinyl, purinyl, pyrrolo[2,3]pyrimidinyl, pyrazolo[3,4]pyrimidinyl, imidazo[1,2-a]pyridyl, and benzo(b)thienyl. A heteroatom may be substituted with a protecting group known to those of ordinary skill in the art, for example, the hydrogen on nitrogen may be substituted with a tert-butoxycarbonyl group. Heteroaryl groups may be optionally substituted with one or more substituents. In addition, nitrogen or sulfur heteroatom ring members may be oxidized. In one embodiment, the heteroaromatic ring is selected from 5-8 membered monocyclic heteroaryl rings. The point of attachment of a heteroaromatic or heteroaryl ring to another group may be at either a carbon atom or a heteroatom of the heteroaromatic or heteroaryl rings. Heteroaryl groups included in compounds of this invention may be optionally substituted with a solubilising group.

As used herein, the term "haloalkyl" means an alkyl group as defined above in which one or more (including all) the hydrogen radicals are replaced by a halo group, wherein each halo group is independently selected from —F, —Cl, —Br, and —I. The term "halomethyl" means a methyl in which one to three hydrogen radical(s) have been replaced by a halo group. Representative haloalkyl groups include trifluoromethyl, difluoromethyl, bromomethyl, 1,2-dichloroethyl, 4-iodobutyl, 2-fluoropentyl, and the like. Haloalkyl groups may be optionally substituted with one or more substituents. Haloalkyl groups included in compounds of this invention may be optionally substituted with a solubilising group.

As used herein, the term "haloalkoxy" means an alkoxy group as defined above in which one or more (including all) the hydrogen radicals are replaced by a halo group, wherein each halo group is independently selected from —F, —Cl, —Br, and —I. Representative haloalkoxy groups include trifluoromethoxy, bromomethoxy, 1,2-dichloroethoxy, 4-iodobutoxy, 2-fluoropentoxy, and the like. Haloalkoxy groups may be optionally substituted with one or more substituents. Haloalkoxy groups included in compounds of this invention may be optionally substituted with a solubilising group.

As used herein the term "substituent" or "substituted" means that a hydrogen radical on a compound or group or radical or moiety is replaced with any desired group that is substantially stable to reaction conditions in an unprotected form or when protected using a protecting group. Examples of preferred substituents are those found in the exemplary compounds and embodiments disclosed herein, as well as halogen, alkyl or aryl or heteroaryl groups as defined above, hydroxyl, alkoxy as defined above, nitro, thiol, thioalkyl as defined above, cyano, haloalkyl as defined above, haloalkoxy as defined above, cycloalkyl, which may be monocyclic or fused or non-fused polycyclic (e.g., cyclopropyl, cyclobutyl, cyclopentyl, or cyclohexyl) or a solubilising group, as well as —NRR', —NR—CO—R', —CONRR', —SO$_2$NRR' group wherein R and R' are each independently selected from hydrogen, alkyl or aryl or heteroaryl groups as defined above.

As used herein, the term "solubilising" group means a group which has a hydrophilic character sufficient to improve or increase the water-solubility of the compound in which it is included, as compared to an analog compound that does not include the group. The hydrophilic character can be achieved by any means, such as by the inclusion of functional groups that ionize under the conditions of use to form charged moieties (e.g., carboxylic acids, sulfonic acids, phosphoric acids, amines, etc.); groups that include permanent charges (e.g., quaternary ammonium groups); and/or heteroatoms or heteroatomic groups (e.g., O, S, N, NH, N—(CH$_2$)$_z$R, N—(CH$_2$)$_z$—C(O)R, N—(CH$_2$)$_z$—C(O)OR, N—(CH$_2$)$_z$—S(O)$_2$R, N—(CH$_2$)$_z$—S(O)$_2$OR, N—(CH$_2$)$_z$—C(O)NRR', where z is an integer ranging from 0 to 6, R and R' each independently are selected from hydrogen, an alkyl group containing from 1 to 10 carbon atoms and optionally substituted with one or more heteroatoms such as halogen (selected from F, Cl, Br or I), oxygen, and nitrogen; as well as alkoxy group containing from 1 to 10 carbon atoms; as well as aryl and heteroaryl group.

In some embodiments, the solubilising group is a heterocycloalkyl that optionally includes from 1 to 5 substituents, which may themselves be solubilising groups.

In a specific embodiment, the solubilising group is of the formula:

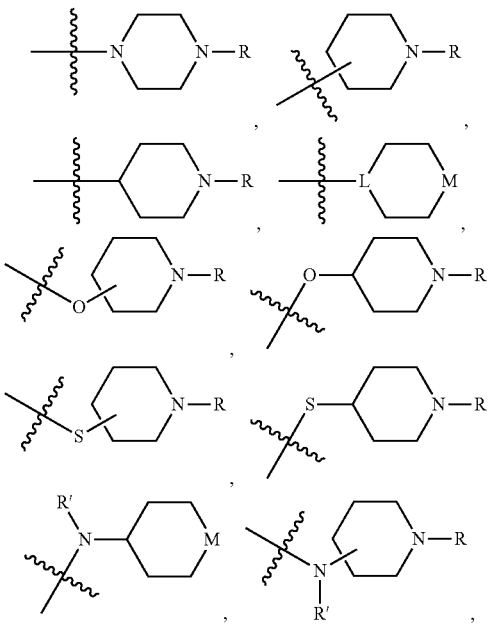

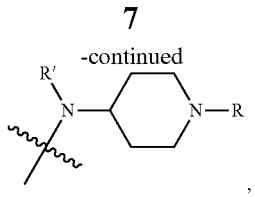

where L is selected from the group consisting of CH and N, M is selected from the group consisting of —CH(R)—, —CH$_2$—, —O—, —S—, —NH—, —N(—(CH$_2$)$_z$—R)—, —N(CH$_2$)$_z$—C(O)R)—, —N(—(CH$_2$)$_z$—C(O)OR)—, —N(—(CH$_2$)$_z$—S(O)$_2$R)—, —N(CH$_2$)$_z$—S(O)$_2$OR)— and —N(—(CH$_2$)$_z$—C(O)NRR')—, where z is an integer ranging from 0 to 6, R and R' each independently are selected from hydrogen, an alkyl group containing from 1 to 10 carbon atoms and optionally substituted with one or more heteroatoms such as halogen (selected from F, Cl, Br or I), oxygen, and nitrogen; as well as alkoxy group containing from 1 to 10 carbon atoms, NRR' group wherein R and R' are each independently selected from hydrogen, alkyl group as defined above optionally substituted with at least one heteroatom, notably oxygen or nitrogen optionally substituted with an alkyl group containing from 1 to 10 carbons optionally substituted; as well as aryl and heteroaryl group, with the proviso that L and M are not both simultaneously CH and CH$_2$, respectively.

In another specific embodiment, the solubilising group is selected from the group consisting of morpholinyl, piperidinyl, pyrrolidinyl, N—(C$_1$-C$_6$)alkyl piperidinyl, in particular N-methyl piperidinyl and N-ethyl piperidinyl, N-(4-piperidinyl)piperidinyl, 4-(1-piperidinyl)piperidinyl, 1-pyrrolidinylpiperidinyl, 4-morpholinopiperidinyl, 4-(N-methyl-1-piperazinyl)piperidinyl, piperazinyl, N—(C$_1$-C$_6$)alkylpiperazinyl, in particular N-methyl piperazinyl and N-ethyl piperazinyl, N—(C$_3$-C$_6$)cycloalkyl piperazinyl, in particular N-cyclohexyl piperazinyl, pyrrolidinyl, N—(C$_1$-C$_6$)alkyl pyrrolidinyl, in particular N-methyl pyrrolidinyl and N-ethyl pyrrolidinyl, diazepinyl, N—(C$_1$-C$_6$)alkyl azepinyl, in particular N-methyl azepinyl and N-ethyl azepinyl, homopiperazinyl, N-methyl homopiperazinyl, N-ethyl homopiperazinyl, imidazolyl, and the like.

One preferred embodiment is compounds of formula (I) wherein A is thiazole.

Among the compounds of formula I in which ring A is thiazole, the present invention is directed to compounds of the following formula II:

group, a C$_1$-C$_4$ hydroxyalkyl group, a C$_3$-C$_7$ cycloalkyl group, an aryl group, a heteroaryl group, a heterocycloalkyl group, a hydroxyl, a thioalkyl, a cyano, a haloalkoxy, a solubilising group, —NRR', —NR—CO—R', —CONRR', —SO$_2$NRR', —NRSO$_2$R' group wherein R and R' are each independently selected from hydrogen, alkyl group or aryl group or heteroaryl group;

R$_{1b}$ is hydrogen, halogen, NH$_2$, OH, CN, an alkyl group or an aryl group or an heteroaryl group, wherein the alkyl group, aryl group and heteroaryl group are unsubstituted or substituted by one or more substituents selected from an halogen, a linear or branched C$_1$-C$_6$ alkyl group, a C$_1$-C$_4$ alkoxy group, a C$_1$-C$_4$ haloalkyl group, a C$_1$-C$_4$ hydroxyalkyl group, a C$_3$-C$_7$ cycloalkyl group, an aryl group, an heteroaryl group, an heterocycloalkyl group, an hydroxyl, a thioalkyl, a cyano, an haloalkoxy, a solubilising group, —NRR', —NR—CO—R', —CONRR', —SO$_2$NRR', —NRSO$_2$R' group wherein R and R' are each independently selected from hydrogen, alkyl group or aryl group or heteroaryl group;

R$_2$, R$_3$ and R$_4$ are independently selected from hydrogen, halogen, cyano, a C$_1$-C$_6$ alkyl group, a C$_3$-C$_7$ cycloalkyl group, a C$_1$-C$_4$ alkoxy group, a C$_1$-C$_4$ haloalkyl group, —NRR', —NR—CO—R', —CONRR' group wherein R and R' are each independently selected from hydrogen or a C$_1$-C$_6$ alkyl group;

R$_5$, X and Q are as defined above.

Preferred compounds of formula I are those wherein A is thiazole substituted by one R$_1$ representing an aryl or heteroaryl group, optionally substituted by one or more substituents.

According to a particular embodiment, the invention relates to compounds of formula II wherein R$_{1a}$ is hydrogen and R$_{1b}$ is aryl or heteroaryl, optionally substituted by one or more substituents.

Among compounds of formulas I and II, the invention relates to compounds wherein X is —(CH$_2$)n, n is 0, and Q is aryl, for example a phenyl, optionally substituted by one or more substituents.

Among the compounds of formula I in which ring A is thiazole and R$_1$ is depicted above, the present invention is directed to compounds of the following formula III:

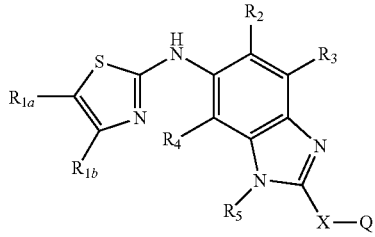

Wherein:
R$_{1a}$ is hydrogen, halogen, NH$_2$, OH, CN, an alkyl group or an aryl group or an heteroaryl group, wherein the alkyl group, aryl group and heteroaryl group are unsubstituted or substituted by one or more substituents selected from a halogen, a linear or branched C$_1$-C$_6$ alkyl group, a C$_1$-C$_4$ alkoxy group, a C$_1$-C$_4$ haloalkyl

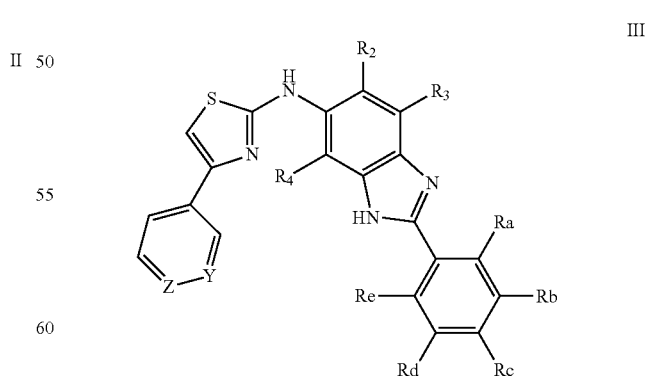

Wherein:
R$_2$ is hydrogen, halogen, cyano, a C$_1$-C$_6$ alkyl group, a C$_3$-C$_7$ cycloalkyl group, a C$_1$-C$_4$ alkoxy group, a C$_1$-C$_4$ haloalkyl group, —NRR', —NR—CO—R', —CONRR' group wherein R and R' are each independently selected from hydrogen or a $C_1$-$C_6$ alkyl group;

$R_3$ is hydrogen, halogen, cyano, a $C_1$-$C_6$ alkyl group, a $C_1$-$C_4$ alkoxy group, a $C_1$-$C_4$ haloalkyl group, —NRR', —NR—CO—R', —CONRR' group wherein R and R' are each independently selected from hydrogen or a $C_1$-$C_6$ alkyl group;

$R_4$ is hydrogen, halogen, cyano, a $C_1$-$C_6$ alkyl group, a $C_1$-$C_4$ alkoxy group, a $C_1$-$C_4$ haloalkyl group, —NRR', —NR—CO—R', —CONRR' group wherein R and R' are each independently selected from hydrogen or a $C_1$-$C_6$ alkyl group;

Z is N or $CR_7$, wherein $R_7$ is hydrogen, halogen, cyano, a $C_1$-$C_6$ alkyl group, a $C_1$-$C_4$ alkoxy group, a $C_1$-$C_4$ haloalkyl group, an heterocycloalkyl group, —NRR', —CONRR' group wherein R and R' are each independently selected from hydrogen or a $C_1$-$C_6$ alkyl group;

Y is N or $CR_8$, wherein $R_8$ is hydrogen, halogen, cyano, a $C_1$-$C_6$ alkyl group, a $C_1$-$C_4$ alkoxy group, a $C_1$-$C_4$ haloalkyl group, an heterocycloalkyl group, —NRR', —CONRR' group wherein R and R' are each independently selected from hydrogen or a $C_1$-$C_6$ alkyl group;

Ra, Rb, Rc, Rd and Re are each independently selected from hydrogen, a halogen, a halomethyl, a linear or branched $C_1$-$C_6$ alkyl group, a $C_1$-$C_4$ alkoxy group, a $C_1$-$C_4$ haloalkyl group, a $C_1$-$C_4$ hydroxyalkyl group, a $C_3$-$C_7$ cycloalkyl group, an aryl group, a heteroaryl group, a heterocycloalkyl group, a hydroxyl, a thioalkyl, a cyano, a haloalkoxy, a —C≡C—R, a solubilising group, —NRR', —NR—CO—R', —CONRR', $SO_2R$, —$SO_2NRR'$, —$NRSO_2R'$, —$(CH_2)_p$—NRR', —O—$(CH_2)_q$—NRR', —$(CH_2)_p$—R'', —O—$(CH_2)_q$—R'' group wherein R and R' are each independently selected from hydrogen, an alkyl group, or an aryl group or a heteroaryl group, R'' is an heteroaryl or an heterocycloalkyl group, p is 1 or 2 and q is 2 or 3;

According to one embodiment, $R_2$ is a $C_1$-$C_6$ alkylgroup, for example a methyl group, $R_3$ and $R_4$ are hydrogen.

Among the compounds of formula I in which ring A is thiazole, the present invention is directed to compounds of the following formula IV:

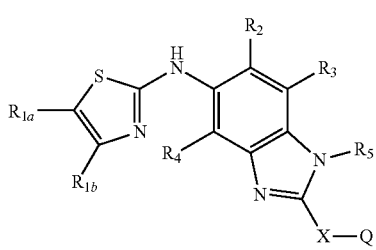

Wherein:

$R_{1a}$ is hydrogen, halogen, $NH_2$, OH, CN, an alkyl group or an aryl group or an heteroaryl group, wherein the alkyl group, aryl group and heteroaryl group are unsubstituted or substituted by one or more substituents selected from a halogen, a linear or branched $C_1$-$C_6$ alkyl group, a $C_1$-$C_4$ alkoxy group, a $C_1$-$C_4$ haloalkyl group, a $C_1$-$C_4$ hydroxyalkyl group, a $C_3$-$C_7$ cycloalkyl group, an aryl group, a heteroaryl group, a heterocycloalkyl group, a hydroxyl, a thioalkyl, a cyano, a haloalkoxy, a solubilising group, —NRR', —NR—CO—R', —CONRR', —$SO_2NRR'$, —$NRSO_2R'$ group wherein R and R' are each independently selected from hydrogen, alkyl group or aryl group or heteroaryl group;

$R_{1b}$ is hydrogen, halogen, $NH_2$, OH, CN, an alkyl group or an aryl group or an heteroaryl group, wherein the alkyl group, aryl group and heteroaryl group are unsubstituted or substituted by one or more substituents selected from an halogen, a linear or branched $C_1$-$C_6$ alkyl group, a $C_1$-$C_4$ alkoxy group, a $C_1$-$C_4$ haloalkyl group, a $C_1$-$C_4$ hydroxyalkyl group, a $C_3$-$C_7$ cycloalkyl group, an aryl group, an heteroaryl group, an heterocycloalkyl group, an hydroxyl, a thioalkyl, a cyano, an haloalkoxy, a solubilising group, —NRR', —NR—CO—R', —CONRR', —$SO_2NRR'$, —$NRSO_2R'$ group wherein R and R' are each independently selected from hydrogen, alkyl group or aryl group or heteroaryl group;

$R_2$, $R_3$ and $R_4$ are independently selected from hydrogen, halogen, cyano, a $C_1$-$C_6$ alkyl group, a $C_3$-$C_7$ cycloalkyl group, a $C_1$-$C_4$ alkoxy group, a $C_1$-$C_4$ haloalkyl group, —NRR', —NR—CO—R', —CONRR' group wherein R and R' are each independently selected from hydrogen or a $C_1$-$C_6$ alkyl group;

$R_5$, X and Q are as defined above.

According to a particular embodiment, the invention relates to compounds of formula IV wherein $R_{1a}$ is hydrogen and $R_{1b}$ is aryl or heteroaryl, optionally substituted by one or more substituents.

Among compounds of formulas I and IV, the invention relates to compounds wherein X is —$(CH_2)n$, n is 0, and Q is aryl, for example a phenyl, optionally substituted by one or more substituents.

Among compounds of formulas I and IV, the invention relates to compounds wherein R5 is a $C_1$-$C_6$ alkyl group, for example a methyl, ethyl, isopropyl, more particularly methyl.

Among the compounds of formula I in which ring A is thiazole and $R_1$ is depicted above, the present invention is directed to compounds of the following formula V:

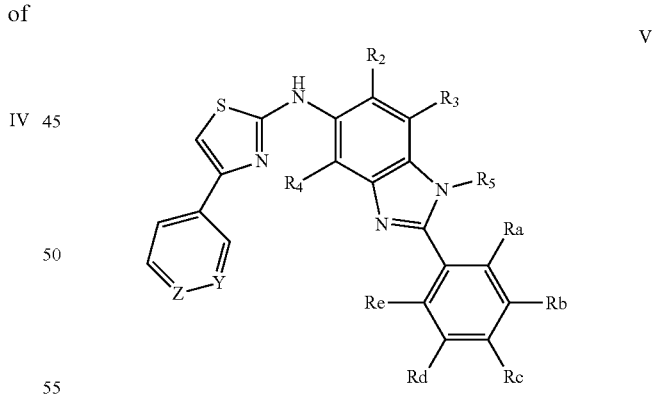

Wherein:

$R_2$ is hydrogen, halogen, cyano, a $C_1$-$C_6$ alkyl group, a $C_3$-$C_7$ cycloalkyl group, a $C_1$-$C_4$ alkoxy group, a $C_1$-$C_4$ haloalkyl group, —NRR', —NR—CO—R', —CONRR' group wherein R and R' are each independently selected from hydrogen or a $C_1$-$C_6$ alkyl group;

$R_3$ is hydrogen, halogen, cyano, a $C_1$-$C_6$ alkyl group, a $C_1$-$C_4$ alkoxy group, a $C_1$-$C_4$ haloalkyl group, —NRR', —NR—CO—R', —CONRR' group wherein R and R' are each independently selected from hydrogen or a $C_1$-$C_6$ alkyl group;

$R_4$ is hydrogen, halogen, cyano, a $C_1$-$C_6$ alkyl group, a $C_1$-$C_4$ alkoxy group, a $C_1$-$C_4$ haloalkyl group, —NRR', —NR—CO—R', —CONRR' group wherein R and R' are each independently selected from hydrogen or a $C_1$-$C_6$ alkyl group;

$R_5$ is hydrogen, a $C_1$-$C_6$ alkyl group or a solubilising group;

Z is N or $CR_7$, wherein $R_7$ is hydrogen, halogen, cyano, a $C_1$-$C_6$ alkyl group, a $C_1$-$C_4$ alkoxy group, a $C_1$-$C_4$ haloalkyl group, an heterocycloalkyl group, —NRR', —CONRR' group wherein R and R' are each independently selected from hydrogen or a $C_1$-$C_6$ alkyl group;

Y is N or $CR_8$, wherein $R_8$ is hydrogen, halogen, cyano, a $C_1$-$C_6$ alkyl group, a $C_1$-$C_4$ alkoxy group, a $C_1$-$C_4$ haloalkyl group, an heterocycloalkyl group, —NRR', —CONRR' group wherein R and R' are each independently selected from hydrogen or a $C_1$-$C_6$ alkyl group;

Ra, Rb, Rc, Rd and Re are each independently selected from an hydrogen, an halogen, an halomethyl, a linear or branched $C_1$-$C_6$ alkyl group, a $C_1$-$C_4$ alkoxy group, an $C_1$-$C_4$ haloalkyl group, a $C_1$-$C_4$ hydroxyalkyl group, a $C_3$-$C_7$ cycloalkyl group, an aryl group, an heteroaryl group, an heterocycloalkyl group, an hydroxyl, a thioalkyl, a cyano, an haloalkoxy, a —C≡C—R, a solubilising group, —NRR', —NR—CO—R', —CONRR', —SO$_2$NRR', —NRSO$_2$R', —(CH$_2$)$_p$—NRR', —O—(CH$_2$)$_q$—NRR', —(CH$_2$)$_p$—R", —O—(CH$_2$)$_q$—R" group wherein R and R' are each independently selected from hydrogen, an alkyl group, or an aryl group or an heteroaryl group, R" is an heteroaryl or an heterocycloalkyl group, p is 1 or 2 and q is 2 or 3.

According to one embodiment, the invention relates to compounds of formula V, wherein $R_2$ is a $C_1$-$C_6$ alkylgroup, for example a methyl group, $R_3$ and $R_4$ are hydrogen and $R_5$ is a $C_1$-$C_6$ alkyl group, for example a methyl ethyl, isopropyl, more particularly methyl.

According to a specific embodiment, the invention relates to compounds of formulas III and V, wherein Ra and Re are hydrogen and Rb, Rc, and Rd are each independently selected from an hydrogen, an halogen, an halomethyl, a linear or branched $C_1$-$C_6$ alkyl group, a $C_1$-$C_4$ alkoxy group, an $C_1$-$C_4$ haloalkyl group, a $C_1$-$C_4$ hydroxyalkyl group, a $C_3$-$C_7$ cycloalkyl group, an aryl group, an heteroaryl group, an heterocycloalkyl group, an hydroxyl, a thioalkyl, a cyano, an haloalkoxy, a —C≡C—R, a solubilising group, —NRR', —NR—CO—R', —CONRR', —SO$_2$NRR', —NRSO$_2$R', —(CH$_2$)$_p$—NRR', —O—(CH$_2$)$_q$—NRR', —(CH$_2$)$_p$—R", —O—(CH$_2$)$_q$—R" group wherein R and R' are each independently selected from hydrogen, an alkyl group, or an aryl group or an heteroaryl group, R" is an heteroaryl or an heterocycloalkyl group, p is 1 or 2 and q is 2 or 3.

According to a specific embodiment, the invention relates to compounds of formulas III and V, wherein Ra and Re are hydrogen, one of Rb, Rc, and Rd is hydrogen, two of Rb, Rc, and Rd are each independently selected from an hydrogen, an halogen, an halomethyl, a linear or branched $C_1$-$C_6$ alkyl group, a $C_1$-$C_4$ alkoxy group, an $C_1$-$C_4$ haloalkyl group, a $C_1$-$C_4$ hydroxyalkyl group, a $C_3$-$C_7$ cycloalkyl group, an aryl group, an heteroaryl group, an heterocycloalkyl group, an hydroxyl, a thioalkyl, a cyano, an haloalkoxy, a —C≡C—R, a solubilising group, —NRR', —NR—CO—R', —CONRR', —SO$_2$NRR', —NRSO$_2$R', —(CH$_2$)$_p$—NRR', —O—(CH$_2$)$_q$—NRR', —(CH$_2$)$_p$—R", —O—(CH$_2$)$_q$—R" group wherein R and R' are each independently selected from hydrogen, an alkyl group, or an aryl group or an heteroaryl group, R" is an heteroaryl or an heterocycloalkyl group, p is 1 or 2 and q is 2 or 3.

According to a specific embodiment, the invention relates to compounds of formulas III and V, wherein Ra and Re are hydrogen, two of Rb, Rc, and Rd are hydrogen, one of Rb, Rc, and Rd is each independently selected from a halogen, a halomethyl, a linear or branched $C_1$-$C_6$ alkyl group, a $C_1$-$C_4$ alkoxy group, a $C_1$-$C_4$ haloalkyl group, a $C_1$-$C_4$ hydroxyalkyl group, a $C_3$-$C_7$ cycloalkyl group, an aryl group, a heteroaryl group, a heterocycloalkyl group, a hydroxyl, a thioalkyl, a cyano, a haloalkoxy, a —C≡C—R, a solubilising group, —NRR', —NR—CO—R', —CONRR', SO$_2$R, —SO$_2$NRR', —NRSO$_2$R', —(CH2)$_p$—NRR', —O—(CH2)$_q$-NRR', —(CH2)$_p$-R", —O—(CH2)$_q$-R" group wherein R and R' are each independently selected from hydrogen, an alkyl group, or an aryl group or a heteroaryl group, R" is an heteroaryl or an heterocycloalkyl group, p is 1 or 2 and q is 2 or 3.

According to a specific embodiment, the invention relates to compounds of formulas I, wherein A-(R1)$_n$ represents one of the following groups: 4-pyridin-3-yl-thiazol-2-yl; 4-pyridin-4-yl-thiazol-2-yl; 4-pyrimidin-5-yl-thiazol-2-yl; 5-pyridin-3-yl-oxazol-2-yl; 5-pyridin-4-yl-oxazol-2-yl; 4-pyridin-3-yl-pyrimidin-2-yl; 4-benzonitrile-4-yl-thiazol-2-yl; 4-benzamide-4-yl-thiazol-2-yl; 4-(2-Chloro-pyridin-4-yl)-thiazol-2-yl-.

Examples of preferred compounds of the above formula are depicted in table 1 below:

TABLE 1

| Ex # | Chemical Structure | Name | LCMS |
|---|---|---|---|
| 001 | 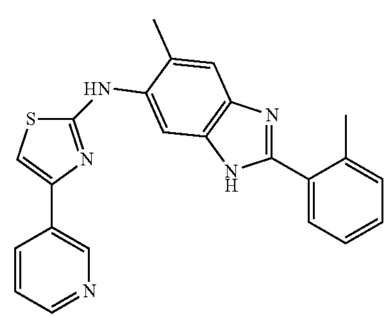 [SMILES: Cc1cc2nc(-c3ccccc3C)[nH]c2cc1Nc1nc(-c2cccnc2)cs1] | (6-Methyl-2-o-tolyl-3H-benzoimidazol-5-yl)-(4-pyridin-3-yl-thiazol-2-yl)-amine | (ESI-) m/z 396 (M − H)$^-$ Retention time = 1.85 mins |

TABLE 1-continued

| Ex # | Chemical Structure | Name | LCMS |
|---|---|---|---|
| 002 | 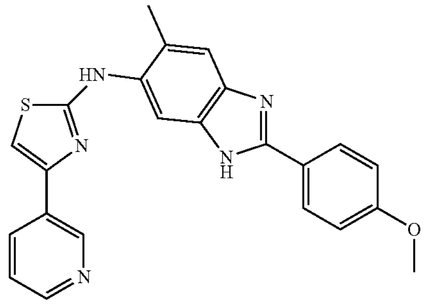 [SMILES: COc1ccc(-c2nc3cc(C)c(Nc4nc(-c5cccnc5)cs4)cc3[nH]2)cc1] | [2-(4-Methoxy-phenyl)-6-methyl-3H-benzoimidazol-5-yl]-(4-pyridin-3-yl-thiazol-2-yl)-amine | (ESI-) m/z 412 (M − H)⁻ Retention time = 1.89 mins |
| 003 | 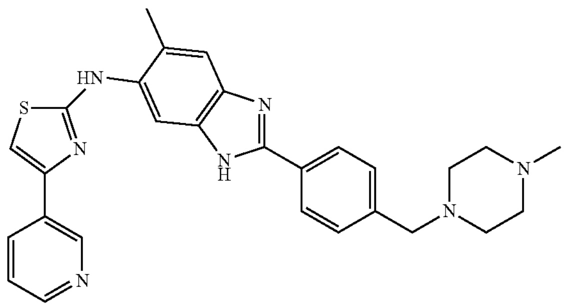 [SMILES: Cc1cc2nc(-c3ccc(CN4CCN(C)CC4)cc3)[nH]c2cc1Nc1nc(-c2cccnc2)cs1] | {6-Methyl-2-[4-(4-methyl-piperazin-1-ylmethyl)-phenyl]-3H-benzoimidazol-5-yl}-(4-pyridin-3-yl-thiazol-2-yl)-amine | (ESI-) m/z 494 (M − H)⁻ Retention time = 1.50 mins |
| 004 | 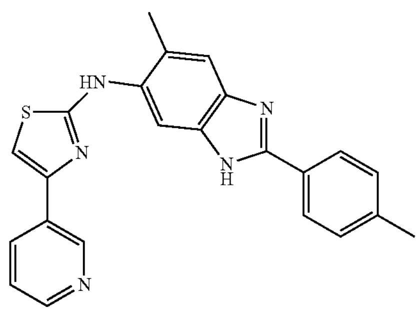 [SMILES: Cc1ccc(-c2nc3cc(C)c(Nc4nc(-c5cccnc5)cs4)cc3[nH]2)cc1] | (6-Methyl-2-p-tolyl-3H-benzoimidazol-5-yl)-(4-pyridin-3-yl-thiazol-2-yl)-amine | (ESI-) m/z 396 (M − H)⁻ Retention time = 1.96 mins |
| 005 | 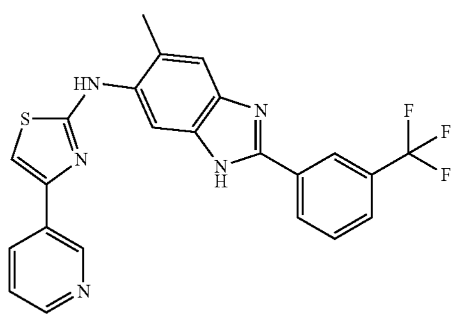 [SMILES: Cc1cc2nc(-c3cccc(C(F)(F)F)c3)[nH]c2cc1Nc1nc(-c2cccnc2)cs1] | [6-Methyl-2-(3-trifluoromethyl-phenyl)-3H-benzoimidazol-5-yl]-(4-pyridin-3-yl-thiazol-2-yl)-amine | (ESI-) m/z 450 (M − H)⁻ Retention time = 2.36 mins |
| 006 | 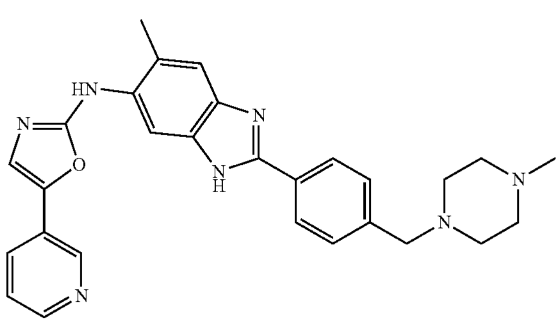 [SMILES: Cc1cc2nc(-c3ccc(CN4CCN(C)CC4)cc3)[nH]c2cc1Nc1ncc(-c2cccnc2)o1] | {6-Methyl-2-[4-(4-methyl-piperazin-1-ylmethyl)-phenyl]-3H-benzoimidazol-5-yl}-(5-pyridin-3-yl-oxazol-2-yl)-amine | (ESI-) m/z 478 (M − H)⁻ Retention time = 1.42 mins |

TABLE 1-continued

| Ex # | Chemical Structure | Name | LCMS |
|---|---|---|---|
| 007 | 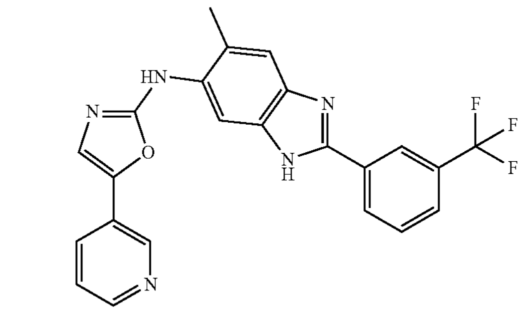 [SMILES: Cc1cc2nc(-c3cccc(C(F)(F)F)c3)[nH]c2cc1Nc1ncc(-c2cccnc2)o1] | [6-Methyl-2-(3-trifluoromethyl-phenyl)-3H-benzoimidazol-5-yl]-(5-pyridin-3-yl-oxazol-2-yl)-amine | (ESI-) m/z 434 (M − H)⁻ Retention time = 2.24 mins |
| 008 | 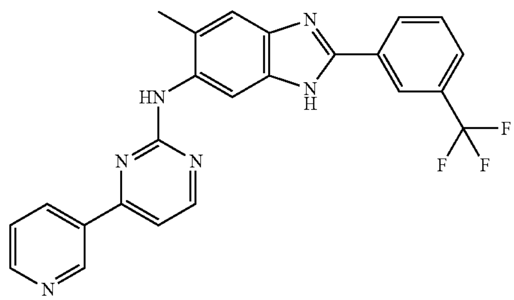 [SMILES: Cc1cc2nc(-c3cccc(C(F)(F)F)c3)[nH]c2cc1Nc1nccc(-c2cccnc2)n1] | [6-Methyl-2-(3-trifluoromethyl-phenyl)-3H-benzoimidazol-5-yl]-(4-pyridin-3-yl-pyrimidin-2-yl)-amine | (ESI-) m/z 445 (M − H)⁻ Retention time = 2.37 mins |
| 009 | 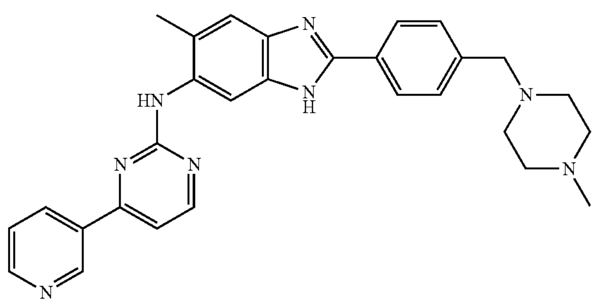 [SMILES: Cc1cc2nc(-c3ccc(CN4CCN(C)CC4)cc3)[nH]c2cc1Nc1nccc(-c2cccnc2)n1] | {6-Methyl-2-[4-(4-methyl-piperazin-1-ylmethyl)-phenyl]-3H-benzoimidazol-5-yl}-(4-pyridin-3-yl-pyrimidin-2-yl)-amine | (ESI-) m/z 489 (M − H)⁻ Retention time = 1.51 mins |
| 010 | 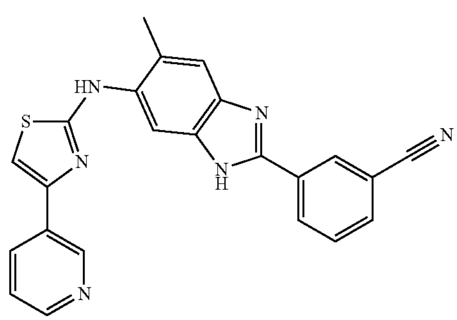 [SMILES: Cc1cc2nc(-c3cccc(C#N)c3)[nH]c2cc1Nc1nc(-c2cccnc2)cs1] | 3-[5-Methyl-6-(4-pyridin-3-yl-thiazol-2-ylamino)-1H-benzoimidazol-2-yl]-benzonitrile | (ESI-) m/z 407 (M − H)⁻ Retention time = 2.01 mins |
| 011 | 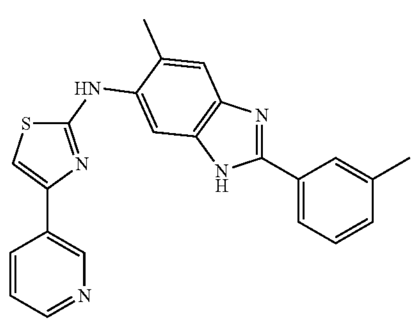 [SMILES: Cc1cccc(-c2nc3cc(C)c(Nc4nc(-c5cccnc5)cs4)cc3[nH]2)c1] | (6-Methyl-2-m-tolyl-3H-benzoimidazol-5-yl)-(4-pyridin-3-yl-thiazol-2-yl)-amine | (ESI-) m/z 396 (M − H)⁻ Retention time = 1.96 mins |

TABLE 1-continued

| Ex # | Chemical Structure | Name | LCMS |
|---|---|---|---|
| 012 | 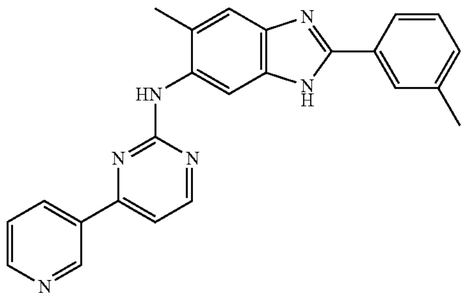 | (6-Methyl-2-m-tolyl-3H-benzoimidazol-5-yl)-(4-pyridin-3-yl-pyrimidin-2-yl)-amine | (ESI[30]) m/z 391 (M − H)⁻ Retention time = 2.01 mins |
| 013 | 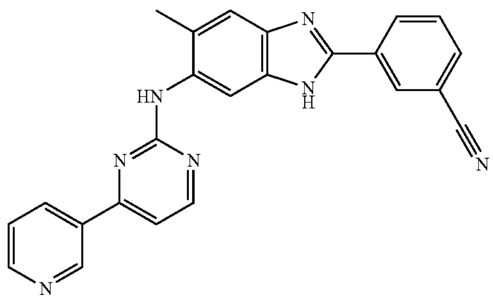 [SMILES: Cc1cc2nc(-c3cccc(C#N)c3)[nH]c2cc1Nc1nccc(-c2cccnc2)n1] | 3-[5-Methyl-6-(4-pyridin-3-yl-pyrimidin-2-ylamino)-1H-benzoimidazol-2-yl]-benzonitrile | (ESI-) m/z 402 (M − H)⁻ Retention time = 2.00 mins |
| 014 | 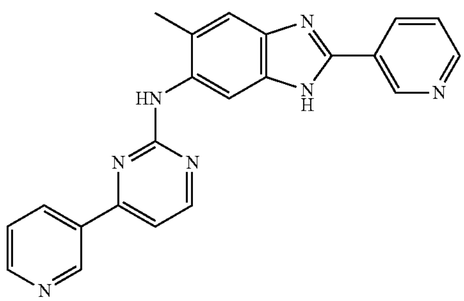 [SMILES: Cc1cc2nc(-c3cccnc3)[nH]c2cc1Nc1nccc(-c2cccnc2)n1] | (6-Methyl-2-pyridin-3-yl-3H-benzoimidazol-5-yl)-(4-pyridin-3-yl-pyrimidin-2-yl)-amine | (ESI-) m/z 378 (M − H)⁻ Retention time = 1.65 mins |
| 015 | 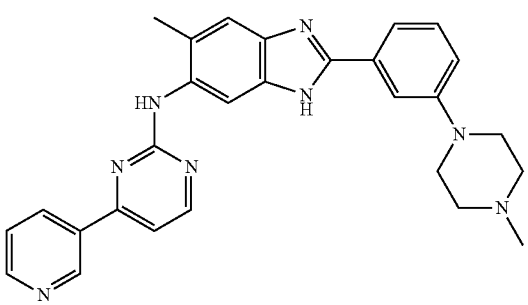 [SMILES: Cc1cc2nc(-c3cccc(N4CCN(C)CC4)c3)[nH]c2cc1Nc1nccc(-c2cccnc2)n1] | {6-Methyl-2-[3-(4-methyl-piperazin-1-yl)-phenyl]-3H-benzoimidazol-5-yl}-(4-pyridin-3-yl-pyrimidin-2-yl)-amine | (ESI-) m/z 475 (M − H)⁻ Retention time = 1.54 mins |
| 016 | 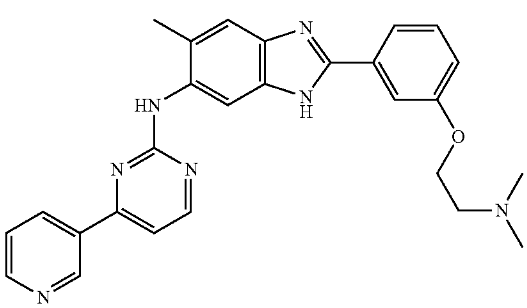 [SMILES: Cc1cc2nc(-c3cccc(OCCN(C)C)c3)[nH]c2cc1Nc1nccc(-c2cccnc2)n1] | {2-[3-(2-Dimethylamino-ethoxy)-phenyl]-6-methyl-3H-benzoimidazol-5-yl}-(4-pyridin-3-yl-pyrimidin-2-yl)-amine | (ESI-) m/z 464 (M − H)⁻ Retention time = 1.53 mins |

TABLE 1-continued

| Ex # | Chemical Structure | Name | LCMS |
|---|---|---|---|
| 017 | 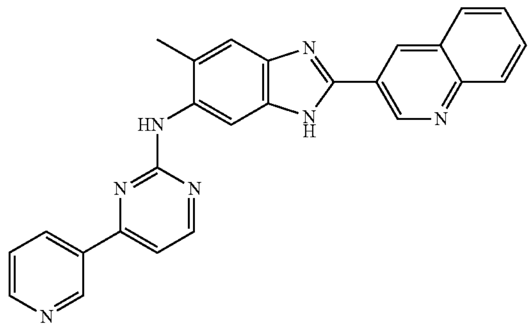 [SMILES: Cc1cc2nc(-c3cnc4ccccc4c3)[nH]c2cc1Nc1nccc(-c2cccnc2)n1] | (6-Methyl-2-quinolin-3-yl-3H-benzoimidazol-5-yl)-(4-pyridin-3-yl-pyrimidin-2-yl)-amine | (ESI-) m/z 428 (M − H)⁻ Retention time = 2.02 mins |
| 018 | 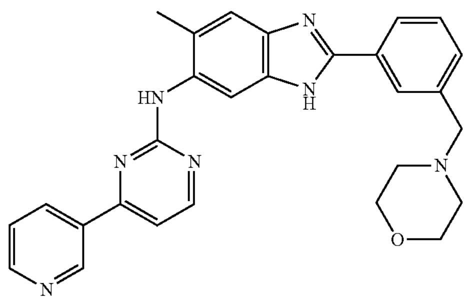 [SMILES: Cc1cc2nc(-c3cccc(CN4CCOCC4)c3)[nH]c2cc1Nc1nccc(-c2cccnc2)n1] | [6-Methyl-2-(3-morpholin-4-ylmethyl-phenyl)-3H-benzoimidazol-5-yl]-(4-pyridin-3-yl-pyrimidin-2-yl)-amine | (ESI-) m/z 476 (M − H)⁻ Retention time = 1.50 mins |
| 019 | 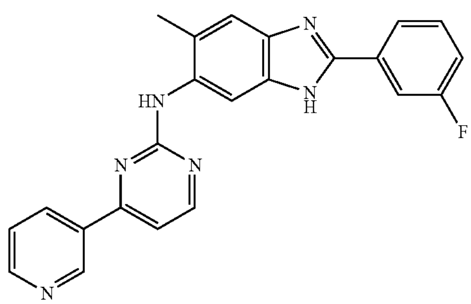 [SMILES: Cc1cc2nc(-c3cccc(F)c3)[nH]c2cc1Nc1nccc(-c2cccnc2)n1] | [2-(3-Fluoro-phenyl)-6-methyl-3H-benzoimidazol-5-yl]-(4-pyridin-3-yl-pyrimidin-2-yl)-amine | (ESI-) m/z 395 (M − H)⁻ Retention time = 1.97 mins |
| 020 | 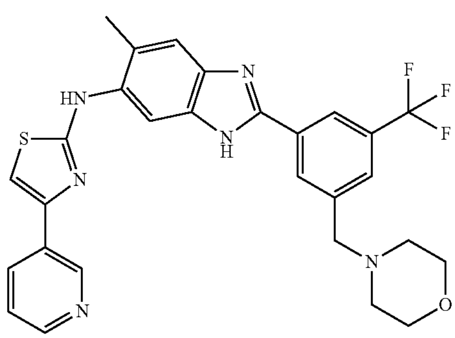 [SMILES: Cc1cc2nc(-c3cc(CN4CCOCC4)cc(C(F)(F)F)c3)[nH]c2cc1Nc1nc(-c2cccnc2)cs1] | [6-Methyl-2-(3-morpholin-4-ylmethyl-5-trifluoromethyl-phenyl)-3H-benzoimidazol-5-yl]-(4-pyridin-3-yl-thiazol-2-yl)-amine | (ESI-) m/z 549 (M − H)⁻ Retention time = 1.90 mins |
| 021 | 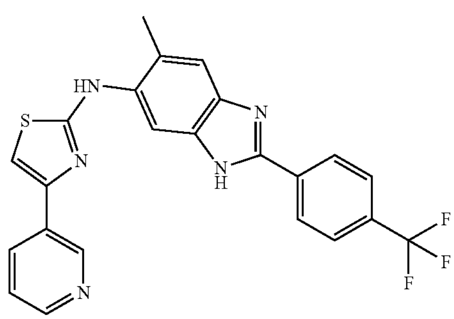 [SMILES: Cc1cc2nc(-c3ccc(C(F)(F)F)cc3)[nH]c2cc1Nc1nc(-c2cccnc2)cs1] | [6-Methyl-2-(4-trifluoromethyl-phenyl)-3H-benzoimidazol-5-yl]-(4-pyridin-3-yl-thiazol-2-yl)-amine | (ESI-) m/z 450 (M − H)⁻ Retention time = 2.38 mins |

TABLE 1-continued

| Ex # | Chemical Structure | Name | LCMS |
|---|---|---|---|
| 022 | 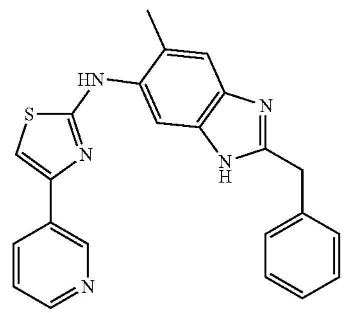 [SMILES: Cc1cc2nc(Cc3ccccc3)[nH]c2cc1Nc1nc(-c2cccnc2)cs1] | (2-Benzyl-6-methyl-3H-benzoimidazol-5-yl)-(4-pyridin-3-yl-thiazol-2-yl)-amine | (ESI-) m/z 396 (M − H)⁻ Retention time = 1.85 mins |
| 023 | 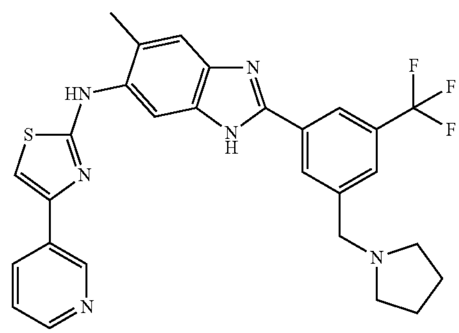 [SMILES: Cc1cc2nc(-c3cc(CN4CCCC4)cc(C(F)(F)F)c3)[nH]c2cc1Nc1nc(-c2cccnc2)cs1] | [6-Methyl-2-(3-pyrrolidin-1-ylmethyl-5-trifluoromethyl-phenyl)-3H-benzoimidazol-5-yl]-(4-pyridin-3-yl-thiazol-2-yl)-amine | (ESI-) m/z 533 (M − H)⁻ Retention time = 1.93 mins |
| 024 | 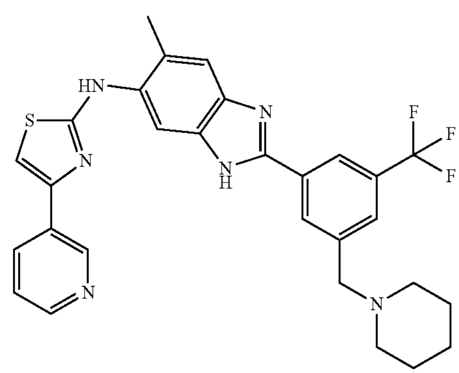 [SMILES: Cc1cc2nc(-c3cc(CN4CCCCC4)cc(C(F)(F)F)c3)[nH]c2cc1Nc1nc(-c2cccnc2)cs1] | [6-Methyl-2-(3-piperidin-1-ylmethyl-5-trifluoromethyl-phenyl)-3H-benzoimidazol-5-yl]-(4-pyridin-3-yl-thiazol-2-yl)-amine | (ESI-) m/z 547 (M − H)⁻ Retention time = 1.99 mins |
| 025 | 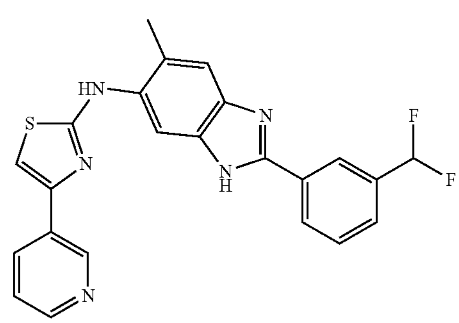 [SMILES: Cc1cc2nc(-c3cccc(C(F)F)c3)[nH]c2cc1Nc1nc(-c2cccnc2)cs1] | [2-(3-Difluoromethyl-phenyl)-6-methyl-3H-benzoimidazol-5-yl]-(4-pyridin-3-yl-thiazol-2-yl)-amine | (ESI-) m/z 432 (M − H)⁻ Retention time = 2.08 mins |

TABLE 1-continued

| Ex # | Chemical Structure | Name | LCMS |
|---|---|---|---|
| 026 | 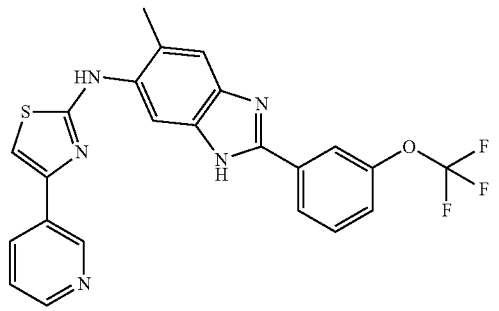 [SMILES: Cc1cc2nc(-c3cccc(OC(F)(F)F)c3)[nH]c2cc1Nc1nc(-c2cccnc2)cs1] | [6-Methyl-2-(3-trifluoromethoxy-phenyl)-3H-benzoimidazol-5-yl]-(4-pyridin-3-yl-thiazol-2-yl)-amine | (ESI-) m/z 466 (M − H)⁻ Retention time = 2.42 mins |
| 027 | 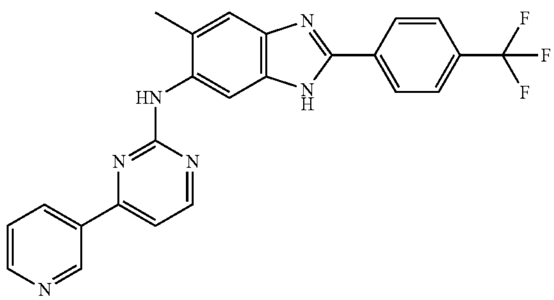 [SMILES: Cc1cc2nc(-c3ccc(C(F)(F)F)cc3)[nH]c2cc1Nc1nccc(-c2cccnc2)n1] | [6-Methyl-2-(4-trifluoromethyl-phenyl)-3H-benzoimidazol-5-yl]-(4-pyridin-3-yl-pyrimidin-2-yl)-amine | (ESI-) m/z 445 (M − H)⁻ Retention time = 2.39 mins |
| 028 | 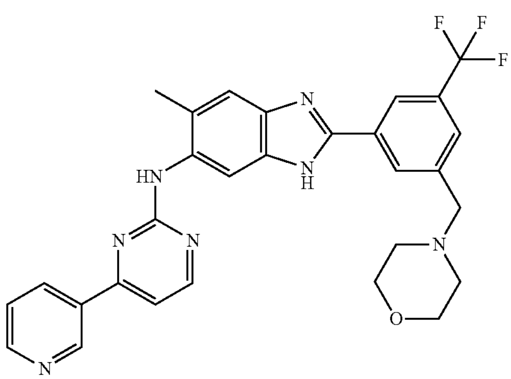 [SMILES: Cc1cc2nc(-c3cc(CN4CCOCC4)cc(C(F)(F)F)c3)[nH]c2cc1Nc1nccc(-c2cccnc2)n1] | [6-Methyl-2-(3-morpholin-4-ylmethyl-5-trifluoromethyl-phenyl)-3H-benzoimidazol-5-yl]-(4-pyridin-3-yl-pyrimidin-2-yl)-amine | (ESI-) m/z 544 (M − H)⁻ Retention time = 1.95 mins |
| 029 | 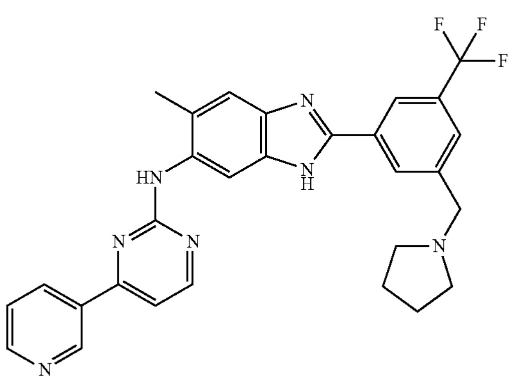 [SMILES: Cc1cc2nc(-c3cc(CN4CCCC4)cc(C(F)(F)F)c3)[nH]c2cc1Nc1nccc(-c2cccnc2)n1] | [6-Methyl-2-(3-pyrrolidin-1-ylmethyl-5-trifluoromethyl-phenyl)-3H-benzoimidazol-5-yl]-(4-pyridin-3-yl-pyrimidin-2-yl)-amine | (ESI-) m/z 528 (M − H)⁻ Retention time = 1.98 mins |

| Ex # | Chemical Structure | Name | LCMS |
| --- | --- | --- | --- |
| 030 | 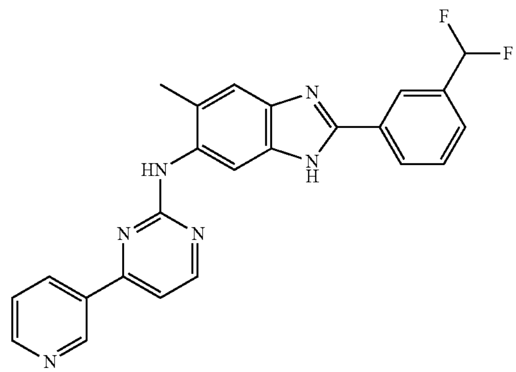 [SMILES: Cc1cc2nc(-c3cccc(C(F)F)c3)[nH]c2cc1Nc1nccc(-c2cccnc2)n1] | [2-(3-Difluoromethyl-phenyl)-6-methyl-3H-benzoimidazol-5-yl]-(4-pyridin-3-yl-pyrimidin-2-yl)-amine | (ESI-) m/z 427 (M − H)⁻ Retention time = 2.08 mins |
| 031 | 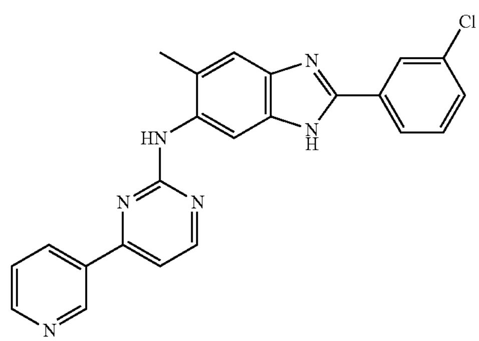 [SMILES: Cc1cc2nc(-c3cccc(Cl)c3)[nH]c2cc1Nc1nccc(-c2cccnc2)n1] | [2-(3-Chloro-phenyl)-6-methyl-3H-benzoimidazol-5-yl]-(4-pyridin-3-yl-pyrimidin-2-yl)-amine | (ESI-) m/z 411 (M − H)⁻ Retention time = 2.15 mins |
| 032 | 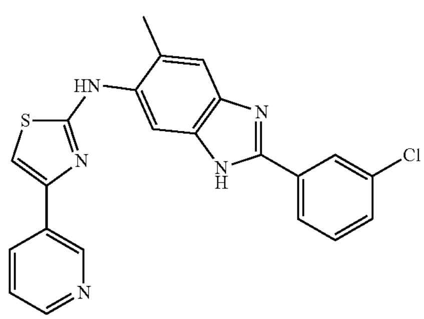 [SMILES: Cc1cc2nc(-c3cccc(Cl)c3)[nH]c2cc1Nc1nc(-c2cccnc2)cs1] | [2-(3-Chloro-phenyl)-6-methyl-3H-benzoimidazol-5-yl]-(4-pyridin-3-yl-thiazol-2-yl)-amine | (ESI-) m/z 416 (M − H)⁻ Retention time = 2.14 mins |
| 033 | 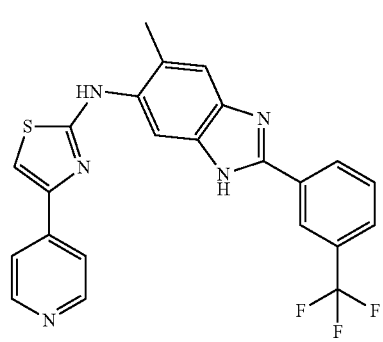 [SMILES: Cc1cc2nc(-c3cccc(C(F)(F)F)c3)[nH]c2cc1Nc1nc(-c2ccncc2)cs1] | [6-Methyl-2-(3-trifluoromethyl-phenyl)-3H-benzoimidazol-5-yl]-(4-pyridin-4-yl-thiazol-2-yl)-amine | (ESI-) m/z 450 (M − H)⁻ Retention time = 2.19 mins |

TABLE 1-continued

| Ex # | Chemical Structure | Name | LCMS |
|------|-------------------|------|------|
| 034 | 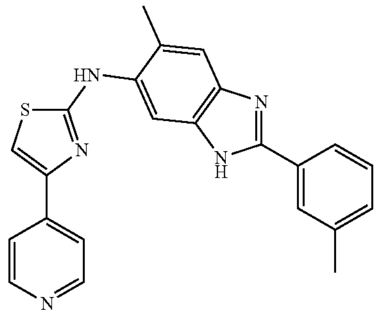 [SMILES: Cc1cccc(-c2nc3cc(C)c(Nc4nc(-c5ccncc5)cs4)cc3[nH]2)c1] | (6-Methyl-2-m-tolyl-3H-benzoimidazol-5-yl)-(4-pyridin-4-yl-thiazol-2-yl)-amine | (ESI-) m/z 396 (M − H)⁻ Retention time = 1.79 mins |
| 035 | 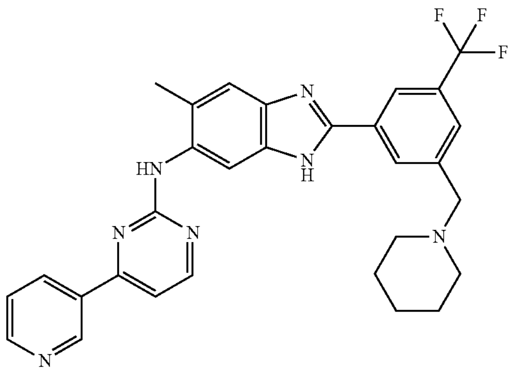 | [6-Methyl-2-(3-piperidin-1-ylmethyl-5-trifluoromethyl-phenyl)-3H-benzoimidazol-5-yl]-(4-pyridin-3-yl-pyrimidin-2-yl)-amine | (ESI-) m/z 542 (M − H)⁻ Retention time = 2.04 mins |
| 036 | 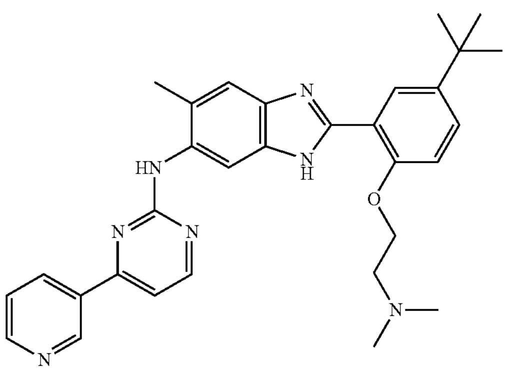 [SMILES: Cc1cc2nc(-c3cc(C(C)(C)C)ccc3OCCN(C)C)[nH]c2cc1Nc1nccc(-c2cccnc2)n1] | {2-[5-tert-Butyl-2-(2-dimethylamino-ethoxy)-phenyl]-6-methyl-3H-benzoimidazol-5-yl}-(4-pyridin-3-yl-pyrimidin-2-yl)-amine | (ESI-) m/z 520 (M − H)⁻ Retention time = 1.97 mins |
| 037 | 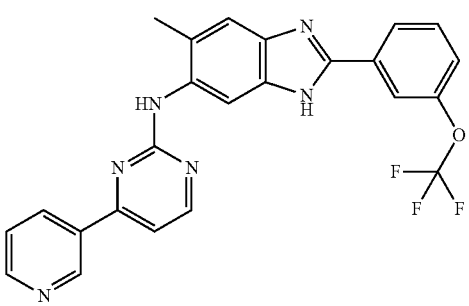 [SMILES: Cc1cc2nc(-c3cccc(OC(F)(F)F)c3)[nH]c2cc1Nc1nccc(-c2cccnc2)n1] | [6-Methyl-2-(3-trifluoromethoxy-phenyl)-3H-benzoimidazol-5-yl]-(4-pyridin-3-yl-pyrimidin-2-yl)-amine | (ESI-) m/z 461 (M − H)⁻ Retention time = 2.43 mins |

TABLE 1-continued

| Ex # | Chemical Structure | Name | LCMS |
|------|-------------------|------|------|
| 038 | 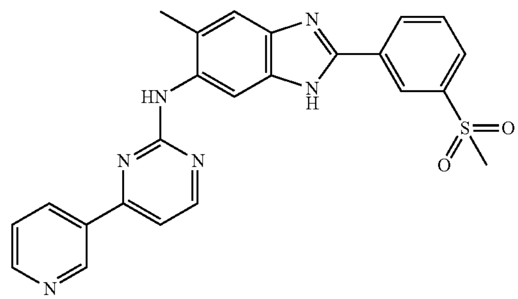 [SMILES: Cc1cc2nc(-c3cccc(S(C)(=O)=O)c3)[nH]c2cc1Nc1nccc(-c2cccnc2)n1] | [2-(3-Methanesulfonyl-phenyl)-6-methyl-3H-benzoimidazol-5-yl]-(4-pyridin-3-yl-pyrimidin-2-yl)-amine | (ESI-) m/z 455 (M − H)⁻ Retention time = 1.87 mins |
| 039 | 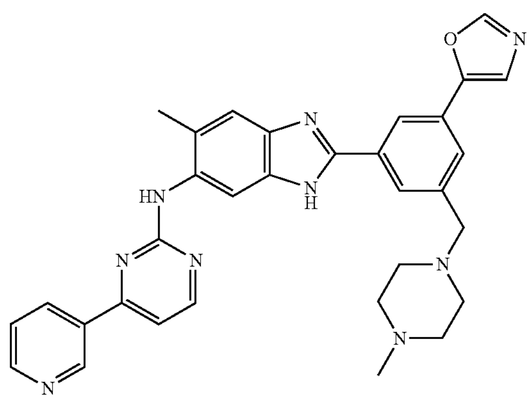 [SMILES: Cc1cc2nc(-c3cc(CN4CCN(C)CC4)cc(-c4cnco4)c3)[nH]c2cc1Nc1nccc(-c2cccnc2)n1] | {6-Methyl-2-[3-(4-methyl-piperazin-1-ylmethyl)-5-oxazol-5-yl-phenyl]-3H-benzoimidazol-5-yl}-(4-pyridin-3-yl-pyrimidin-2-yl)-amine | (ESI-) m/z 556 (M − H)⁻ Retention time = 1.69 mins |
| 040 | 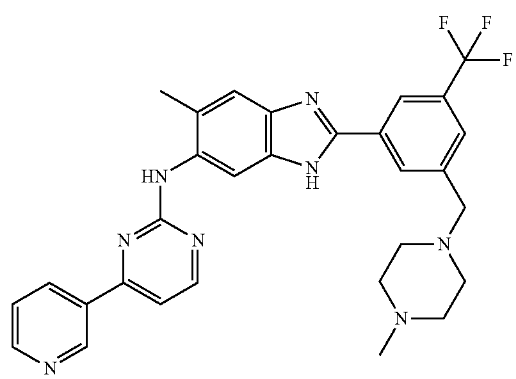 [SMILES: Cc1cc2nc(-c3cc(CN4CCN(C)CC4)cc(C(F)(F)F)c3)[nH]c2cc1Nc1nccc(-c2cccnc2)n1] | {6-Methyl-2-[3-(4-methyl-piperazin-1-ylmethyl)-5-trifluoromethyl-phenyl]-3H-benzoimidazol-5-yl}-(4-pyridin-3-yl-pyrimidin-2-yl)-amine | (ESI-) m/z 557 (M − H)⁻ Retention time = 1.94 mins |
| 041 | 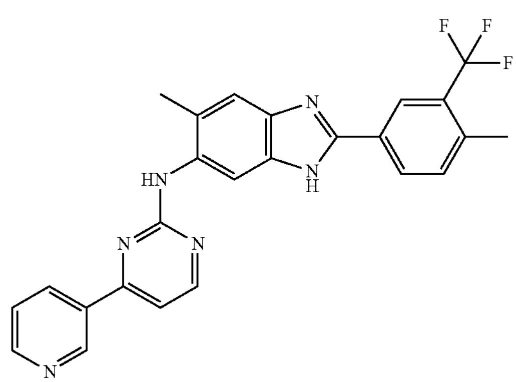 [SMILES: Cc1cc2nc(-c3ccc(C)c(C(F)(F)F)c3)[nH]c2cc1Nc1nccc(-c2cccnc2)n1] | [6-Methyl-2-(4-methyl-3-trifluoromethyl-phenyl)-3H-benzoimidazol-5-yl]-(4-pyridin-3-yl-pyrimidin-2-yl)-amine | (ESI-) m/z 459 (M − H)⁻ Retention time = 2.46 mins |

TABLE 1-continued

| Ex # | Chemical Structure | Name | LCMS |
|---|---|---|---|
| 042 | 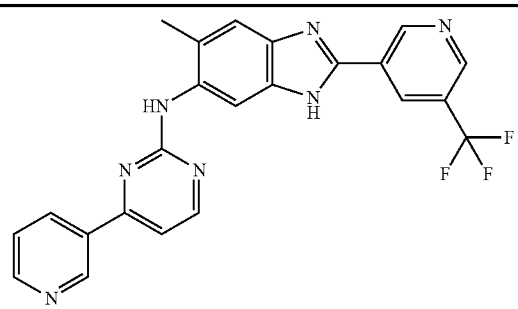 | [6-Methyl-2-(5-trifluoromethyl-pyridin-3-yl)-3H-benzoimidazol-5-yl]-(4-pyridin-3-yl-pyrimidin-2-yl)-amine | (ESI-) m/z 446 (M − H)⁻ Retention time = 2.32 mins |
| 043 | 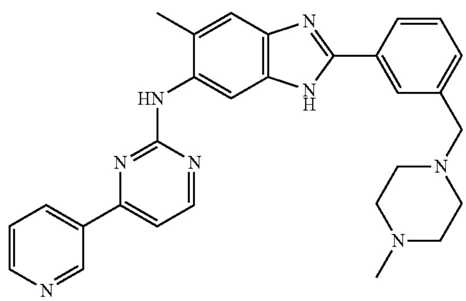 [SMILES: Cc1cc2nc(-c3cccc(CN4CCN(C)CC4)c3)[nH]c2cc1Nc1nccc(-c2cccnc2)n1] | {6-Methyl-2-[3-(4-methyl-piperazin-1-ylmethyl)-phenyl]-3H-benzoimidazol-5-yl}-(4-pyridin-3-yl-pyrimidin-2-yl)-amine | (ESI-) m/z 489 (M − H)⁻ Retention time = 1.53 mins |
| 044 | 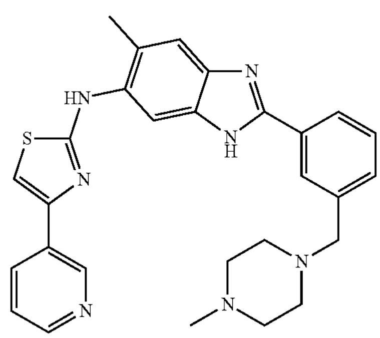 [SMILES: Cc1cc2nc(-c3cccc(CN4CCN(C)CC4)c3)[nH]c2cc1Nc1nc(-c2cccnc2)cs1] | {6-Methyl-2-[3-(4-methyl-piperazin-1-ylmethyl)-phenyl]-1H-benzoimidazol-5-yl}-(4-pyridin-3-yl-thiazol-2-yl)-amine | (ESI-) m/z 494 (M − H)⁻ Retention time = 1.52 mins |
| 045 | 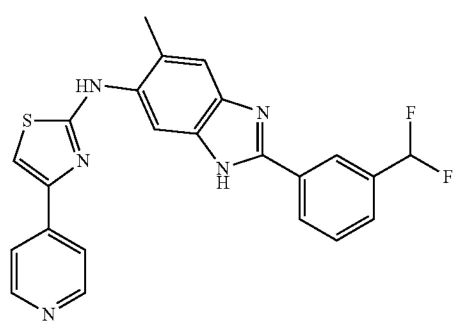 [SMILES: Cc1cc2nc(-c3cccc(C(F)F)c3)[nH]c2cc1Nc1nc(-c2ccncc2)cs1] | [2-(3-Difluoromethyl-phenyl)-6-methyl-3H-benzoimidazol-5-yl]-(4-pyridin-4-yl-thiazol-2-yl)-amine | (ESI-) m/z 432 (M − H)⁻ Retention time = 1.93 mins |
| 046 | 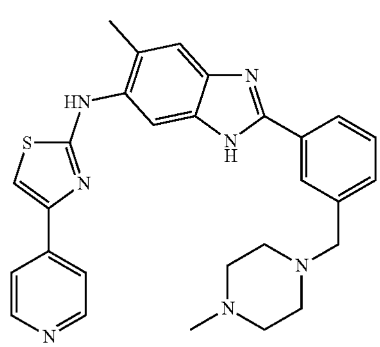 [SMILES: Cc1cc2nc(-c3cccc(CN4CCN(C)CC4)c3)[nH]c2cc1Nc1nc(-c2ccncc2)cs1] | {6-Methyl-2-[3-(4-methyl-piperazin-1-ylmethyl)-phenyl]-1H-benzoimidazol-5-yl}-(4-pyridin-4-yl-thiazol-2-yl)-amine | (ESI-) m/z 494 (M − H)⁻ Retention time = 1.41 mins |

TABLE 1-continued

| Ex # | Chemical Structure | Name | LCMS |
|---|---|---|---|
| 047 | 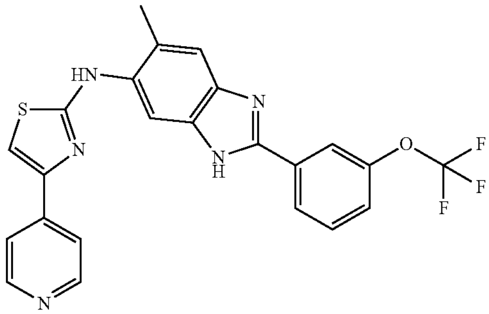 [SMILES: Cc1cc2nc(-c3cccc(OC(F)(F)F)c3)[nH]c2cc1Nc1nc(-c2ccncc2)cs1] | [6-Methyl-2-(3-trifluoromethoxy-phenyl)-3H-benzoimidazol-5-yl]-(4-pyridin-4-yl-thiazol-2-yl)-amine | (ESI-) m/z 466 (M − H)⁻ Retention time = 2.25 mins |
| 048 | 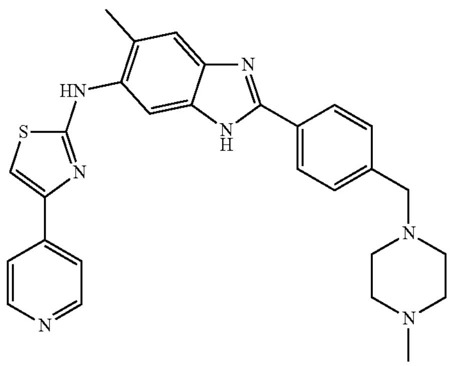 [SMILES: Cc1cc2nc(-c3ccc(CN4CCN(C)CC4)cc3)[nH]c2cc1Nc1nc(-c2ccncc2)cs1] | {6-Methyl-2-[4-(4-methyl-piperazin-1-ylmethyl)-phenyl]-1H-benzoimidazol-5-yl}-(4-pyridin-4-yl-thiazol-2-yl)-amine | (ESI-) m/z 494 (M − H)⁻ Retention time = 1.39 mins |
| 049 | 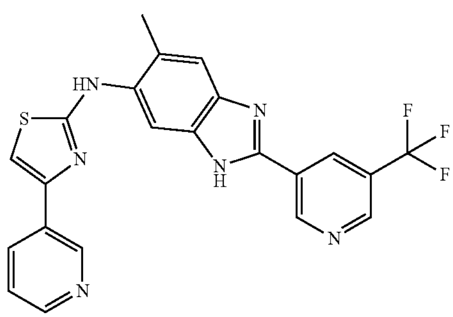 [SMILES: Cc1cc2nc(-c3cncc(C(F)(F)F)c3)[nH]c2cc1Nc1nc(-c2cccnc2)cs1] | [6-Methyl-2-(5-trifluoromethyl-pyridin-3-yl)-3H-benzoimidazol-5-yl]-(4-pyridin-3-yl-thiazol-2-yl)-amine | (ESI-) m/z 451 (M − H)⁻ Retention time = 2.28 mins |
| 050 | 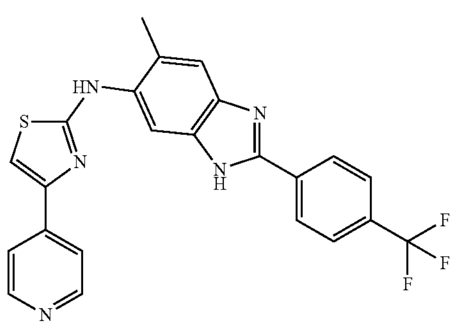 [SMILES: Cc1cc2nc(-c3ccc(C(F)(F)F)cc3)[nH]c2cc1Nc1nc(-c2ccncc2)cs1] | [6-Methyl-2-(4-trifluoromethyl-phenyl)-3H-benzoimidazol-5-yl]-(4-pyridin-4-yl-thiazol-2-yl)-amine | (ESI-) m/z 450 (M − H)⁻ Retention time = 2.21 mins |

TABLE 1-continued

| Ex # | Chemical Structure | Name | LCMS |
|------|-------------------|------|------|
| 051 | 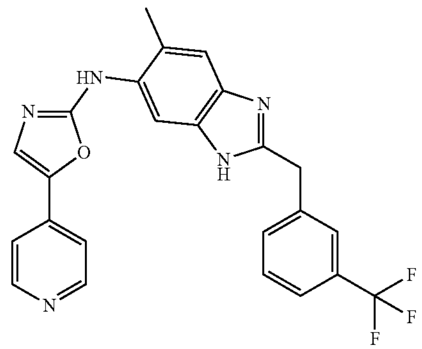 [SMILES: Cc1cc2nc(Cc3cccc(C(F)(F)F)c3)[nH]c2cc1Nc1ncc(-c2ccncc2)o1] | [6-Methyl-2-(3-trifluoromethyl-benzyl)-3H-benzoimidazol-5-yl]-(5-pyridin-4-yl-oxazol-2-yl)-amine | (ESI-) m/z 448 (M − H)⁻ Retention time = 1.82 mins |
| 052 | 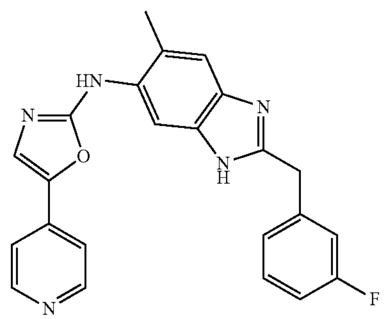 [SMILES: Cc1cc2nc(Cc3cccc(F)c3)[nH]c2cc1Nc1ncc(-c2ccncc2)o1] | [2-(3-Fluoro-benzyl)-6-methyl-3H-benzoimidazol-5-yl]-(5-pyridin-4-yl-oxazol-2-yl)-amine | (ESI-) m/z 398 (M − H)⁻ Retention time = 1.55 mins |
| 053 | 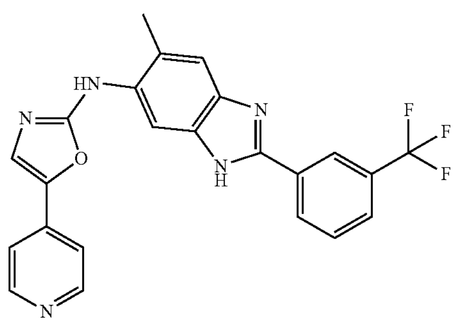 [SMILES: Cc1cc2nc(-c3cccc(C(F)(F)F)c3)[nH]c2cc1Nc1ncc(-c2ccncc2)o1] | [6-Methyl-2-(3-trifluoromethyl-phenyl)-3H-benzoimidazol-5-yl]-(5-pyridin-4-yl-oxazol-2-yl)-amine | (ESI-) m/z 434 (M − H)⁻ Retention time = 2.01 mins |
| 054 | 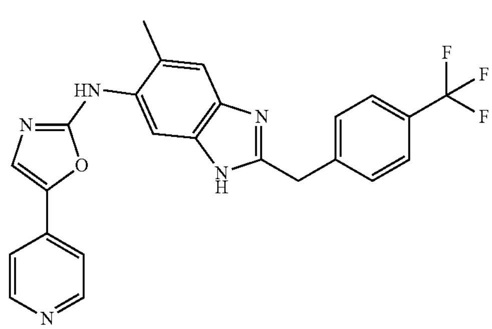 [SMILES: Cc1cc2nc(Cc3ccc(C(F)(F)F)cc3)[nH]c2cc1Nc1ncc(-c2ccncc2)o1] | [6-Methyl-2-(4-trifluoromethyl-benzyl)-3H-benzoimidazol-5-yl]-(5-pyridin-4-yl-oxazol-2-yl)-amine | (ESI-) m/z 448 (M − H)⁻ Retention time = 1.85 mins |

TABLE 1-continued

| Ex # | Name | LCMS |
|---|---|---|
| 055 | (6-Methyl-2-morpholin-4-ylmethyl-3H-benzoimidazol-5-yl)-(5-pyridin-4-yl-oxazol-2-yl)-amine | (ESI-) m/z 389 (M − H)⁻ Retention time = 1.17 mins |
| 056 | [6-Methyl-2-(4-methyl-3-trifluoromethyl-phenyl)-3H-benzoimidazol-5-yl]-(4-pyridin-3-yl-thiazol-2-yl)-amine | (ESI-) m/z 464 (M − H)⁻ Retention time = 2.46 mins |
| 057 | [6-Methyl-2-(4-pyrazol-1-yl-phenyl)-3H-benzoimidazol-5-yl]-(4-pyridin-3-yl-thiazol-2-yl)-amine | (ESI-) m/z 448 (M − H)⁻ Retention time = 1.96 mins |
| 058 | [2-(3-Fluoro-5-trifluoromethyl-phenyl)-6-methyl-3H-benzoimidazol-5-yl]-(4-pyridin-3-yl-thiazol-2-yl)-amine | (ESI-) m/z 468 (M − H)⁻ Retention time = 2.70 mins |
| 059 | [2-(4-Chloro-phenyl)-6-methyl-1H-benzoimidazol-5-yl]-(4-pyridin-3-yl-thiazol-2-yl)-amine | (ESI-) m/z 416 (M − H)⁻ Retention time = 2.08 mins |

TABLE 1-continued

| Ex # | Chemical Structure | Name | LCMS |
|---|---|---|---|
| 060 | 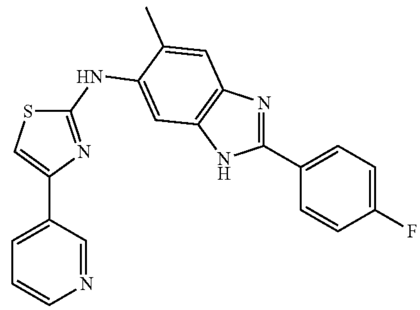 [SMILES: Cc1cc2nc(-c3ccc(F)cc3)[nH]c2cc1Nc1nc(-c2cccnc2)cs1] | [2-(4-Fluoro-phenyl)-6-methyl-1H-benzoimidazol-5-yl]-(4-pyridin-3-yl-thiazol-2-yl)-amine | (ESI-) m/z 400 (M − H)⁻ Retention time = 1.89 mins |
| 061 | 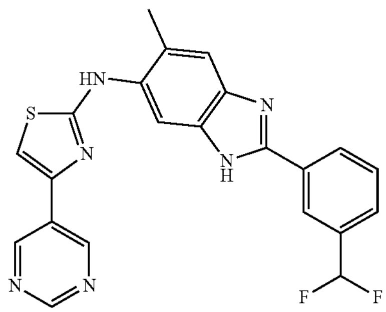 [SMILES: Cc1cc2nc(-c3cccc(C(F)F)c3)[nH]c2cc1Nc1nc(-c2cncnc2)cs1] | [2-(3-Difluoromethyl-phenyl)-6-methyl-3H-benzoimidazol-5-yl]-(4-pyrimidin-5-yl-thiazol-2-yl)-amine | (ESI-) m/z 433 (M − H)⁻ Retention time = 2.31 mins |
| 062 | 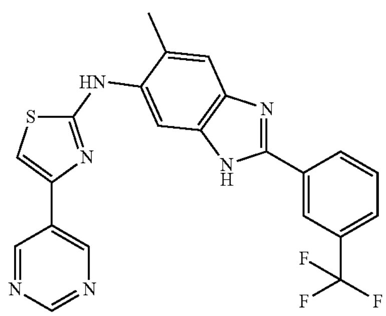 [SMILES: Cc1cc2nc(-c3cccc(C(F)(F)F)c3)[nH]c2cc1Nc1nc(-c2cncnc2)cs1] | [6-Methyl-2-(3-trifluoromethyl-phenyl)-3H-benzoimidazol-5-yl]-(4-pyrimidin-5-yl-thiazol-2-yl)-amine | (ESI-) m/z 451 (M − H)⁻ Retention time = 2.62 mins |
| 063 | 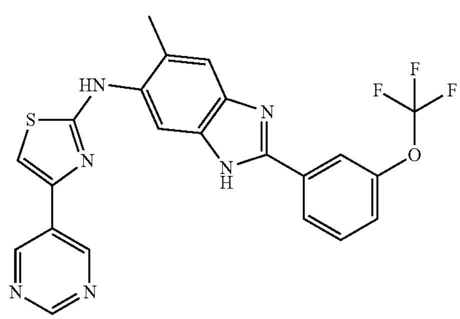 [SMILES: Cc1cc2nc(-c3cccc(OC(F)(F)F)c3)[nH]c2cc1Nc1nc(-c2cncnc2)cs1] | [6-Methyl-2-(3-trifluoromethoxy-phenyl)-3H-benzoimidazol-5-yl]-(4-pyrimidin-5-yl-thiazol-2-yl)-amine | (ESI-) m/z 467 (M − H)⁻ Retention time = 2.67 mins |
| 064 | 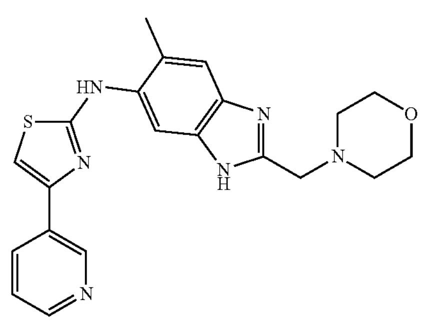 [SMILES: Cc1cc2nc(CN3CCOCC3)[nH]c2cc1Nc1nc(-c2cccnc2)cs1] | (6-Methyl-2-morpholin-4-ylmethyl-3H-benzoimidazol-5-yl)-(4-pyridin-3-yl-thiazol-2-yl)-amine | (ESI-) m/z 405 (M − H)⁻ Retention time = 1.45 mins |

TABLE 1-continued

| Ex # | Chemical Structure | Name | LCMS |
|---|---|---|---|
| 065 | 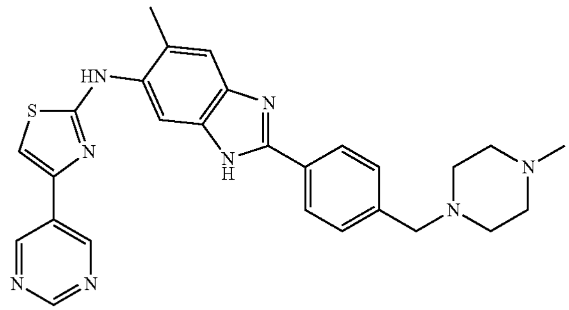 [SMILES: Cc1cc2nc(-c3ccc(CN4CCN(C)CC4)cc3)[nH]c2cc1Nc1nc(-c2cncnc2)cs1] | {6-Methyl-2-[4-(4-methyl-piperazin-1-ylmethyl)-phenyl]-3H-benzoimidazol-5-yl}-(4-pyrimidin-5-yl-thiazol-2-yl)-amine | (ESI-) m/z 495 (M − H)⁻ Retention time = 1.66 mins |
| 066 | 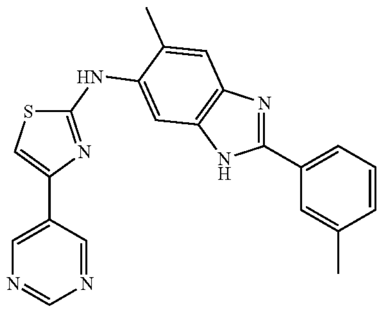 [SMILES: Cc1cccc(-c2nc3cc(C)c(Nc4nc(-c5cncnc5)cs4)cc3[nH]2)c1] | (6-Methyl-2-m-tolyl-1H-benzoimidazol-5-yl)-(4-pyrimidin-5-yl-thiazol-2-yl)-amine | (ESI-) m/z 397 (M − H)⁻ Retention time = 2.21 mins |
| 067 | 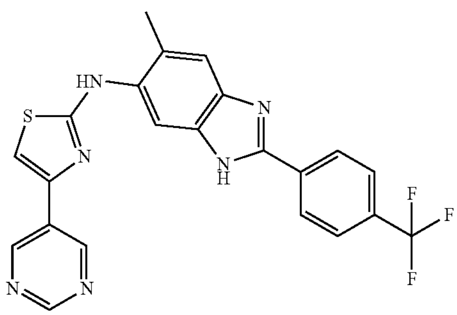 [SMILES: Cc1cc2nc(-c3ccc(C(F)(F)F)cc3)[nH]c2cc1Nc1nc(-c2cncnc2)cs1] | [6-Methyl-2-(4-trifluoromethyl-phenyl)-1H-benzoimidazol-5-yl]-(4-pyrimidin-5-yl-thiazol-2-yl)-amine | (ESI-) m/z 451 (M − H)⁻ Retention time = 2.62 mins |
| 068 | 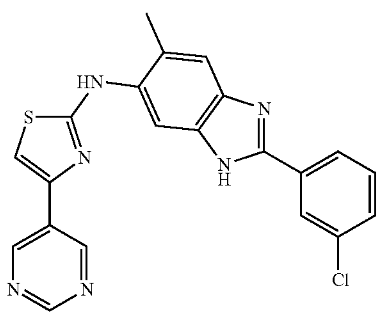 [SMILES: Cc1cc2nc(-c3cccc(Cl)c3)[nH]c2cc1Nc1nc(-c2cncnc2)cs1] | [2-(3-Chloro-phenyl)-6-methyl-1H-benzoimidazol-5-yl]-(4-pyrimidin-5-yl-thiazol-2-yl)-amine | (ESI-) m/z 417 (M − H)⁻ Retention time = 2.39 mins |
| 069 | 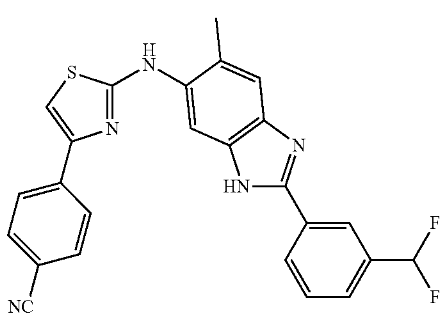 [SMILES: Cc1cc2nc(-c3cccc(C(F)F)c3)[nH]c2cc1Nc1nc(-c2ccc(C#N)cc2)cs1] | 4-{2-[2-(3-Difluoromethyl-phenyl)-6-methyl-3H-benzoimidazol-5-ylamino]-thiazol-4-yl}-benzonitrile | (ESI-) m/z 456 (M − H)⁻ Retention time = 2.90 mins |

TABLE 1-continued

| Ex # | Chemical Structure | Name | LCMS |
|---|---|---|---|
| 070 | 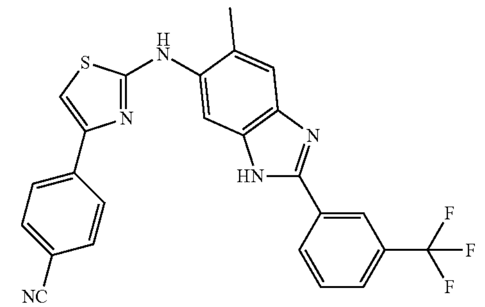 [SMILES: Cc1cc2nc(-c3cccc(C(F)(F)F)c3)[nH]c2cc1Nc1nc(-c2ccc(C#N)cc2)cs1] | 4-{2-[6-Methyl-2-(3-trifluoromethyl-phenyl)-3H-benzoimidazol-5-ylamino]-thiazol-4-yl}-benzonitrile | (ESI-) m/z 474 (M − H)⁻ Retention time = 3.25 mins |
| 071 | 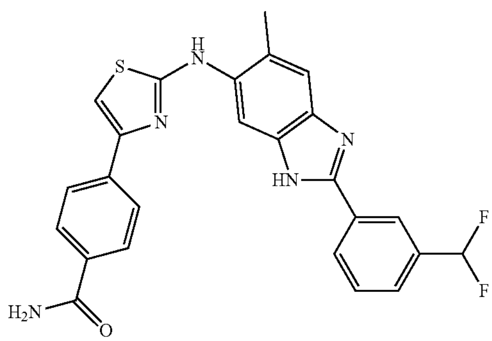 [SMILES: Cc1cc2nc(-c3cccc(C(F)F)c3)[nH]c2cc1Nc1nc(-c2ccc(C(N)=O)cc2)cs1] | 4-{2-[2-(3-Difluoromethyl-phenyl)-6-methyl-3H-benzoimidazol-5-ylamino]-thiazol-4-yl}-benzamide | (ESI-) m/z 474 (M − H)⁻ Retention time = 2.34 mins |
| 072 | 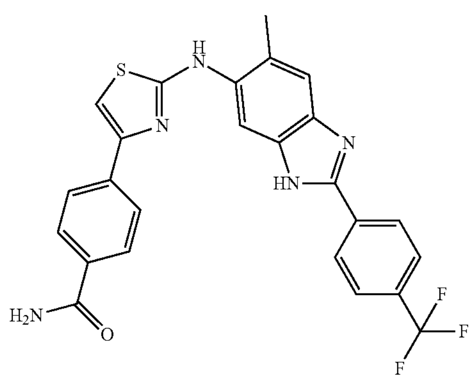 [SMILES: Cc1cc2nc(-c3ccc(C(F)(F)F)cc3)[nH]c2cc1Nc1nc(-c2ccc(C(N)=O)cc2)cs1] | 4-{2-[6-Methyl-2-(4-trifluoromethyl-phenyl)-3H-benzoimidazol-5-ylamino]-thiazol-4-yl}-benzamide | (ESI-) m/z 492 (M − H)⁻ Retention time = 2.64 mins |
| 073 | 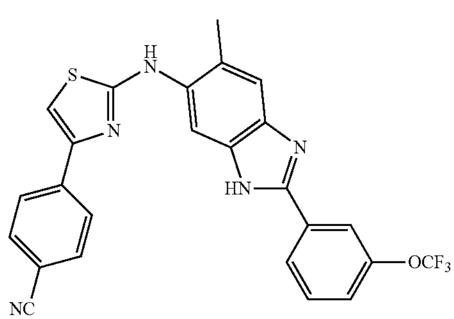 | 4-{2-[6-Methyl-2-(3-trifluoromethoxy-phenyl)-3H-benzoimidazol-5-ylamino]-thiazol-4-yl}-benzamide | (ESI-) m/z 508 (M − H)⁻ Retention time = 2.67 mins |

TABLE 1-continued

| Ex # | Chemical Structure | Name | LCMS |
|---|---|---|---|
| 074 | 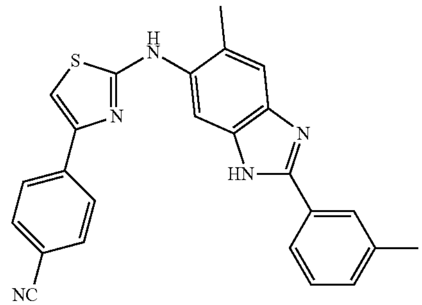 [SMILES: Cc1cccc(-c2nc3cc(C)c(Nc4nc(-c5ccc(C#N)cc5)cs4)cc3[nH]2)c1] | 4-[2-(6-Methyl-2-m-tolyl-3H-benzoimidazol-5-ylamino)-thiazol-4-yl]-benzonitrile | (ESI-) m/z 420 (M − H)⁻ Retention time = 2.75 mins |
| 075 | 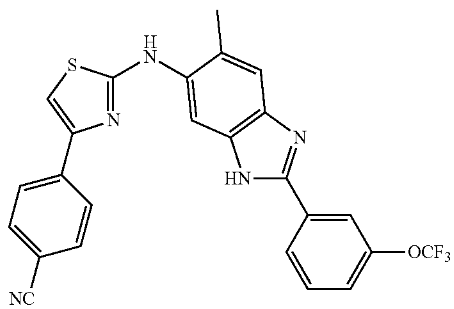 [SMILES: Cc1cc2nc(-c3cccc(OC(F)(F)F)c3)[nH]c2cc1Nc1nc(-c2ccc(C#N)cc2)cs1] | 4-{2-[6-Methyl-2-(3-trifluoromethoxy-phenyl)-3H-benzoimidazol-5-ylamino]-thiazol-4-yl}-benzonitrile | (ESI-) m/z 490 (M − H)⁻ Retention time = 3.28 mins |
| 076 | 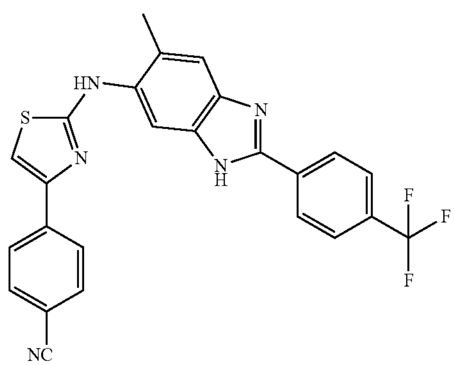 [SMILES: Cc1cc2nc(-c3ccc(C(F)(F)F)cc3)[nH]c2cc1Nc1nc(-c2ccc(C#N)cc2)cs1] | 4-{2-[6-Methyl-2-(4-trifluoromethyl-phenyl)-3H-benzoimidazol-5-ylamino]-thiazol-4-yl}-benzonitrile | (ESI-) m/z 474 (M − H)⁻ Retention time = 3.25 mins |
| 077 | 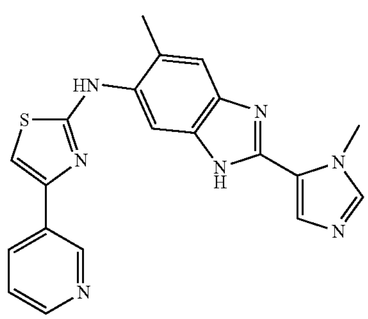 [SMILES: Cc1cc2nc(-c3cncn3C)[nH]c2cc1Nc1nc(-c2cccnc2)cs1] | [6-Methyl-2-(3-methyl-3H-imidazol-4-yl)-3H-benzoimidazol-5-yl]-(4-pyridin-3-yl-thiazol-2-yl)-amine | (ESI-) m/z 386 (M − H)⁻ Retention time = 1.50 mins |
| 078 | 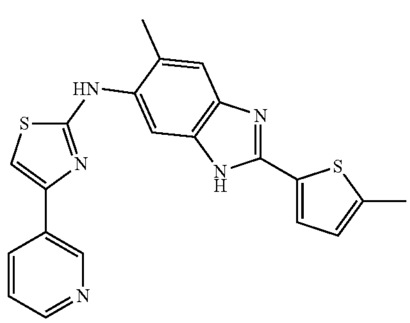 [SMILES: Cc1ccc(-c2nc3cc(C)c(Nc4nc(-c5cccnc5)cs4)cc3[nH]2)s1] | [6-Methyl-2-(5-methyl-thiophen-2-yl)-3H-benzoimidazol-5-yl]-(4-pyridin-3-yl-thiazol-2-yl)-amine | (ESI-) m/z 402 (M − H)⁻ Retention time = 2.04 mins |

TABLE 1-continued

| Ex # | Chemical Structure | Name | LCMS |
|---|---|---|---|
| 079 | 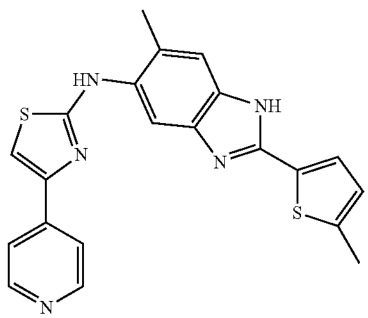 [SMILES: Cc1ccc(-c2nc3cc(Nc4nc(-c5ccncc5)cs4)c(C)cc3[nH]2)s1] | [6-Methyl-2-(5-methyl-thiophen-2-yl)-1H-benzoimidazol-5-yl]-(4-pyridin-4-yl-thiazol-2-yl)-amine | (ESI-) m/z 402 (M − H)⁻ Retention time = 1.86 mins |
| 080 | 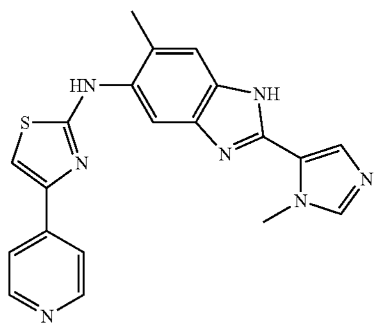 [SMILES: Cc1cc2[nH]c(-c3cncn3C)nc2cc1Nc1nc(-c2ccncc2)cs1] | [6-Methyl-2-(3-methyl-3H-imidazol-4-yl)-1H-benzoimidazol-5-yl]-(4-pyridin-4-yl-thiazol-2-yl)-amine | (ESI-) m/z 386 (M − H)⁻ Retention time = 1.48 mins |
| 081 | 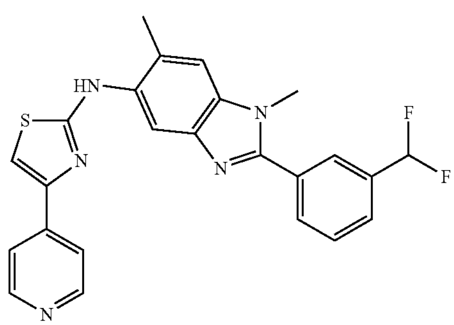 [SMILES: Cc1cc2c(cc1Nc1nc(-c3ccncc3)cs1)nc(-c1cccc(C(F)F)c1)n2C] | [2-(3-Difluoromethyl-phenyl)-1,6-dimethyl-1H-benzoimidazol-5-yl]-(4-pyridin-4-yl-thiazol-2-yl)-amine | (ESI-) m/z 446 (M − H)⁻ Retention time = 2.08 mins |
| 082 | 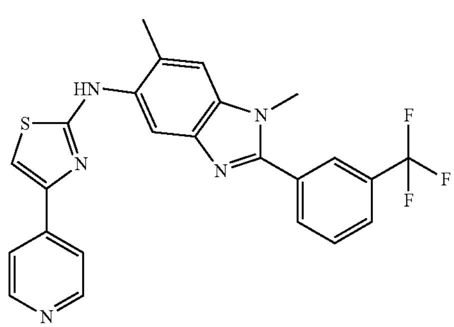 [SMILES: Cc1cc2c(cc1Nc1nc(-c3ccncc3)cs1)nc(-c1cccc(C(F)(F)F)c1)n2C] | [1,6-Dimethyl-2-(3-trifluoromethyl-phenyl)-1H-benzoimidazol-5-yl]-(4-pyridin-4-yl-thiazol-2-yl)-amine | (ESI-) m/z 464 (M − H)⁻ Retention time = 2.36 mins |

TABLE 1-continued

| Ex # | Chemical Structure | Name | LCMS |
|------|-------------------|------|------|
| 083 | 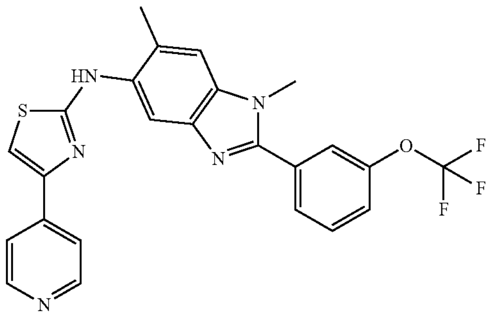 [SMILES: Cc1cc2c(cc1Nc1nc(-c3ccncc3)cs1)nc(-c1cccc(OC(F)(F)F)c1)n2C] | [1,6-Dimethyl-2-(3-trifluoromethoxy-phenyl)-1H-benzoimidazol-5-yl]-(4-pyridin-4-yl-thiazol-2-yl)-amine | (ESI-) m/z 480 (M − H)⁻ Retention time = 2.41 mins |
| 084 | 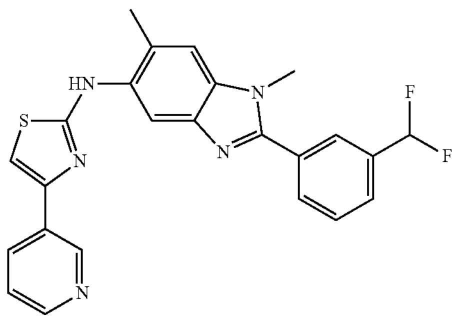 [SMILES: Cc1cc2c(cc1Nc1nc(-c3cccnc3)cs1)nc(-c1cccc(C(F)F)c1)n2C] | [2-(3-Difluoromethyl-phenyl)-1,6-dimethyl-1H-benzoimidazol-5-yl]-(4-pyridin-3-yl-thiazol-2-yl)-amine | (ESI-) m/z 446 (M − H)⁻ Retention time = 2.23 mins |
| 085 | 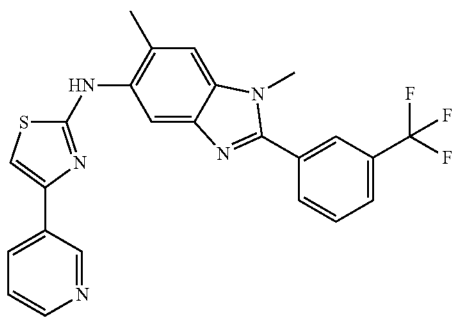 [SMILES: Cc1cc2c(cc1Nc1nc(-c3cccnc3)cs1)nc(-c1cccc(C(F)(F)F)c1)n2C] | [1,6-Dimethyl-2-(3-trifluoromethyl-phenyl)-1H-benzoimidazol-5-yl]-(4-pyridin-3-yl-thiazol-2-yl)-amine | (ESI-) m/z 464 (M − H)⁻ Retention time = 2.52 mins |
| 086 | 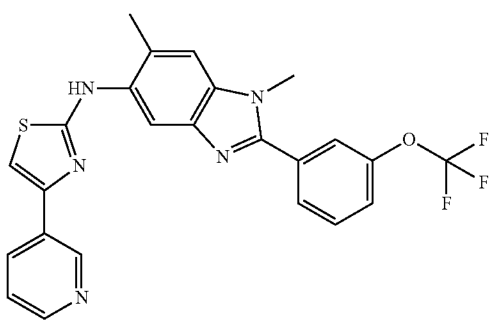 [SMILES: Cc1cc2c(cc1Nc1nc(-c3cccnc3)cs1)nc(-c1cccc(OC(F)(F)F)c1)n2C] | [1,6-Dimethyl-2-(3-trifluoromethoxy-phenyl)-1H-benzoimidazol-5-yl]-(4-pyridin-3-yl-thiazol-2-yl)-amine | (ESI-) m/z 480 (M − H)⁻ Retention time = 2.60 mins |
| 087 | 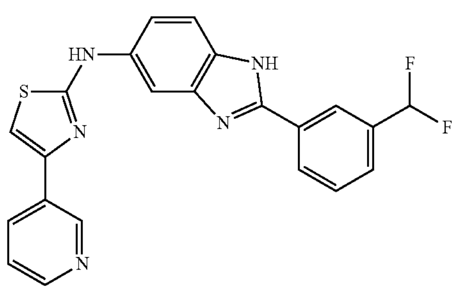 [SMILES: FC(F)c1cccc(-c2nc3cc(Nc4nc(-c5cccnc5)cs4)ccc3[nH]2)c1] | [2-(3-Difluoromethyl-phenyl)-1H-benzoimidazol-5-yl]-(4-pyridin-3-yl-thiazol-2-yl)-amine | (ESI-) m/z 418 (M − H)⁻ Retention time = 2.12 mins |

TABLE 1-continued

| Ex # | Chemical Structure | Name | LCMS |
|---|---|---|---|
| 088 | 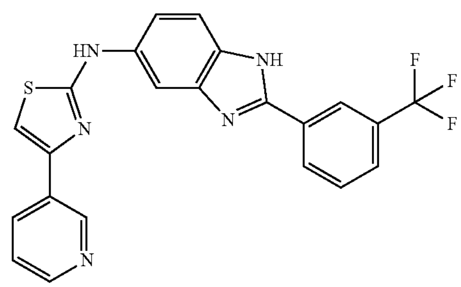 [SMILES: FC(F)(F)c1cccc(-c2nc3cc(Nc4nc(-c5cccnc5)cs4)ccc3[nH]2)c1] | (4-Pyridin-3-yl-thiazol-2-yl)-[2-(3-trifluoromethyl-phenyl)-1H-benzoimidazol-5-yl]-amine | (ESI-) m/z 436 (M − H)⁻ Retention time = 2.44 mins |
| 089 | 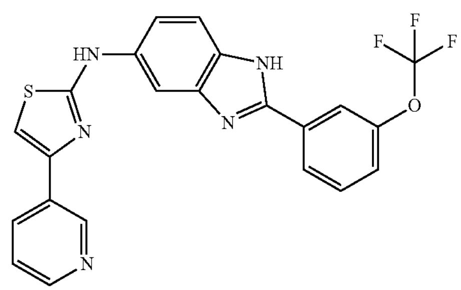 [SMILES: FC(F)(F)Oc1cccc(-c2nc3cc(Nc4nc(-c5cccnc5)cs4)ccc3[nH]2)c1] | (4-Pyridin-3-yl-thiazol-2-yl)-[2-(3-trifluoromethoxy-phenyl)-1H-benzoimidazol-5-yl]-amine | (ESI-) m/z 452 (M − H)⁻ Retention time = 2.50 mins |
| 090 | 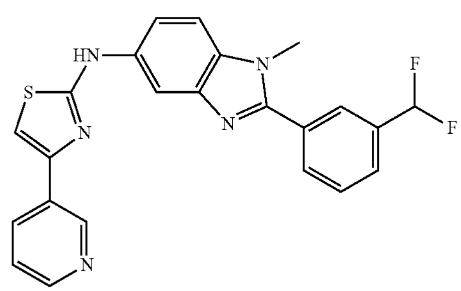 [SMILES: Cn1c(-c2cccc(C(F)F)c2)nc2cc(Nc3nc(-c4cccnc4)cs3)ccc21] | [2-(3-Difluoromethyl-phenyl)-1-methyl-1H-benzoimidazol-5-yl]-(4-pyridin-3-yl-thiazol-2-yl)-amine | (ESI-) m/z 432 (M − H)⁻ Retention time = 2.11 mins |
| 091 | 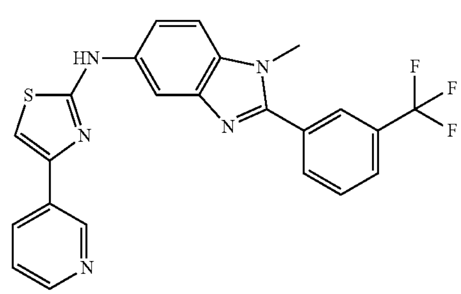 [SMILES: Cn1c(-c2cccc(C(F)(F)F)c2)nc2cc(Nc3nc(-c4cccnc4)cs3)ccc21] | [1-Methyl-2-(3-trifluoromethyl-phenyl)-1H-benzoimidazol-5-yl]-(4-pyridin-3-yl-thiazol-2-yl)-amine | (ESI-) m/z 450 (M − H)⁻ Retention time = 2.39 mins |
| 092 | 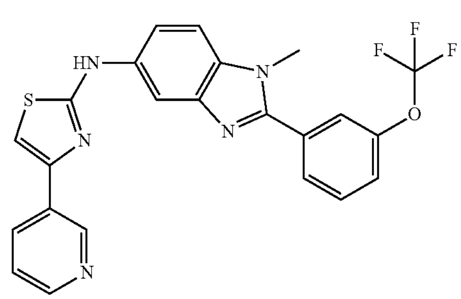 [SMILES: Cn1c(-c2cccc(OC(F)(F)F)c2)nc2cc(Nc3nc(-c4cccnc4)cs3)ccc21] | [1-Methyl-2-(3-trifluoromethoxy-phenyl)-1H-benzoimidazol-5-yl]-(4-pyridin-3-yl-thiazol-2-yl)-amine | (ESI-) m/z 466 (M − H)⁻ Retention time = 2.47 mins |

TABLE 1-continued

| Ex # | Chemical Structure | Name | LCMS |
|---|---|---|---|
| 093 | 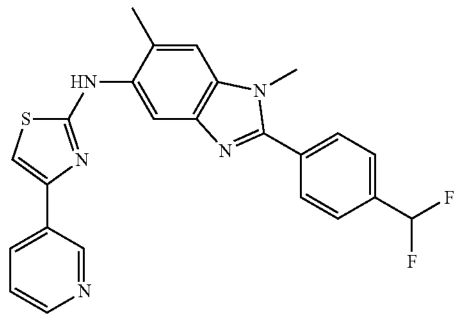 [SMILES: Cc1cc2c(cc1Nc1nc(-c3cccnc3)cs1)nc(-c1ccc(C(F)F)cc1)n2C] | [2-(4-Difluoromethyl-phenyl)-1,6-dimethyl-1H-benzoimidazol-5-yl]-(4-pyridin-3-yl-thiazol-2-yl)-amine | (ESI-) m/z 446 (M − H)$^-$ Retention time = 2.25 mins |
| 094 | 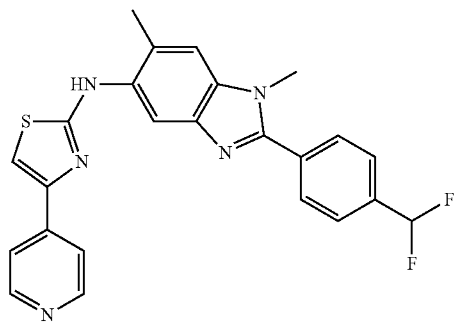 [SMILES: Cc1cc2c(cc1Nc1nc(-c3ccncc3)cs1)nc(-c1ccc(C(F)F)cc1)n2C] | [2-(4-Difluoromethyl-phenyl)-1,6-dimethyl-1H-benzoimidazol-5-yl]-(4-pyridin-4-yl-thiazol-2-yl)-amine | (ESI-) m/z 446 (M − H)$^-$ Retention time = 2.08 mins |
| 095 | 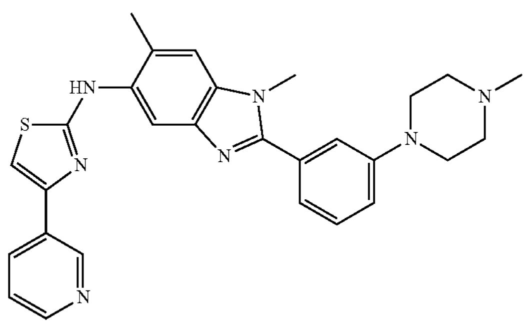 [SMILES: Cc1cc2c(cc1Nc1nc(-c3cccnc3)cs1)nc(-c1cccc(N3CCN(C)CC3)c1)n2C] | {1,6-Dimethyl-2-[3-(4-methyl-piperazin-1-yl)-phenyl]-1H-benzoimidazol-5-yl}-(4-pyridin-3-yl-thiazol-2-yl)-amine | (ESI-) m/z 494 (M − H)$^-$ Retention time = 1.62 mins |
| 096 | 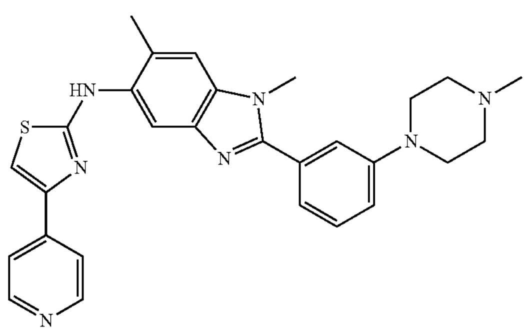 [SMILES: Cc1cc2c(cc1Nc1nc(-c3ccncc3)cs1)nc(-c1cccc(N3CCN(C)CC3)c1)n2C] | {1,6-Dimethyl-2-[3-(4-methyl-piperazin-1-yl)-phenyl]-1H-benzoimidazol-5-yl}-(4-pyridin-4-yl-thiazol-2-yl)-amine | (ESI-) m/z 494 (M − H)$^-$ Retention time = 1.51 mins |
| 097 | 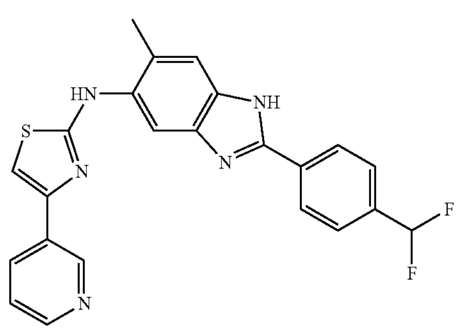 [SMILES: Cc1cc2[nH]c(-c3ccc(C(F)F)cc3)nc2cc1Nc1nc(-c2cccnc2)cs1] | [2-(4-Difluoromethyl-phenyl)-6-methyl-1H-benzoimidazol-5-yl]-(4-pyridin-3-yl-thiazol-2-yl)-amine | (ESI-) m/z 432 (M − H)$^-$ Retention time = 2.20 mins |

TABLE 1-continued

| Ex # | Chemical Structure | Name | LCMS |
|---|---|---|---|
| 098 | 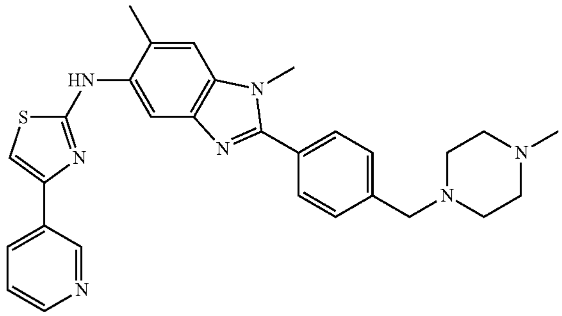 [SMILES: Cc1cc2c(cc1Nc1nc(-c3cccnc3)cs1)nc(-c1ccc(CN3CCN(C)CC3)cc1)n2C] | {1,6-Dimethyl-2-[4-(4-methyl-piperazin-1-ylmethyl)-phenyl]-1H-benzoimidazol-5-yl}-(4-pyridin-3-yl-thiazol-2-yl)-amine | (ESI-) m/z 508 (M − H)⁻ Retention time = 1.58 mins |
| 099 | 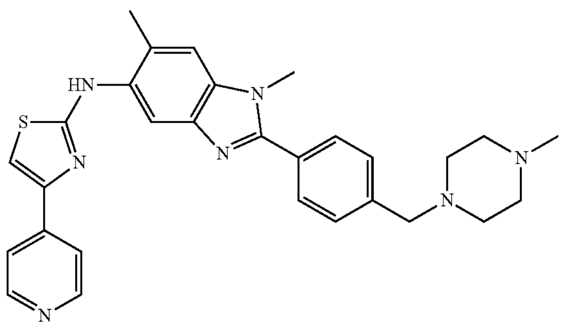 [SMILES: Cc1cc2c(cc1Nc1nc(-c3ccncc3)cs1)nc(-c1ccc(CN3CCN(C)CC3)cc1)n2C] | {1,6-Dimethyl-2-[4-(4-methyl-piperazin-1-ylmethyl)-phenyl]-1H-benzoimidazol-5-yl}-(4-pyridin-4-yl-thiazol-2-yl)-amine | (ESI-) m/z 508 (M − H)⁻ Retention time = 1.47 mins |
| 100 | 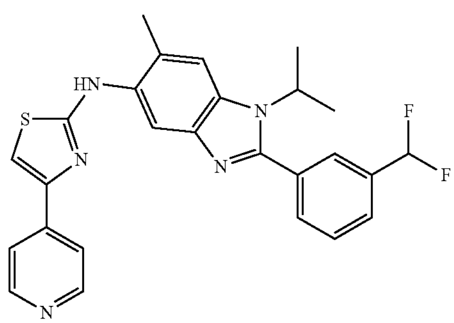 [SMILES: Cc1cc2c(cc1Nc1nc(-c3ccncc3)cs1)nc(-c1cccc(C(F)F)c1)n2C(C)C] | [2-(3-Difluoromethyl-phenyl)-1-isopropyl-6-methyl-1H-benzoimidazol-5-yl]-(4-pyridin-4-yl-thiazol-2-yl)-amine | (ESI-) m/z 474 (M − H)⁻ Retention time = 2.32 mins |
| 101 | 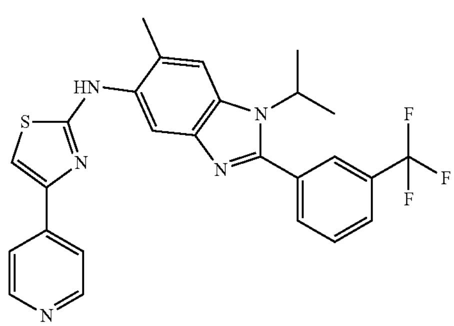 [SMILES: Cc1cc2c(cc1Nc1nc(-c3ccncc3)cs1)nc(-c1cccc(C(F)(F)F)c1)n2C(C)C] | [1-Isopropyl-6-methyl-2-(3-trifluoromethyl-phenyl)-1H-benzoimidazol-5-yl]-(4-pyridin-4-yl-thiazol-2-yl)-amine | (ESI-) m/z 492 (M − H)⁻ Retention time = 2.59 mins |

TABLE 1-continued

| Ex # | Chemical Structure | Name | LCMS |
|---|---|---|---|
| 102 | 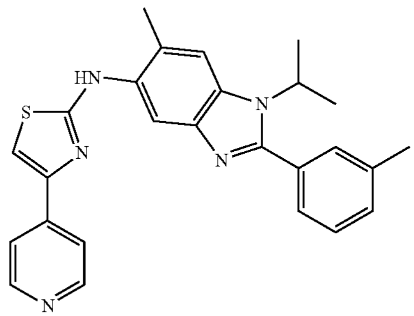 [SMILES: Cc1cccc(-c2nc3cc(Nc4nc(-c5ccncc5)cs4)c(C)cc3n2C(C)C)c1] | (1-Isopropyl-6-methyl-2-m-tolyl-1H-benzoimidazol-5-yl)-(4-pyridin-4-yl-thiazol-2-yl)-amine | (ESI-) m/z 438 (M − H)⁻ Retention time = 2.19 mins |
| 103 | 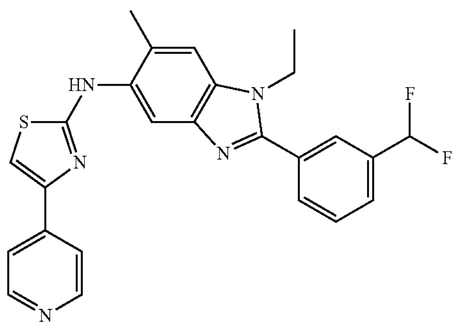 [SMILES: CCn1c(-c2cccc(C(F)F)c2)nc2cc(Nc3nc(-c4ccncc4)cs3)c(C)cc21] | [2-(3-Difluoromethyl-phenyl)-1-ethyl-6-methyl-1H-benzoimidazol-5-yl]-(4-pyridin-4-yl-thiazol-2-yl)-amine | (ESI-) m/z 460 (M − H)⁻ Retention time = 2.22 mins |
| 104 | 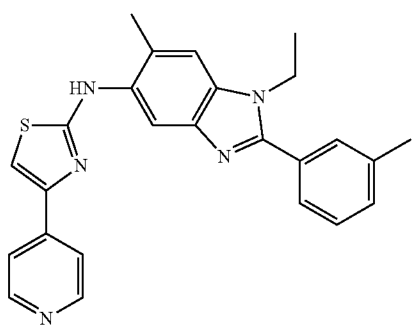 [SMILES: CCn1c(-c2cccc(C)c2)nc2cc(Nc3nc(-c4ccncc4)cs3)c(C)cc21] | (1-Ethyl-6-methyl-2-m-tolyl-1H-benzoimidazol-5-yl)-(4-pyridin-4-yl-thiazol-2-yl)-amine | (ESI-) m/z 424 (M − H)⁻ Retention time = 2.09 mins |
| 105 | 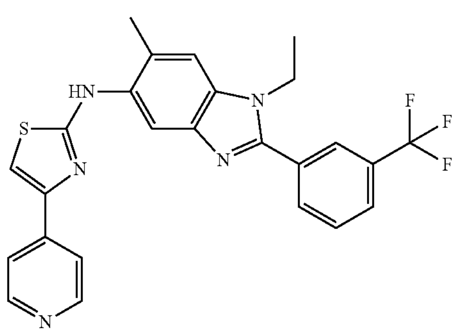 [SMILES: CCn1c(-c2cccc(C(F)(F)F)c2)nc2cc(Nc3nc(-c4ccncc4)cs3)c(C)cc21] | [1-Ethyl-6-methyl-2-(3-trifluoromethyl-phenyl)-1H-benzoimidazol-5-yl]-(4-pyridin-4-yl-thiazol-2-yl)-amine | (ESI-) m/z 478 (M − H)⁻ Retention time = 2.50 mins |

TABLE 1-continued

| Ex # | Chemical Structure | Name | LCMS |
|---|---|---|---|
| 106 | 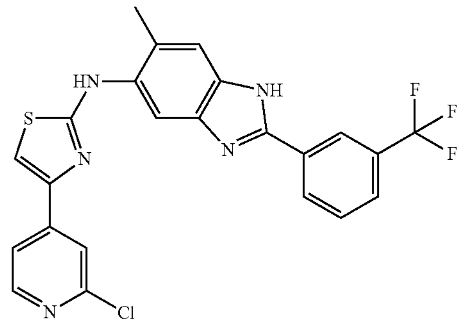 [SMILES: Cc1cc2[nH]c(-c3cccc(C(F)(F)F)c3)nc2cc1Nc1nc(-c2ccnc(Cl)c2)cs1] | [4-(2-Chloro-pyridin-4-yl)-thiazol-2-yl]-[6-methyl-2-(3-trifluoromethyl-phenyl)-1H-benzoimidazol-5-yl]-amine | (ESI-) m/z 484 (M − H)⁻ Retention time = 3.35 mins |
| 107 | 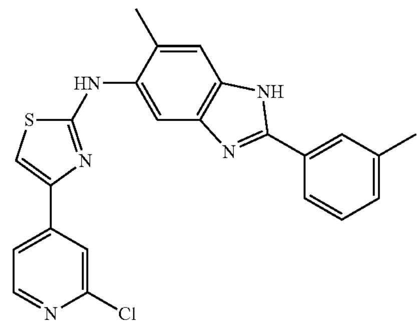 [SMILES: Cc1cccc(-c2nc3cc(Nc4nc(-c5ccnc(Cl)c5)cs4)c(C)cc3[nH]2)c1] | [4-(2-Chloro-pyridin-4-yl)-thiazol-2-yl]-(6-methyl-2-m-tolyl-1H-benzoimidazol-5-yl)-amine | (ESI-) m/z 430 (M − H)⁻ Retention time = 2.76 mins |
| 108 | 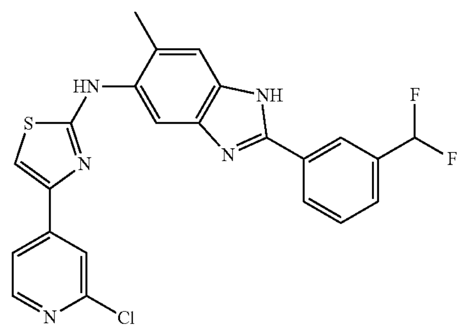 [SMILES: Cc1cc2[nH]c(-c3cccc(C(F)F)c3)nc2cc1Nc1nc(-c2ccnc(Cl)c2)cs1] | [4-(2-Chloro-pyridin-4-yl)-thiazol-2-yl]-[2-(3-difluoromethyl-phenyl)-6-methyl-1H-benzoimidazol-5-yl]-amine | (ESI-) m/z 466 (M − H)⁻ Retention time = 2.95 mins |
| 109 | 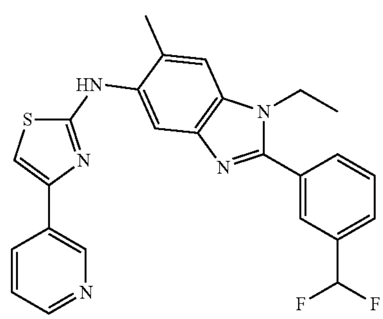 [SMILES: CCn1c(-c2cccc(C(F)F)c2)nc2cc(Nc3nc(-c4cccnc4)cs3)c(C)cc21] | [2-(3-Difluoromethyl-phenyl)-1-ethyl-6-methyl-1H-benzoimidazol-5-yl]-(4-pyridin-3-yl-thiazol-2-yl)-amine | (ESI-) m/z 460 (M − H)⁻ Retention time = 2.39 mins |
| 110 | 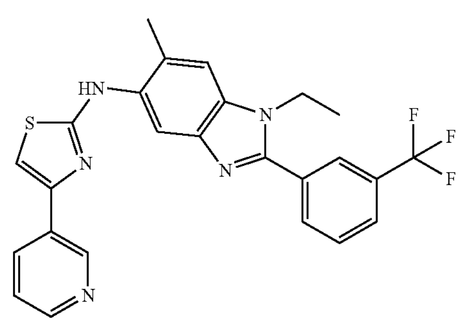 [SMILES: CCn1c(-c2cccc(C(F)(F)F)c2)nc2cc(Nc3nc(-c4cccnc4)cs3)c(C)cc21] | [1-Ethyl-6-methyl-2-(3-trifluoromethyl-phenyl)-1H-benzoimidazol-5-yl]-(4-pyridin-3-yl-thiazol-2-yl)-amine | (ESI-) m/z 478 (M − H)⁻ Retention time = 2.69 mins |

TABLE 1-continued

| Ex # | Chemical Structure | Name | LCMS |
|---|---|---|---|
| 111 | 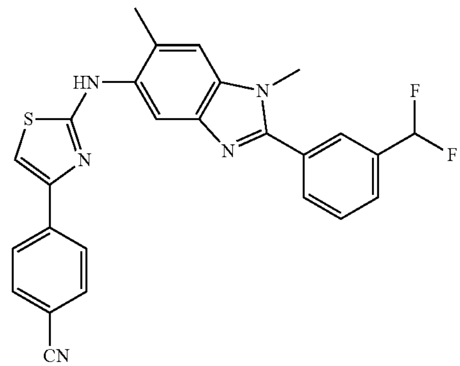 [SMILES: Cc1cc2c(cc1Nc1nc(-c3ccc(C#N)cc3)cs1)nc(-c1cccc(C(F)F)c1)n2C] | 4-{2-[2-(3-Difluoromethyl-phenyl)-1,6-dimethyl-1H-benzoimidazol-5-ylamino]-thiazol-4-yl}-benzonitrile | (ESI-) m/z 470 (M − H)⁻ Retention time = 3.06 mins |
| 112 | 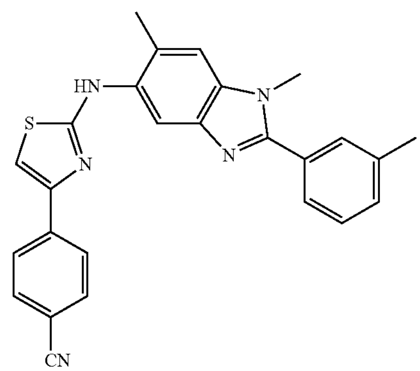 [SMILES: Cc1cccc(-c2nc3cc(Nc4nc(-c5ccc(C#N)cc5)cs4)c(C)cc3n2C)c1] | 4-[2-(1,6-Dimethyl-2-m-tolyl-1H-benzoimidazol-5-ylamino)-thiazol-4-yl]-benzonitrile | (ESI-) m/z 434 (M − H)⁻ Retention time = 2.94 mins |
| 113 | 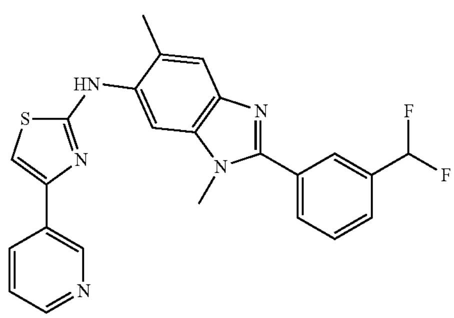 [SMILES: Cc1cc2nc(-c3cccc(C(F)F)c3)n(C)c2cc1Nc1nc(-c2cccnc2)cs1] | [2-(3-Difluoromethyl-phenyl)-3,6-dimethyl-3H-benzoimidazol-5-yl]-(4-pyridin-3-yl-thiazol-2-yl)-amine | (ESI-) m/z 446 (M − H)⁻ Retention time = 2.15 mins |
| 114 | 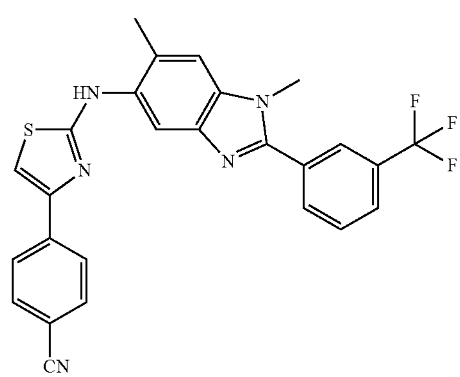 [SMILES: Cc1cc2c(cc1Nc1nc(-c3ccc(C#N)cc3)cs1)nc(-c1cccc(C(F)(F)F)c1)n2C] | 4-{2-[1,6-Dimethyl-2-(3-trifluoromethyl-phenyl)-1H-benzoimidazol-5-ylamino]-thiazol-4-yl}-benzonitrile | (ESI-) m/z 488 (M − H)⁻ Retention time = 3.39 mins |

TABLE 1-continued

| Ex # | Chemical Structure | Name | LCMS |
|---|---|---|---|
| 115 | 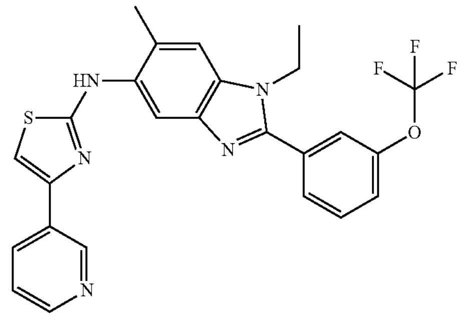 [SMILES: CCn1c(-c2cccc(OC(F)(F)F)c2)nc2cc(Nc3nc(-c4cccnc4)cs3)c(C)cc21] | [1-Ethyl-6-methyl-2-(3-trifluoromethoxy-phenyl)-1H-benzoimidazol-5-yl]-(4-pyridin-3-yl-thiazol-2-yl)-amine | (ESI-) m/z 494 (M − H)⁻ Retention time = 2.76 mins |
| 116 | 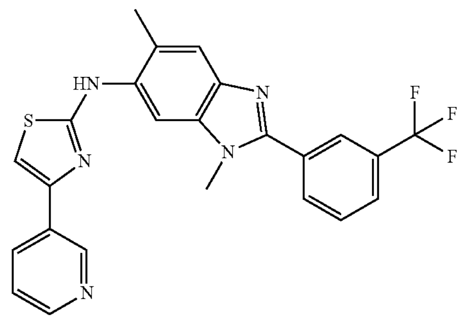 [SMILES: Cc1cc2nc(-c3cccc(C(F)(F)F)c3)n(C)c2cc1Nc1nc(-c2cccnc2)cs1] | [3,6-Dimethyl-2-(3-trifluoromethyl-phenyl)-3H-benzoimidazol-5-yl]-(4-pyridin-3-yl-thiazol-2-yl)-amine | (ESI-) m/z 464 (M − H)⁻ Retention time = 2.46 mins |
| 117 | 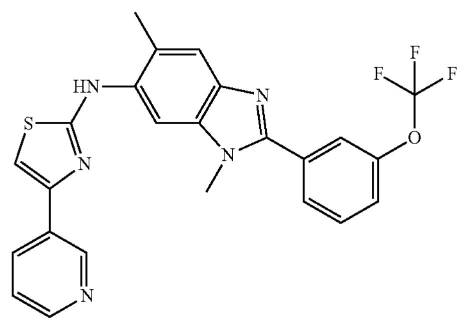 [SMILES: Cc1cc2nc(-c3cccc(OC(F)(F)F)c3)n(C)c2cc1Nc1nc(-c2cccnc2)cs1] | [3,6-Dimethyl-2-(3-trifluoromethoxy-phenyl)-3H-benzoimidazol-5-yl]-(4-pyridin-3-yl-thiazol-2-yl)-amine | (ESI-) m/z 480 (M − H)⁻ Retention time = 2.53 mins |
| 118 | 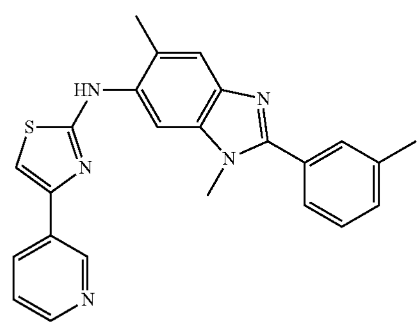 [SMILES: Cc1cccc(-c2nc3cc(C)c(Nc4nc(-c5cccnc5)cs4)cc3n2C)c1] | (3,6-Dimethyl-2-m-tolyl-3H-benzoimidazol-5-yl)-(4-pyridin-3-yl-thiazol-2-yl)-amine | (ESI-) m/z 410 (M − H)⁻ Retention time = 2.06 mins |
| 119 | 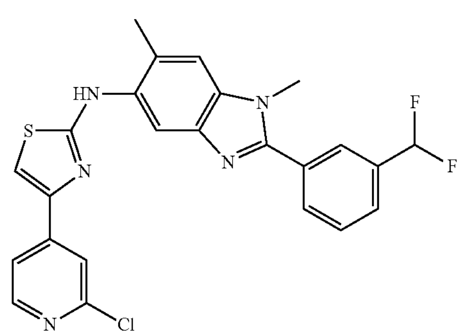 [SMILES: Cc1cc2c(cc1Nc1nc(-c3ccnc(Cl)c3)cs1)nc(-c1cccc(C(F)F)c1)n2C] | [4-(2-Chloro-pyridin-4-yl)-thiazol-2-yl]-[2-(3-difluoromethyl-phenyl)-1,6-dimethyl-1H-benzoimidazol-5-yl]-amine | (ESI-) m/z 480 (M − H)⁻ Retention time = 2.95 mins |

Note: LCMS values use $(M-H)^-$ notation.

TABLE 1-continued

| Ex # | Chemical Structure | Name | LCMS |
|------|-------------------|------|------|
| 120 | 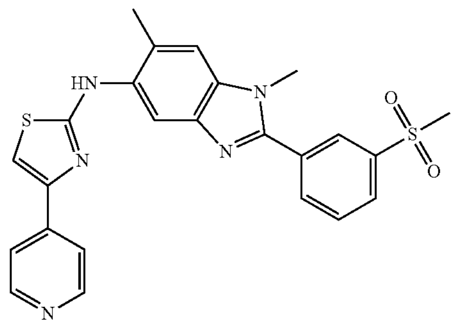 [SMILES: Cc1cc2c(cc1Nc1nc(-c3ccncc3)cs1)nc(-c1cccc(S(C)(=O)=O)c1)n2C] | [2-(3-Methanesulfonyl-phenyl)-1,6-dimethyl-1H-benzoimidazol-5-yl]-(4-pyridin-4-yl-thiazol-2-yl)-amine | (ESI-) m/z 474 (M − H)⁻ Retention time = 1.86 mins |
| 121 | 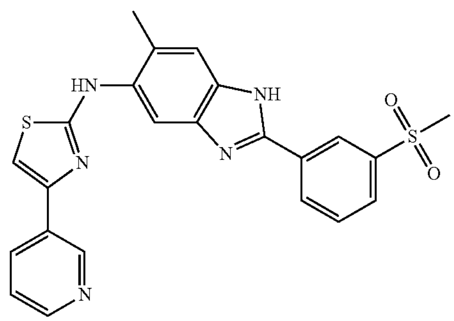 [SMILES: Cc1cc2[nH]c(-c3cccc(S(C)(=O)=O)c3)nc2cc1Nc1nc(-c2cccnc2)cs1] | [2-(3-Methanesulfonyl-phenyl)-6-methyl-1H-benzoimidazol-5-yl]-(4-pyridin-3-yl-thiazol-2-yl)-amine | (ESI-) m/z 460 (M − H)⁻ Retention time = 1.97 mins |
| 122 | 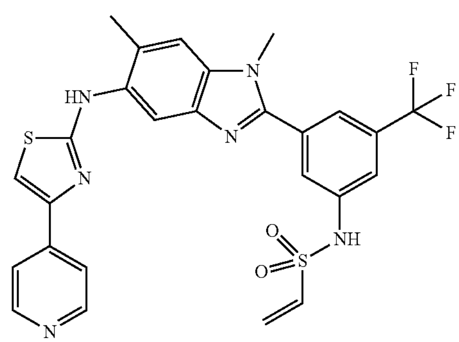 [SMILES: C=CS(=O)(=O)Nc1cc(-c2nc3cc(Nc4nc(-c5ccncc5)cs4)c(C)cc3n2C)cc(C(F)(F)F)c1] | Ethenesulfonic acid {3-[1,6-dimethyl-5-(4-pyridin-4-yl-thiazol-2-ylamino)-yl]-5-trifluoromethyl-phenyl}-amide | (ESI-) m/z 569 (M − H)⁻ Retention time = 2.49 mins |
| 123 | 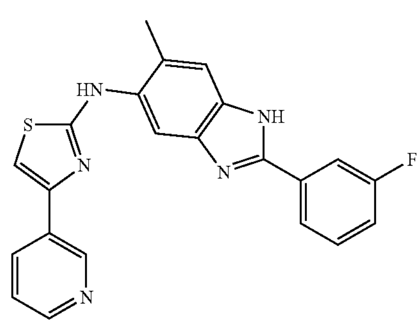 [SMILES: Cc1cc2[nH]c(-c3cccc(F)c3)nc2cc1Nc1nc(-c2cccnc2)cs1] | [2-(3-Fluoro-phenyl)-6-methyl-1H-benzoimidazol-5-yl]-(4-pyridin-3-yl-thiazol-2-yl)-amine | (ESI-) m/z 400 (M − H)⁻ Retention time = 2.09 mins |

TABLE 1-continued

| Ex # | Chemical Structure | Name | LCMS |
|------|-------------------|------|------|
| 124 | 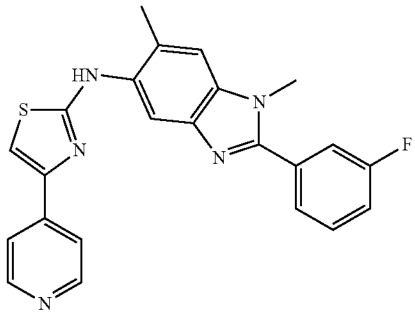 [SMILES: Cc1cc2c(cc1Nc1nc(-c3ccncc3)cs1)nc(-c1cccc(F)c1)n2C] | [2-(3-Fluoro-phenyl)-1,6-dimethyl-1H-benzoimidazol-5-yl]-(4-pyridin-4-yl-thiazol-2-yl)-amine | (ESI-) m/z 414 (M − H)⁻ Retention time = 1.97 mins |
| 125 | 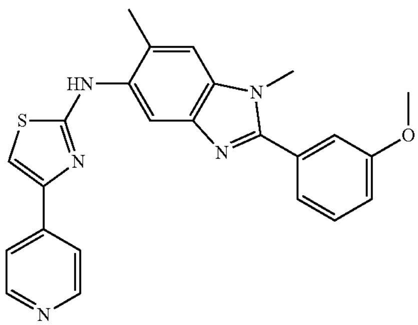 [SMILES: COc1cccc(-c2nc3cc(Nc4nc(-c5ccncc5)cs4)c(C)cc3n2C)c1] | [2-(3-Methoxy-phenyl)-1,6-dimethyl-1H-benzoimidazol-5-yl]-(4-pyridin-4-yl-thiazol-2-yl)-amine | (ESI-) m/z 426 (M − H)⁻ Retention time = 1.93 mins |
| 126 | 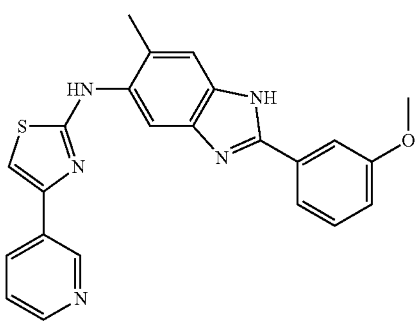 [SMILES: COc1cccc(-c2nc3cc(Nc4nc(-c5cccnc5)cs4)c(C)cc3[nH]2)c1] | [2-(3-Methoxy-phenyl)-6-methyl-1H-benzoimidazol-5-yl]-(4-pyridin-3-yl-thiazol-2-yl)-amine | (ESI-) m/z 412 (M − H)⁻ Retention time = 2.06 mins |
| 127 | 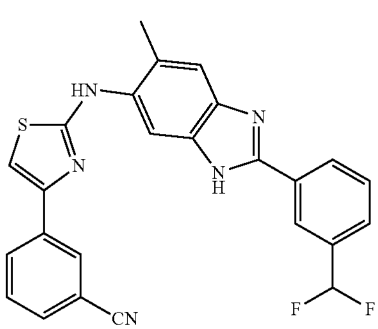 [SMILES: Cc1cc2nc(-c3cccc(C(F)F)c3)[nH]c2cc1Nc1nc(-c2cccc(C#N)c2)cs1] | 3-{2-[2-(3-Difluoromethyl-phenyl)-6-methyl-3H-benzoimidazol-5-ylamino]-thiazol-4-yl}-benzonitrile | (ESI-) m/z 456 (M − H)⁻ Retention time = 3.11 mins |

TABLE 1-continued

| Ex # | Chemical Structure | Name | LCMS |
|---|---|---|---|
| 128 | 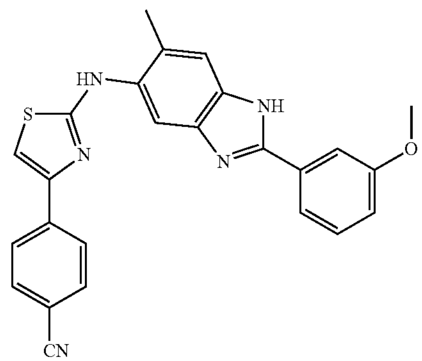 [SMILES: COc1cccc(-c2nc3cc(Nc4nc(-c5ccc(C#N)cc5)cs4)c(C)cc3[nH]2)c1] | 4-{2-[2-(3-Methoxy-phenyl)-6-methyl-1H-benzoimidazol-5-ylamino]-thiazol-4-yl}-benzonitrile | (ESI-) m/z 436 (M − H)⁻ Retention time = 2.88 mins |
| 129 | 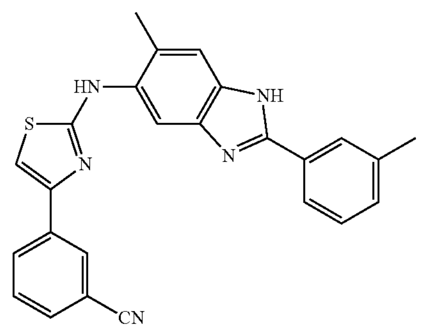 [SMILES: Cc1cccc(-c2nc3cc(Nc4nc(-c5cccc(C#N)c5)cs4)c(C)cc3[nH]2)c1] | 3-[2-(6-Methyl-2-m-tolyl-1H-benzoimidazol-5-ylamino)-thiazol-4-yl]-benzonitrile | (ESI-) m/z 420 (M − H)⁻ Retention time = 2.92 mins |
| 130 | 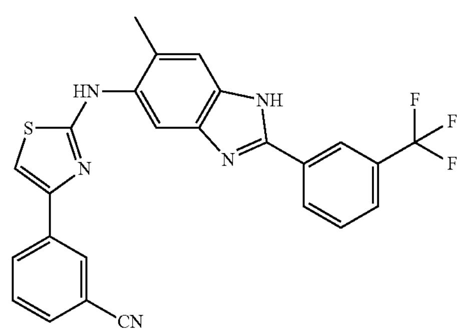 | 3-{2-[6-Methyl-2-(3-trifluoromethyl-phenyl)-1H-benzoimidazol-5-ylamino]-thiazol-4-yl}-benzonitrile | (ESI-) m/z 474 (M − H)⁻ Retention time = 3.49 mins |
| 131 | 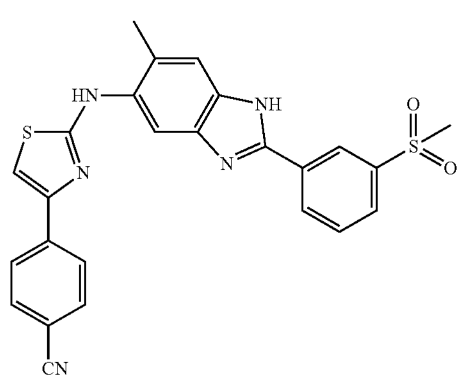 [SMILES: Cc1cc2[nH]c(-c3cccc(S(C)(=O)=O)c3)nc2cc1Nc1nc(-c2ccc(C#N)cc2)cs1] | 4-{2-[2-(3-Methanesulfonyl-phenyl)-6-methyl-1H-benzoimidazol-5-ylamino]-thiazol-4-yl}-benzonitrile | (ESI-) m/z 484 (M − H)⁻ Retention time = 2.90 mins |

TABLE 1-continued

| Ex # | Chemical Structure | Name | LCMS |
|------|--------------------|------|------|
| 132 | 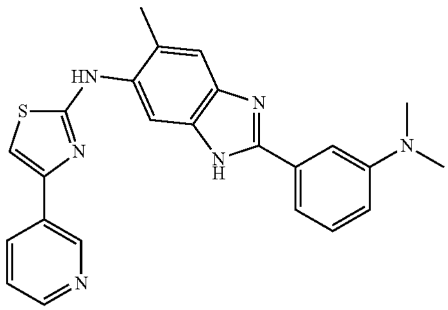 [SMILES: Cc1cc2nc(-c3cccc(N(C)C)c3)[nH]c2cc1Nc1nc(-c2cccnc2)cs1] | [2-(3-Dimethylamino-phenyl)-6-methyl-3H-benzoimidazol-5-yl]-(4-pyridin-3-yl-thiazol-2-yl)-amine | (ESI-) m/z 425 (M − H)⁻ Retention time = 2.16 mins |
| 133 | 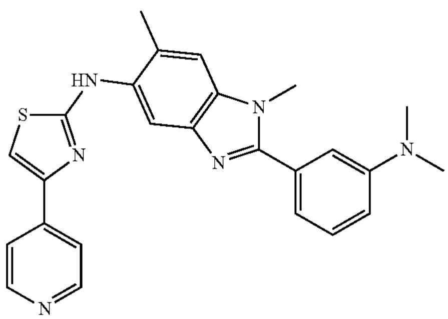 [SMILES: Cc1cc2c(cc1Nc1nc(-c3ccncc3)cs1)nc(-c1cccc(N(C)C)c1)n2C] | [2-(3-Dimethylamino-phenyl)-1,6-dimethyl-1H-benzoimidazol-5-yl]-(4-pyridin-4-yl-thiazol-2-yl)-amine | (ESI-) m/z 439 (M − H)⁻ Retention time = 2.02 mins |
| 134 | 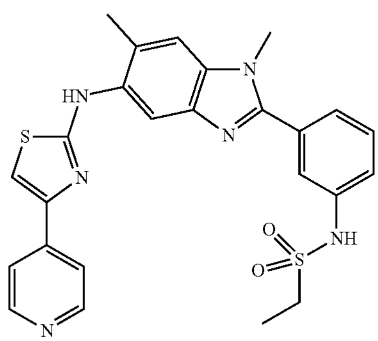 [SMILES: CCS(=O)(=O)Nc1cccc(-c2nc3cc(Nc4nc(-c5ccncc5)cs4)c(C)cc3n2C)c1] | Ethanesulfonic acid {3-[1,6-dimethyl-5-(4-pyridin-4-yl-thiazol-2-ylamino)-1H-benzoimidazol-2-yl]-phenyl}-amide | (ESI-) m/z 503 (M − H)⁻ Retention time = 1.89 mins |
| 135 | 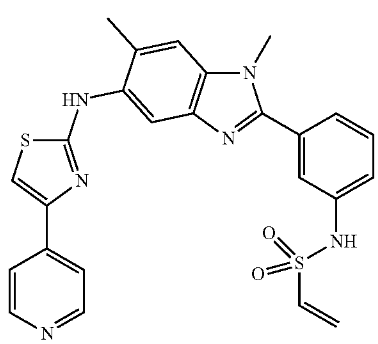 [SMILES: C=CS(=O)(=O)Nc1cccc(-c2nc3cc(Nc4nc(-c5ccncc5)cs4)c(C)cc3n2C)c1] | Ethenesulfonic acid {3-[1,6-dimethyl-5-(4-pyridin-4-yl-thiazol-2-ylamino)-1H-benzoimidazol-2-yl]-phenyl}-amide | (ESI-) m/z 501 (M − H)⁻ Retention time = 1.92 mins |

TABLE 1-continued

| Ex # | Chemical Structure | Name | LCMS |
|------|-------------------|------|------|
| 136 | 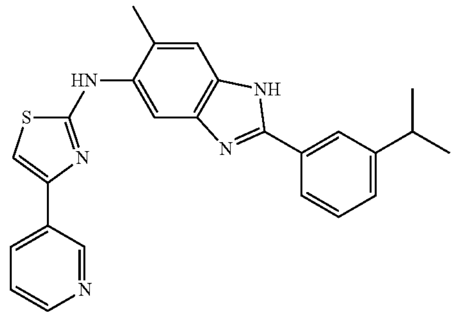 [SMILES: Cc1cc2[nH]c(-c3cccc(C(C)C)c3)nc2cc1Nc1nc(-c2cccnc2)cs1] | [2-(3-Isopropyl-phenyl)-6-methyl-1H-benzoimidazol-5-yl]-(4-pyridin-3-yl-thiazol-2-yl)-amine | (ESI-) m/z 424 (M − H)⁻ Retention time = 2.43 mins |
| 137 | 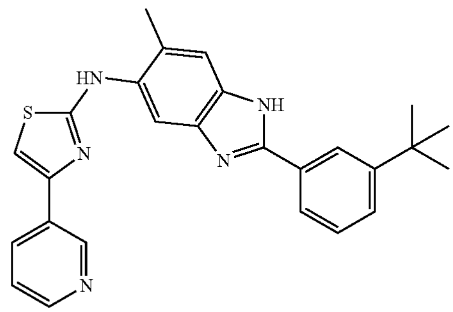 [SMILES: Cc1cc2[nH]c(-c3cccc(C(C)(C)C)c3)nc2cc1Nc1nc(-c2cccnc2)cs1] | [2-(3-tert-Butyl-phenyl)-6-methyl-1H-benzoimidazol-5-yl]-(4-pyridin-3-yl-thiazol-2-yl)-amine | (ESI-) m/z 438 (M − H)⁻ Retention time = 2.57 mins |
| 138 | 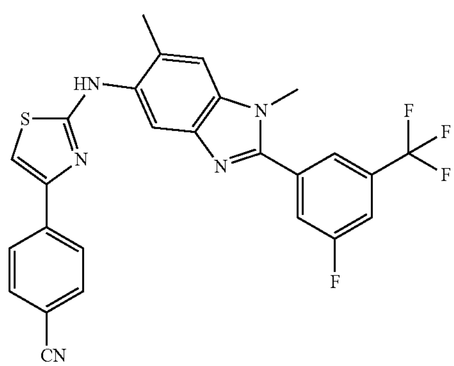 [SMILES: Cc1cc2c(cc1Nc1nc(-c3ccc(C#N)cc3)cs1)nc(-c1cc(F)cc(C(F)(F)F)c1)n2C] | 4-{2-[2-(3-Fluoro-5-trifluoromethyl-phenyl)-1,6-dimethyl-1H-benzoimidazol-5-ylamino]-thiazol-4-yl}-benzonitrile | (ESI-) m/z 506 (M − H)⁻ Retention time = 3.80 mins |
| 139 | 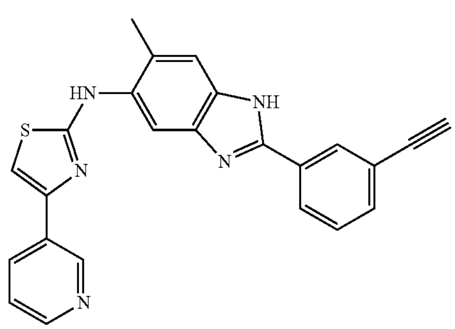 [SMILES: C#Cc1cccc(-c2nc3cc(Nc4nc(-c5cccnc5)cs4)c(C)cc3[nH]2)c1] | [2-(3-Ethynyl-phenyl)-6-methyl-1H-benzoimidazol-5-yl]-(4-pyridin-3-yl-thiazol-2-yl)-amine | (ESI-) m/z 406 (M − H)⁻ Retention time = 2.19 mins |

TABLE 1-continued

| Ex # | Chemical Structure | Name | LCMS |
|---|---|---|---|
| 140 | 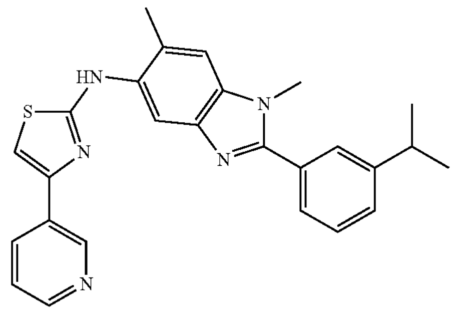 [SMILES: Cc1cc2c(cc1Nc1nc(-c3cccnc3)cs1)nc(-c1cccc(C(C)C)c1)n2C] | [2-(3-Isopropyl-phenyl)-1,6-dimethyl-1H-benzoimidazol-5-yl]-(4-pyridin-3-yl-thiazol-2-yl)-amine | (ESI-) m/z 438 (M − H)⁻ Retention time = 2.51 mins |
| 141 | 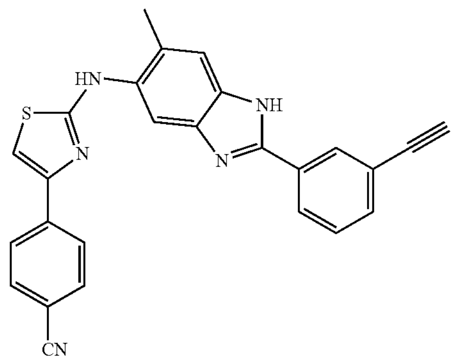 [SMILES: C#Cc1cccc(-c2nc3cc(Nc4nc(-c5ccc(C#N)cc5)cs4)c(C)cc3[nH]2)c1] | 4-{2-[2-(3-Ethynyl-phenyl)-6-methyl-1H-benzoimidazol-5-ylamino]-thiazol-4-yl}-benzonitrile | (ESI-) m/z 430 (M − H)⁻ Retention time = 3.07 mins |
| 142 | 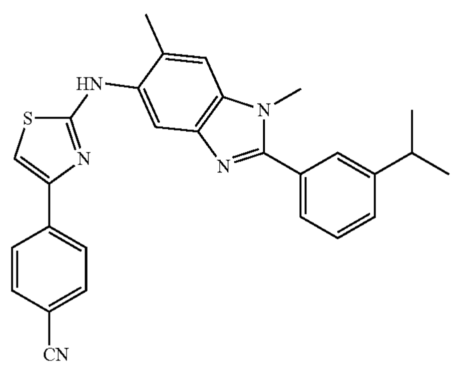 [SMILES: Cc1cc2c(cc1Nc1nc(-c3ccc(C#N)cc3)cs1)nc(-c1cccc(C(C)C)c1)n2C] | 4-{2-[2-(3-Isopropyl-phenyl)-1,6-dimethyl-1H-benzoimidazol-5-ylamino]-thiazol-4-yl}-benzonitrile | (ESI-) m/z 462 (M − H)⁻ Retention time = 3.24 mins |
| 143 | 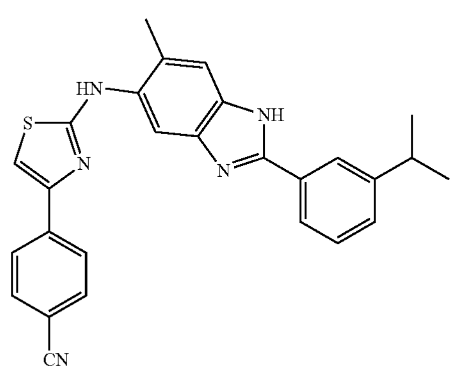 [SMILES: Cc1cc2[nH]c(-c3cccc(C(C)C)c3)nc2cc1Nc1nc(-c2ccc(C#N)cc2)cs1] | 4-{2-[2-(3-Isopropyl-phenyl)-6-methyl-1H-benzoimidazol-5-ylamino]-thiazol-4-yl}-benzonitrile | (ESI-) m/z 448 (M − H)⁻ Retention time = 3.19 mins |

TABLE 1-continued

| Ex # | Chemical Structure | Name | LCMS |
|---|---|---|---|
| 144 | 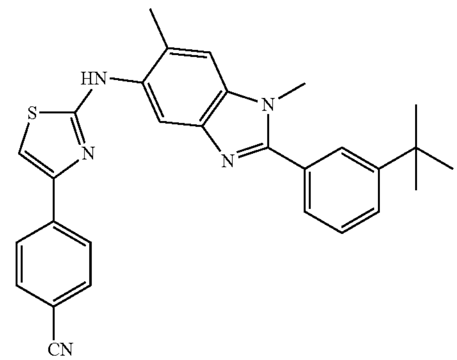 [SMILES: Cc1cc2c(cc1Nc1nc(-c3ccc(C#N)cc3)cs1)nc(-c1cccc(C(C)(C)C)c1)n2C] | 4-{2-[2-(3-tert-Butyl-phenyl)-1,6-dimethyl-1H-benzoimidazol-5-ylamino]-thiazol-4-yl}-benzonitrile | (ESI-) m/z 476 (M − H)⁻ Retention time = 3.37 mins |
| 145 | 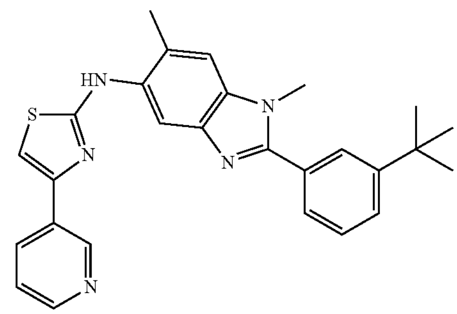 [SMILES: Cc1cc2c(cc1Nc1nc(-c3cccnc3)cs1)nc(-c1cccc(C(C)(C)C)c1)n2C] | [2-(3-tert-Butyl-phenyl)-1,6-dimethyl-1H-benzoimidazol-5-yl]-(4-pyridin-3-yl-thiazol-2-yl)-amine | (ESI-) m/z 452 (M − H)⁻ Retention time = 2.67 mins |
| 146 | 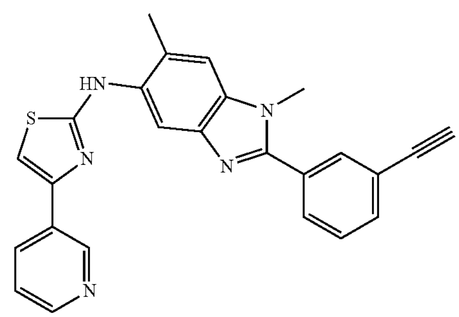 [SMILES: C#Cc1cccc(-c2nc3cc(Nc4nc(-c5cccnc5)cs4)c(C)cc3n2C)c1] | [2-(3-Ethynyl-phenyl)-1,6-dimethyl-1H-benzoimidazol-5-yl]-(4-pyridin-3-yl-thiazol-2-yl)-amine | (ESI-) m/z 420 (M − H)⁻ Retention time = 2.25 mins |
| 147 | 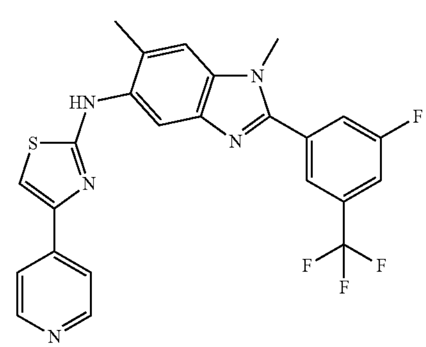 [SMILES: Cc1cc2c(cc1Nc1nc(-c3ccncc3)cs1)nc(-c1cc(F)cc(C(F)(F)F)c1)n2C] | [2-(3-Fluoro-5-trifluoromethyl-phenyl)-1,6-dimethyl-1H-benzoimidazol-5-yl]-(4-pyridin-4-yl-thiazol-2-yl)-amine | (ESI-) m/z 482 (M − H)⁻ Retention time = 2.64 mins |

TABLE 1-continued

| Ex # | Chemical Structure | Name | LCMS |
|---|---|---|---|
| 148 | 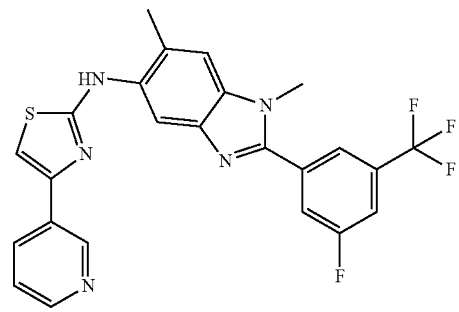 [SMILES: Cc1cc2c(cc1Nc1nc(-c3cccnc3)cs1)nc(-c1cc(F)cc(C(F)(F)F)c1)n2C] | [2-(3-Fluoro-5-trifluoromethyl-phenyl)-1,6-dimethyl-1H-benzoimidazol-5-yl]-(4-pyridin-3-yl-thiazol-2-yl)-amine | (ESI-) m/z 482 (M − H)⁻ Retention time = 2.84 mins |
| 149 | 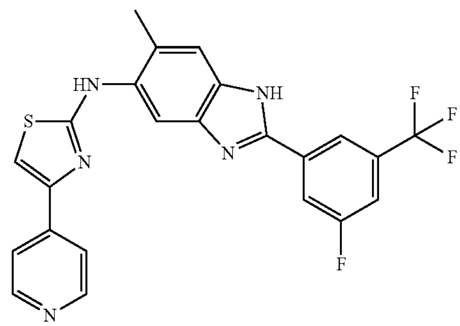 [SMILES: Cc1cc2[nH]c(-c3cc(F)cc(C(F)(F)F)c3)nc2cc1Nc1nc(-c2ccncc2)cs1] | [2-(3-Fluoro-5-trifluoromethyl-phenyl)-6-methyl-1H-benzoimidazol-5-yl]-(4-pyridin-4-yl-thiazol-2-yl)-amine | (ESI-) m/z 468 (M − H)⁻ Retention time = 2.65 mins |
| 150 | 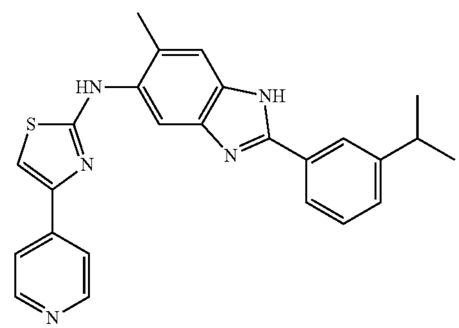 [SMILES: Cc1cc2[nH]c(-c3cccc(C(C)C)c3)nc2cc1Nc1nc(-c2ccncc2)cs1] | [2-(3-Isopropyl-phenyl)-6-methyl-1H-benzoimidazol-5-yl]-(4-pyridin-4-yl-thiazol-2-yl)-amine | (ESI-) m/z 424 (M − H)⁻ Retention time = 2.19 mins |
| 151 | 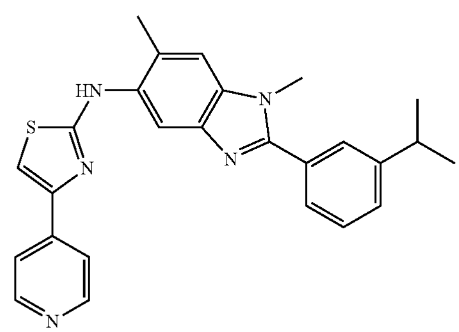 | [2-(3-Isopropyl-phenyl)-1,6-dimethyl-1H-benzoimidazol-5-yl]-(4-pyridin-4-yl-thiazol-2-yl)-amine | (ESI-) m/z 438 (M − H)⁻ Retention time = 2.28 mins |
| 152 | 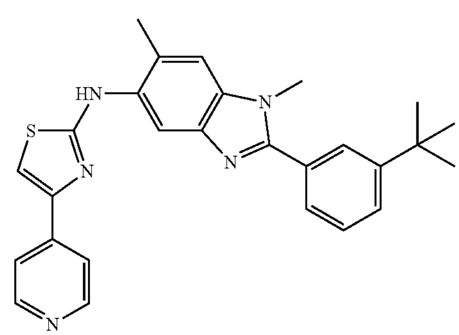 [SMILES: Cc1cc2c(cc1Nc1nc(-c3ccncc3)cs1)nc(-c1cccc(C(C)(C)C)c1)n2C] | [2-(3-tert-Butyl-phenyl)-1,6-dimethyl-1H-benzoimidazol-5-yl]-(4-pyridin-4-yl-thiazol-2-yl)-amine | (ESI-) m/z 452 (M − H)⁻ Retention time = 2.39 mins |

TABLE 1-continued

| Ex # | Chemical Structure | Name | LCMS |
|---|---|---|---|
| 153 | 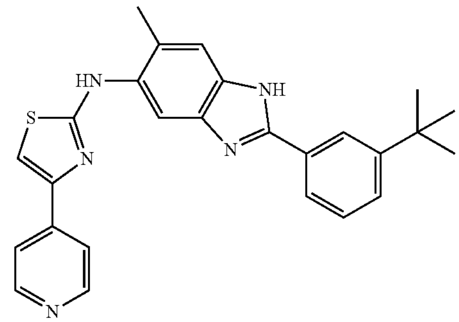 [SMILES: Cc1cc2[nH]c(-c3cccc(C(C)(C)C)c3)nc2cc1Nc1nc(-c2ccncc2)cs1] | [2-(3-tert-Butyl-phenyl)-6-methyl-1H-benzoimidazol-5-yl]-(4-pyridin-4-yl-thiazol-2-yl)-amine | (ESI-) m/z 438 (M − H)⁻ Retention time = 2.30 mins |
| 154 | 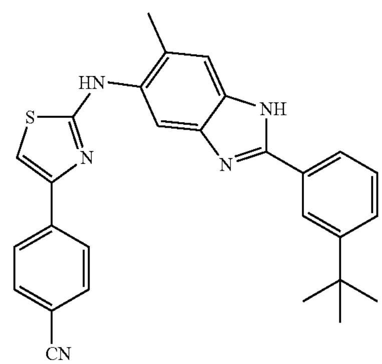 [SMILES: Cc1cc2[nH]c(-c3cccc(C(C)(C)C)c3)nc2cc1Nc1nc(-c2ccc(C#N)cc2)cs1] | 4-{2-[2-(3-tert-Butyl-phenyl)-6-methyl-1H-benzoimidazol-5-ylamino]-thiazol-4-yl}-benzonitrile | (ESI-) m/z 462 (M − H)⁻ Retention time = 3.31 mins |

The compounds of the present invention may be prepared using the general protocol as follows.

General Synthetic Procedures

Compounds of the invention can be prepared by several methods including methods outlined in Schemes 1-5, wherein the substituents are as defined in formula (I), above, except where further noted. The synthetic methods described below are merely exemplary, and the compounds of the invention may be synthesized by alternate routes as appreciated by persons of ordinary skill in the art.

Accordingly, the aminoheteroaryl (VI) can be reacted with compounds of formula (VII) in the presence of base through copper or palladium coupling reaction, where L1 can be I, Br or Cl. The tert-butyl ester in compounds (VIII) can be cleaved under acid conditions to give compounds (IX). The nitro group in compounds (IX) undergoes reduction under standard conditions to provide the expected dianilines (X). Finally, compounds of formula (Iα) may be prepared by a reaction between dianilines (X) and aldehydes (XI) under basic conditions with a suitable solvent such as DMF, in the presence of sodium bisulfite, as shown in scheme 1 below.

Scheme 1

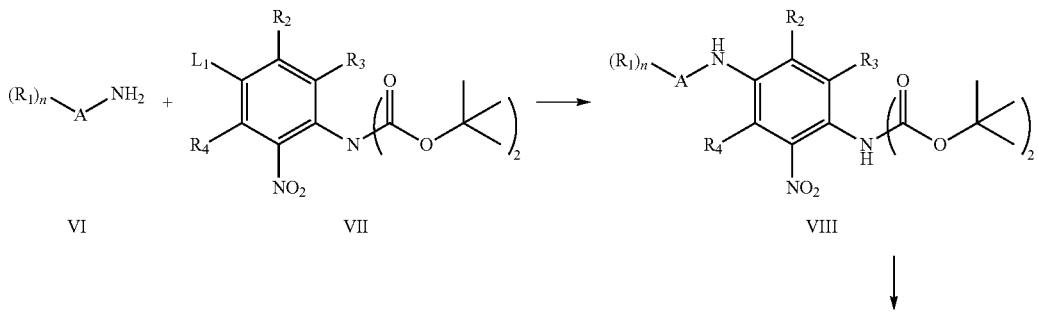

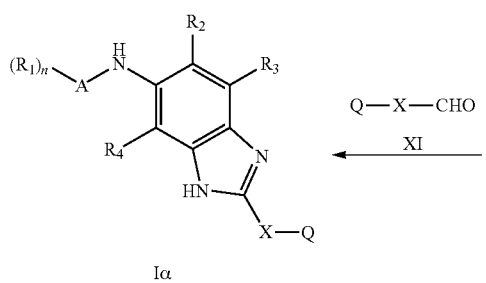
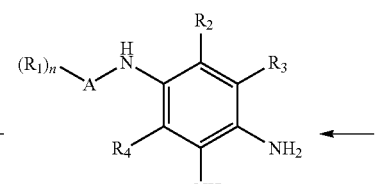
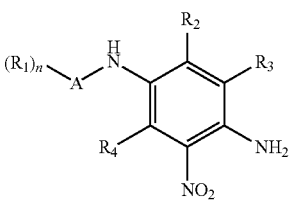

Compounds of formula (Iα) may alternatively be prepared according to the protocol outlined in scheme 2 below, by reacting dianiline (X) and compound (XII), wherein L2 is alkoxy or halogen or hydroxyl group. Wherein L2 is alkoxy group, the ester (XII) is coupled with (X) using trimethylaluminium as activating agent in aprotic solvent such as dichloromethane or toluene. Wherein L2 is a halogen such as chloride, the acyl chloride (XII) is coupled with (X) in basic condition using preferably triethylamine in aprotic solvent such as dichloromethane. Wherein L2 is hydroxyl group, the carboxylic acid (XII) is coupled with (X) using activating agents such as Mukaiyama's Reagent or HOBt/EDCl in aprotic solvent, preferably DMF. The mixture of compounds (XIII) and (XIV) is reacted in acidic conditions by using a suitable acid such as acetic acid or p-toluenesulfonic acid, with neat or with heating in the presence of suitable solvent such as toluene or dioxane, to give compounds of formula (Iα), as shown in scheme 2 below.

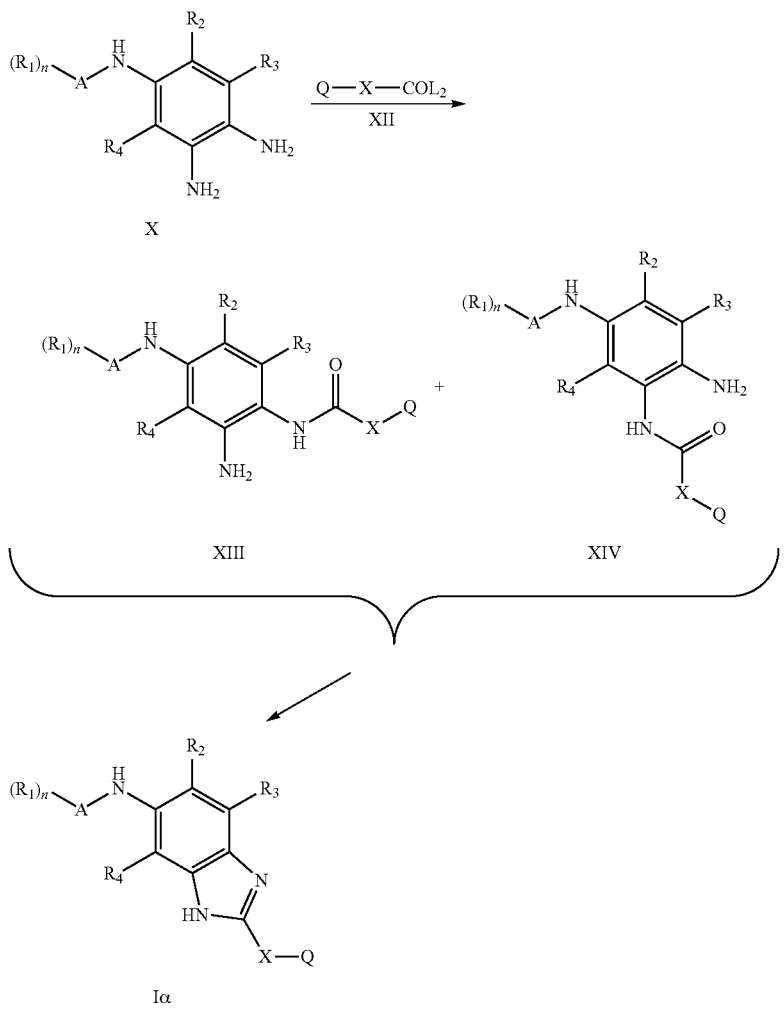

Person of ordinary skill in the art is able to recognize that compounds of formula (Iα) may alternatively be prepared according to the protocol outlined in scheme 3 below. Accordingly, the aminoheteroaryl (VI) can be reacted with compounds of formula (XV) in the presence of base through copper or palladium coupling reaction, where L1 can be I, Br or Cl to give compounds of formula (I).

Scheme 3

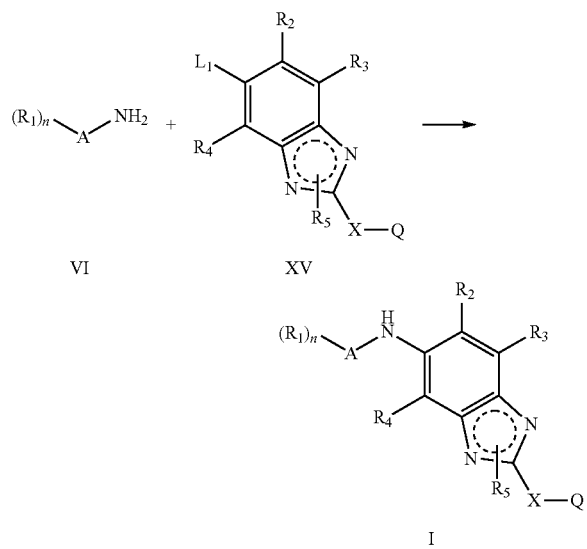

Wherein A is a thiazole ring, the corresponding compounds of formula (I) can be prepared by method outlined in scheme 4. Reaction of an appropriately protected thiourea (XVI) with an acylbromide at a temperature preferably between 20° C. and 80° C. in the presence of a base such as $K_2CO_3$ and in a solvent such as methanol, yields compounds (XVII). Treatment of compounds (XVII) with ammonium hydroxide at a temperature between 60° C. and 100° C. yields the aniline (XVIII). Finally and according to methods described in scheme 1 and scheme 2, compounds (XIX) of formula (I) wherein A is a thiazole ring are obtained.

Scheme 4

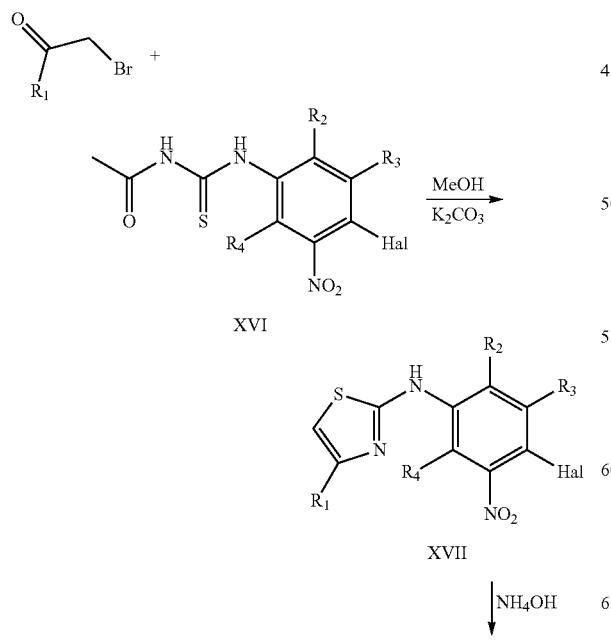

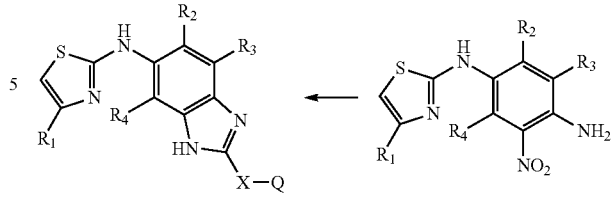

Wherein A is an oxazole ring, the corresponding compounds of formula (I) can be prepared by method outlined in scheme 5. Treatment of an appropriately acylbromide with sodium azide in a solvent such water gives acylazide (XX). Reaction of substituted isothiocyanate (XXI) with acylazide (XX) in the presence of a phosphine such as triphenylphosphine, in a solvent such as dioxane and at a temperature preferably between 20° C. and 100° C. yields compounds (XXII). Treatment of compounds (XX) with ammonium hydroxide at a temperature between 60° C. and 100° C. yields the aniline (XXIII). Finally and according to methods described in scheme 1 and scheme 2, compounds (XXIV) of formula (I) wherein A is an oxazole ring are obtained.

Scheme 5

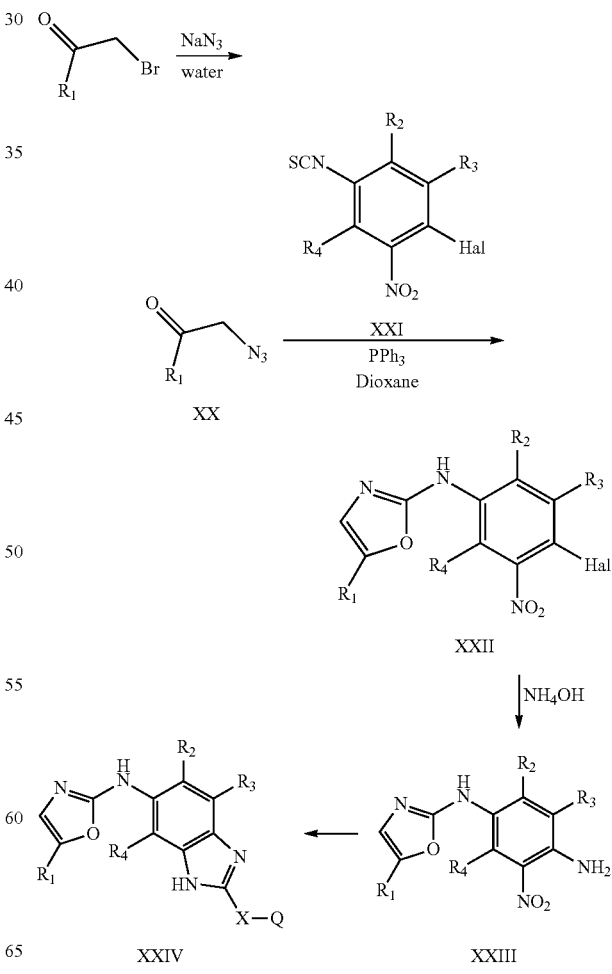

Examples of Compound Synthesis

The invention will be more fully understood by reference to the following preparative examples, but they should not be construed as limiting the scope of the invention.

General: All chemicals used were commercial reagent grade products. Solvents were of anhydrous commercial grade and were used without further purification. The progress of the reactions was monitored by thin layer chromatography using precoated silica gel 60F 254, Merck TLC plates, which were visualized under UV light. Multiplicities in $^1$H NMR spectra are indicated as singlet (s), broad singlet (br s), doublet (d), triplet (t), quadruplet (q), and multiplet (m) and the NMR spectrum were performed either on a Bruker Avance 300, 360 or 400 MHz spectrometer. LCMS was run on a Ultra-high performance liquid chromatography (UPLC) ACQUITY Waters instrument coupled to a TQD mass spectrometer. The flow used is 6 mL/min, and the eluents are Water+0.1% Formic acid (eluent A) and Acetonitrile+0.1% Formic acid (eluent B). The gradient is: starting at t=0.0 min with eluent A/B: 95/5 until t=0.5 min; then a linear gradient from t=0.5 min to t=5.0 min reaching eluent A/B: 0/100; then staying at this state from t=5.0 min until t=7.0 min. The column used was a Waters HSS C18 1.7 µm, 2.1×50 mm. The detection instrument used was the triple quadrupole mass spectrometer (TQD) using ESI positive and negative mode.

ABBREVIATIONS

AcCl Acetyl chloride
AcOEt Ethyl acetate
AcOH Acetic acid
Boc t-Butoxycarbonyl
Br$_2$ Bromine
nBuLi n-Butyllithium
C$_2$Cl$_6$ Hexachloroethane
CDCl$_3$ Deuterochloroform
DCM Dichloromethane
DDQ 2,3-Dichloro-5,6-dicyano-1,4-benzoquinone
DMAP 4-(Dimethylamino)pyridine
DMEDA N,N'-Dimethyl-1,2-ethanediamine
DMF N,N-Dimethylformamide
DMSO-d$_6$ Hexadeuterodimethyl sulfoxide
EDCl 1-Ethyl-3-(3-Dimethylaminopropyl)carbodiimide
ESI Electrospray ionisation
Et$_2$O Diethylether
EtOH Ethanol
h Hour(s)
HCl Hydrogen chloride
HBr Hydrogen bromide
HOBT N-Hydroxybenzotriazole
HNO$_3$ Nitric acid
H$_2$SO$_4$ Sulfuric acid
K$_2$CO$_3$ Potassium carbonate
LCMS Liquid Chromatography-Mass Spectrometry
LiHMDS Lithium bis(trimethylsilyl)amide
MeOH Methanol
MgSO$_4$ Magnesium sulfate
min Minutes
NaCl Sodium chloride
NaHCO$_3$ Sodium bicarbonate
NaOH Sodium hydroxide
NaN$_3$ Sodium azide
NH$_4$SCN Ammonium thiocyanate
NH$_4$OH Ammonium hydroxide
NMR Nuclear magnetic resonance
Pd/C Palladium on carbon
PPh$_3$ Triphenylphosphine
SiO$_2$ Silica gel
SnCl$_2$.2H$_2$O Tin(II) chloride dihydrate
TosMIC p-Toluenesulfonylmethyl isocyanide
THF Tetrahydrofuran
TFA Trifluoroacetic acid
TEA Triethyamine
WT Wild type Experimental Procedure Example 025

Synthetic Approach of Example 025

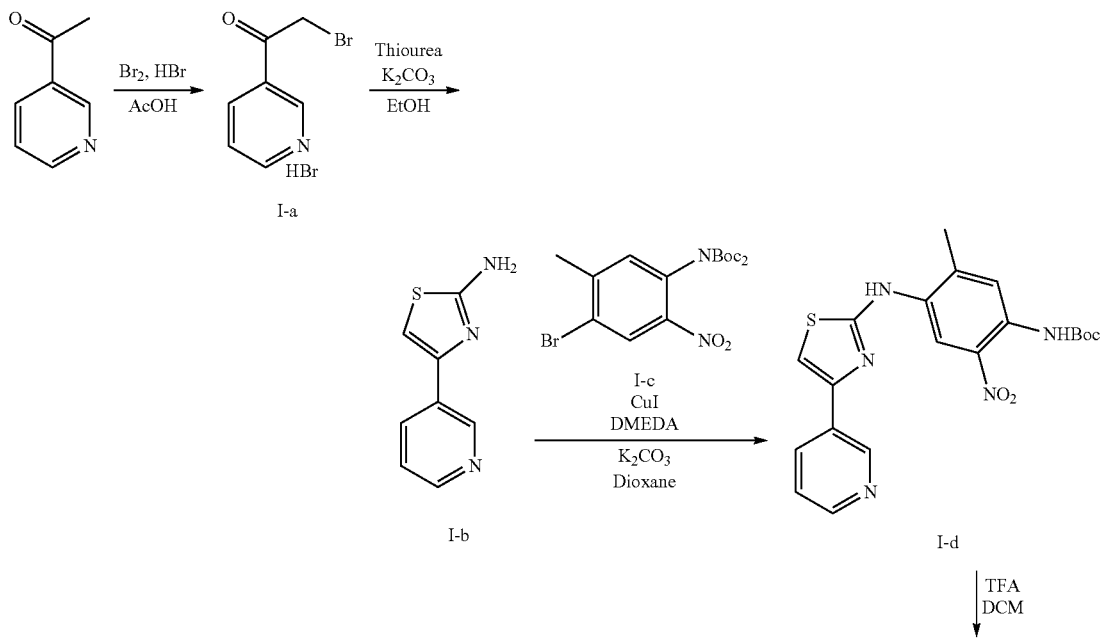

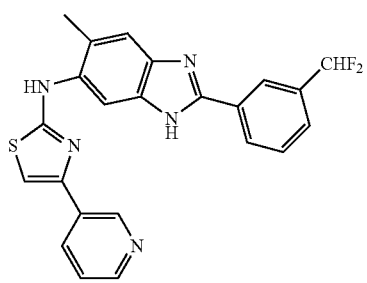
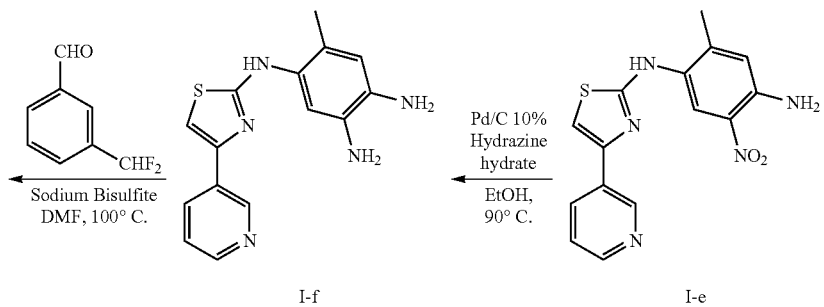

Preparation of 2-bromo-1-pyridin-3-yl-ethanone, HBr salt I-a

Bromine (24 g, 150 mmol) in 4 mL of 45% HBr was added dropwise under vigorous stirring to a solution at 70° C. of 3-acetyl-pyridine (18 g, 148 mmol) in acetic acid containing 45% of HBr (165 mL). The vigorously stirred mixture was kept at 70° C. for 3 h. The mixture was cooled and the precipitate collected by filtration and washed with petroleum ether/methanol (1/1, 100 mL) to give 35.8 g of a white crystals (85%). $^1$H NMR (300 MHz, DMSO-$d_6$) δ 12.77 (br s, 1H), 9.29 (m, 1H), 8.79-8.99 (m, 1H), 8.42-8.70 (m, 1H), 7.78-7.96 (m, 1H), 5.09 (s, 2H).

Preparation of 4-pyridin-3-yl-thiazol-2-ylamine I-b

To a solution of 2-bromo-1-pyridin-3-yl-ethanone Hydrobromide I-a (10 g, 35.58 mmol) in ethanol (100 mL) was added thiourea (2.98 g, 39.21 mmol), $K_2CO_3$ (9.83 g, 71.16 mmol) and the reaction mixture was refluxed for 5 h. After cooling to room temperature and evaporation of solvent, 150 mL of a saturated solution of $NaHCO_3$ was added and reaction mixture was stirred for 1 h. The precipitate was collected by filtration, washed by water and dried under vacuum to give the title compound I-b (6.2 g, 98%). $^1$H NMR (400 MHz, DMSO-$d_6$)$^1$H NMR (400 MHz, DMSO-$d_6$) δ 9.01 (d, J=2.0 Hz, 1H), 8.45 (dd, J=4.7, 1.5 Hz, 1H), 8.12 (dt, J=7.9, 1.9 Hz, 1H), 7.39 (dd, J=8.0, 4.8 Hz, 1H), 7.20 (s, 1H), 7.19 (s, 2H).

Preparation of 6-bromo-4-nitro-3-[bis-(tert-butoxycarbonyl)amino]toluene I-c NBS (2.87 g, 16.12 mmol) was added portionwise to a stirred solution of 5-methyl-2-nitroaniline (2.5 g, 16.45 mmol) in acetic acid (100 mL). The reaction mixture was heated under reflux for 1 h 30 min. After cooling, the reaction mixture was diluted with 1.2 L of water. The precipitate was filtered off, washed with water and dried under vacuum to give 4-bromo-5-methyl-2-nitro-phenylamine (3.52 g, 94%). $^1$H NMR (400 MHz, DMSO-$d_6$) δ 8.08 (s, 1H), 7.46 (s, 2H), 6.97 (s, 1H), 2.27 (s, 3H).

To a solution of 4-bromo-5-methyl-2-nitro-phenylamine (3.3 g, 14.29 mmol) and DMAP (180 mg) in DCM (70 mL) was added di-tert-butyl dicarbonate (6.30 g, 28.87 mmol). After stirring at room temperature for 24 h, water (40 mL) was added and the crude product was extracted with DCM and the organic layer was dried over $MgSO_4$ and concentrated. The final product was purified by silica gel chromatography using 30% EtOAc in cyclohexane as eluent to give compound I-c as a yellow solid (5.2 g, 92%). $^1$H NMR (400 MHz, DMSO-$d_6$) δ 8.36 (s, 1H), 7.67 (s, 1H), 2.45 (s, 3H), 1.35 (s, 18H).

Preparation of [5-methyl-2-nitro-4-(4-pyridin-3-yl-thiazol-2-ylamino)-phenyl]-carbamic acid tert-butyl ester I-d In a sealed tube were charged I-b (344 mg, 2 mmol), I-c (794 mg, 2 mmol), $K_2CO_3$ (552 mg, 4 mmol), CuI (100 mg, 0.52 mmol) and N,N'-Dimethyl-1,2-ethanediamine (118 µL, 1.04 mmol) in dry dioxane (10 mL). After stirring at 100° C. for 16 h, the reaction mixture was partitioned between saturated solution of NaCl (40 mL), $NH_4OH$ (8 mL) and EtOAc (60 mL). The organic layer was dried over $MgSO_4$ and concentrated. The obtained brown solid was purified by silica gel chromatography using 5% EtOH in DCM as eluent to give compound I-d as an orange solid (616 mg, 73%). $^1$H NMR (400 MHz, DMSO-$d_6$) δ 9.75 (s, 1H), 9.42 (s, 1H), 9.31 (s, 1H), 9.16 (s, 1H), 8.52 (d, J=4.6 Hz, 1H), 8.26 (d, J=8.1 Hz, 1H), 7.63 (s, 1H), 7.61 (s, 1H), 7.48 (dd, J=8.0, 4.6 Hz, 1H), 2.40 (s, 3H), 1.46 (s, 9H).

Preparation of 2-methyl-5-nitro-$N^1$-(4-pyridin-3-yl-thiazol-2-yl)-benzene-1,4-diamine I-e TFA (4 mL) was added dropwise to a stirred solution of I-d (600 mg, 1.40 mmol) in DCM (100 mL) and the resulting reaction mixture was stirred at room temperature for 2 h. Then, a solution of NaOH (5 N) was added until pH=9 and DCM evaporated. The resulting precipitate was filtered off to give I-e as a red solid (320 mg, 66%). $^1$H NMR (400 MHz, DMSO-$d_6$) δ 9.40 (s, 1H), 9.13 (s, 1H), 8.82 (s, 1H), 8.50 (d, J=4.5 Hz, 1H), 8.22 (d, J=8.0 Hz, 1H), 7.47 (s, 1H), 7.44 (dd, J=7.9, 4.6 Hz, 1H), 7.31 (s, 2H), 6.90 (s, 1H), 2.28 (s, 3H).

Preparation of 5-methyl-$N^4$-(4-pyridin-3-yl-thiazol-2-yl)-benzene-1,2,4-triamine I-f To a solution of I-e (164 mg, 0.5 mmol) in EtOH (8 mL) were added successively 10% Pd/C (20 mg) and dropwise hydrazine monohydrate (0.125 mL, 2.5 mmol). The reaction mixture was stirred at 80° C. for 16 h. Then, the hot mixture was filtrated over celite pad and washed with EtOH. The filtrate was concentrated under reduced pressure to give I-f as beige solid (102 mg, 69%). $^1$H NMR (400 MHz, DMSO-$d_6$) δ 9.06-9.02 (m, 1H), 9.01 (s, 1H), 8.47 (d, J=4.7 Hz, 1H), 8.15 (d, J=7.9 Hz, 1H), 7.41 (dd, J=7.9, 4.8 Hz, 1H), 7.21 (s, 1H), 6.59 (s, 1H), 6.41 (s, 1H), 4.43 (s, 2H), 4.40 (s, 2H), 2.02 (s, 3H).

Preparation of [2-(3-difluoromethyl-phenyl)-6-methyl-3H-benzoimidazol-5-yl]-(4-pyridin-3-yl-thiazol-2-yl)-amine 025

To a stirred solution of dianiline I-f (30 mg, 0.10 mmol) and 3-difluoromethyl-benzaldehyde (17 mg, 0.11 mmol) in DMF (1 mL) was added sodium bisulfite (30 mg, 0.29 mmol) and the reaction mixture was heated at 100° C. for 2 h. After cooling, a saturated solution of NaHCO$_3$ (3 mL) and AcOEt (5 mL) were added and the organic layer was washed with water, then with a saturated solution of NaCl, dried over MgSO$_4$ and concentrated. The crude product was purified by silica gel chromatography using 5% EtOH in DCM as eluent to give compound 025 as a beige solid (30 mg, 69%). $^1$H NMR (400 MHz, DMSO-d$_6$) δ 12.96 (br s, 1H), 9.46 (s, 1H), 9.14 (br s, 1H), 8.51 (d, J=3.8 Hz, 1H), 8.39 (s, 1H), 8.32 (d, J=7.2 Hz, 1H), 8.28-7.95 (m, 2H), 7.80-7.61 (m, 2H), 7.61-7.34 (m, 3H), 7.17 (t, J=55.8 Hz, 1H), 2.42 (s, 3H). LCMS: (ESI−) m/z 432 (M-H)$^-$ Retention time=2.08 mins.

Example 034

Compound 034 was prepared according to the synthetic approach described above.

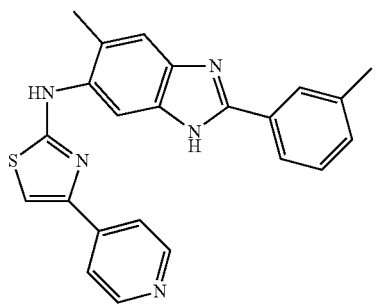

034

Preparation of 2-bromo-1-pyridin-4-yl-ethanone, HBr salt II-a

The title compound was prepared as described for intermediate I-a using Bromine (65 g, 410 mmol) in 93 mL of 45% aqueous HBr and 4-acetyl-pyridine (50 g, 410 mmol) in 11 ml of 45% aqueous HBr to give II-a as a white crystalline solid (77 g, 67%). $^1$H NMR (400 MHz, DMSO-d$_6$) δ 12.16 (s, 2H), 9.01 (dd, J=5.0, 1.5 Hz, 3H), 8.16 (dd, J=5.1, 1.3 Hz, 3H), 5.06 (s, 3H).

Preparation of 4-pyridin-4-yl-thiazol-2-ylamine II-b

The title compound was prepared as described for intermediate I-b using compound II-a (10 g, 35.58 mmol) and thiourea (2.98 g, 39.21 mmol) in 100 mL of EtOH. $^1$H NMR (400 MHz, DMSO-d$_6$) δ 8.55 (dd, J=4.6, 1.6 Hz, 2H), 7.73 (dd, J=4.6, 1.6 Hz, 2H), 7.39 (s, 1H), 7.21 (s, 2H).

Preparation of [5-Methyl-2-nitro-4-(4-pyridin-4-yl-thiazol-2-ylamino)-phenyl]-carbamic acid tert-butyl ester II-d The title compound was prepared as described for intermediate I-d using compound II-b (885 mg, 5 mmol), I-c (1.99 g, 5 mmol), K$_2$CO$_3$ (1.38 g, 10 mmol), CuI (250 mg, 1.30 mmol) and N,N'-Dimethyl-1,2-ethanediamine (295 μL, 2.60 mmol) in dry dioxane (25 mL). $^1$H NMR (400 MHz, DMSO-d$_6$) δ 9.75 (s, 1H), 9.40 (s, 1H), 9.28 (s, 1H), 8.62 (d, J=4.9 Hz, 2H), 7.88-7.82 (m, 2H), 7.80 (s, 1H), 7.64 (s, 1H), 2.39 (s, 3H), 1.47 (s, 9H).

Preparation of 2-methyl-5-nitro-N$^1$-(4-pyridin-4-yl-thiazol-2-yl)-benzene-1,4-diamine II-e The title compound was prepared as described for intermediate I-e using compound II-d (1 g, 2.34 mmol) and TFA (10 mL) in DCM (70 mL). $^1$H NMR (400 MHz, DMSO-d$_6$) δ 9.44 (s, 1H), 8.82 (s, 1H), 8.60 (d, J=6.0 Hz, 2H), 7.83 (d, J=6.1 Hz, 2H), 7.66 (s, 1H), 7.33 (s, 2H), 6.90 (s, 1H), 2.27 (s, 3H).

Preparation of 5-methyl-N$^4$-(4-pyridin-4-yl-thiazol-2-yl)-benzene-1,2,4-triamine II-f The title compound was prepared as described for intermediate I-f using compound II-e (415 mg, 1.27 mmol), 10% Pd/C (50 mg) and hydrazine monohydrate (0.316 mL, 6.33 mmol) in EtOH (20 mL). $^1$H NMR (400 MHz, DMSO-d$_6$) δ 9.05 (s, 1H), 8.56 (dd, J=4.5, 1.6 Hz, 2H), 7.76 (dd, J=4.5, 1.6 Hz, 2H), 7.41 (d, J=0.5 Hz, 1H), 6.59 (s, 1H), 6.41 (s, 1H), 4.45 (s, 2H), 4.42 (s, 2H), 2.01 (s, 3H).

Preparation of (6-methyl-2-m-tolyl-3H-benzoimidazol-5-yl)-(4-pyridin-4-yl-thiazol-2-yl)-amine 034

The title compound was prepared as described for compound 025 using compound II-f (40 mg, 0.135 mmol), 3-methyl-benzaldehyde (18 mg, 0.15 mmol) and sodium bisulfite (40 mg, 0.39 mmol) in DMF (1.5 mL). $^1$H NMR (400 MHz, DMSO-d$_6$) δ 12.79 (br s, 1H), 9.47 (br s, 1H), 8.60 (dd, J=4.6, 1.5 Hz, 2H), 8.05 (br s, 1H), 8.01 (s, 1H), 7.95 (d, J=7.8 Hz, 1H), 7.82 (dd, J=4.6, 1.5 Hz, 2H), 7.59 (s, 1H), 7.48 (s, 1H), 7.43 (t, J=7.7 Hz, 1H), 7.30 (d, J=7.5 Hz, 1H), 2.42 (s, 3H), 2.40 (s, 3H). LCMS: (ESI−) m/z 396 (M-H)$^-$, Retention time=1.79 mins.

Example 038

Synthetic Approach of Example 038

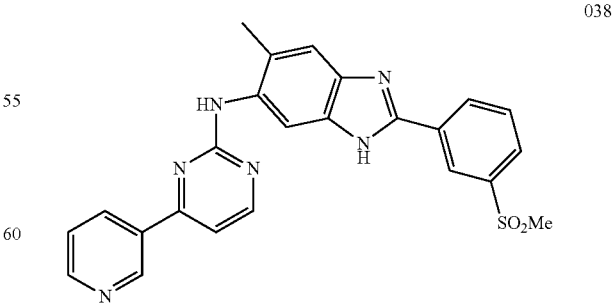

038

Compound 038 was prepared according to the synthetic approach described above using 4-pyridin-3-yl-pyrimidin-2-ylamine III-b.

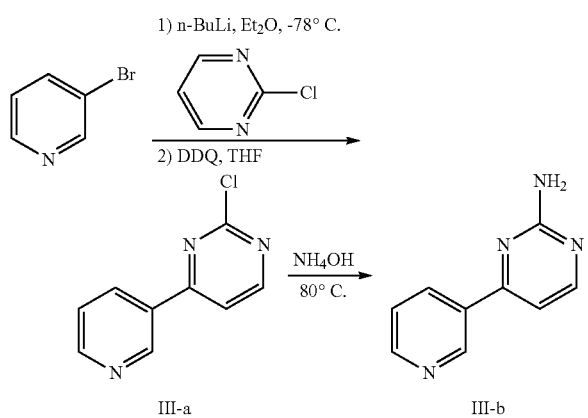

III-a    III-b

Preparation of 2-chloro-4-pyridin-3-yl-pyrimidine III-a

To a solution of n-butyllithium (2.5 molar in hexane, 13.5 mL, 34 mmol) in anhydrous diethylether (50 mL) under argon at −78° C. was added 3-bromo pyridine (3 mL, 31 mmol). The mixture was stirred for 1 h, then a suspension of 2-chloro pyrimidine (3.6 g, 31 mmol) in anhydrous diethylether (30 mL) was added portionwise over 10 min. The resulting mixture was stirred at −30° C. for 30 min, and then allowed to warm to 0° C. for 1 h, at which point the reaction was successively quenched by addition of water (1 mL) in THF (10 mL) and DDQ (7.6 g, 34 mmol) in THF (25 mL). The resulting brown suspension was stirred at room temperature for 15 min, then cooled to 0° C., and treated with hexane (25 mL) and aqueous NaOH (3N, 25 mL). The mixture was stirred at 0° C. for 5 min, diluted with water (100 mL) and then extracted with ethyl acetate. The combined organic layers were washed with water, dried on MgSO$_4$, and concentrated to a minimum volume to afford after filtration III-a as a pale brown solid (3.14 g, 53%). $^1$H NMR (400 MHz, DMSO-d$_6$) δ 9.35 (dd, J=2.3, 0.8 Hz, 1H), 8.90 (d, J=5.3 Hz, 1H), 8.79 (dd, J=4.8, 1.6 Hz, 1H), 8.54 (ddd, J=8.0, 2.3, 1.7 Hz, 1H), 8.26 (d, J=5.3 Hz, 1H), 7.62 (ddd, J=8.0, 4.8, 0.8 Hz, 1H).

Preparation of 4-pyridin-3-yl-pyrimidin-2-ylamine III-b

In a sealed tube, a solution of III-a (1.18 g, 6.16 mmol) in 30% NH$_4$OH (12 mL) was heated at 80° C. for 16 h. After cooling, the precipitate was isolated by filtration, washed with water and dried under vacuum to give the title compound III-b as a beige solid (925 mg, 87%). $^1$H NMR (400 MHz, DMSO-d$_6$) δ 9.23 (d, J=2.1 Hz, 1H), 8.69 (dd, J=4.7, 1.3 Hz, 1H), 8.43-8.38 (m, 1H), 8.36 (d, J=5.1 Hz, 1H), 7.53 (dd, J=8.0, 4.8 Hz, 1H), 7.21 (d, J=5.1 Hz, 1H), 6.76 (s, 2H).

Preparation of [5-methyl-2-nitro-4-(4-pyridin-3-yl-pyrimidin-2-ylamino)-phenyl]-carbamic acid tert-butyl ester III-d The title compound was prepared as described for intermediate I-d using compound III-b (250 mg, 1.45 mmol), I-c (570 mg, 1.32 mmol), K$_2$CO$_3$ (365 mg, 2.64 mmol), CuI (63 mg, 0.33 mmol) and N,N'-Dimethyl-1,2-ethanediamine (36 µL, 0.33 mmol) in dry dioxane (6.5 mL). $^1$H NMR (400 MHz, DMSO-d$_6$) δ 9.43 (s, 1H), 9.31 (br s, 1H), 9.15 (s, 1H), 8.72 (d, J=4.7 Hz, 1H), 8.59 (d, J=5.1 Hz, 1H), 8.53-8.39 (m, 2H), 7.62 (s, 1H), 7.60-7.48 (m, 2H), 2.37 (s, 3H), 1.47 (s, 9H).

Preparation of 2-methyl-5-nitro-N$^1$-(4-pyridin-3-yl-pyrimidin-2-yl)-benzene-1,4-diamine III-e The title compound was prepared as described for intermediate I-e using compound III-d (380 mg, 0.90 mmol) and TFA (5 mL) in DCM (15 mL). $^1$H NMR (400 MHz, DMSO-d$_6$) δ 9.25 (br s, 1H), 8.88 (br s, 1H), 8.70 (d, J=4.4 Hz, 1H), 8.50 (d, J=5.0 Hz, 1H), 8.42 (d, J=7.8 Hz, 1H), 8.17 (s, 1H), 7.60-7.49 (m, 1H), 7.43 (d, J=5.1 Hz, 1H), 7.31 (br s, 2H), 6.90 (s, 1H), 2.21 (s, 3H).

Preparation of 5-methyl-N$^4$-(4-pyridin-3-yl-pyrimidin-2-yl)-benzene-1,2,4-triamine III-f The title compound was prepared as described for intermediate I-f using compound III-e (242 mg, 0.75 mmol), 10% Pd/C (30 mg) and hydrazine monohydrate (1.5 mL) in EtOH (15 mL). $^1$H NMR (400 MHz, DMSO-d$_6$) δ 9.20 (br s, J=1.7 Hz, 1H), 8.67 (dd, J=4.8, 1.6 Hz, 1H), 8.48 (s, 1H), 8.45-8.30 (m, 2H), 7.52 (dd, J=8.0, 4.8 Hz, 1H), 7.25 (d, J=5.1 Hz, 1H), 6.54 (s, 1H), 6.38 (s, 1H), 4.28 (br s, 4H), 1.97 (s, J=6.7 Hz, 3H).

Preparation of [2-(3-methanesulfonyl-phenyl)-6-methyl-3H-benzoimidazol-5-yl]-(4-pyridin-3-yl-pyrimidin-2-yl)-amine 038

The title compound was prepared as described for compound 038 using compound III-f (32 mg, 0.11 mmol), 3-methanesulfonyl-benzaldehyde (22 mg, 0.12 mmol) and sodium bisulfite (32 mg) in DMF (1.5 mL). $^1$H NMR (400 MHz, DMSO-d$_6$) δ 13.05 (br s, 1H), 9.26 (s, 1H), 8.95 (s, 1H), 8.70 (d, J=5.1 Hz, 2H), 8.49 (d, J=7.1 Hz, 2H), 8.41 (d, J=7.4 Hz, 1H), 8.03 (d, J=7.8 Hz, 1H), 7.84 (t, J=7.8 Hz, 1H), 7.79 (s, 1H), 7.62-7.31 (m, 3H), 3.26 (s, 3H), 2.38 (s, 3H). LCMS: (ESI−) m/z 455 (M-H)$^-$, Retention time=1.87 mins.

Example 055

Synthetic Approach of Example 055

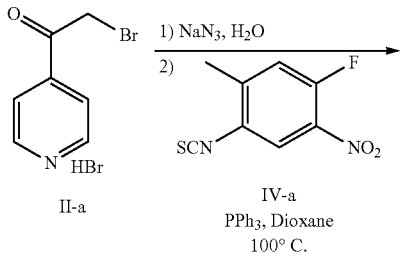

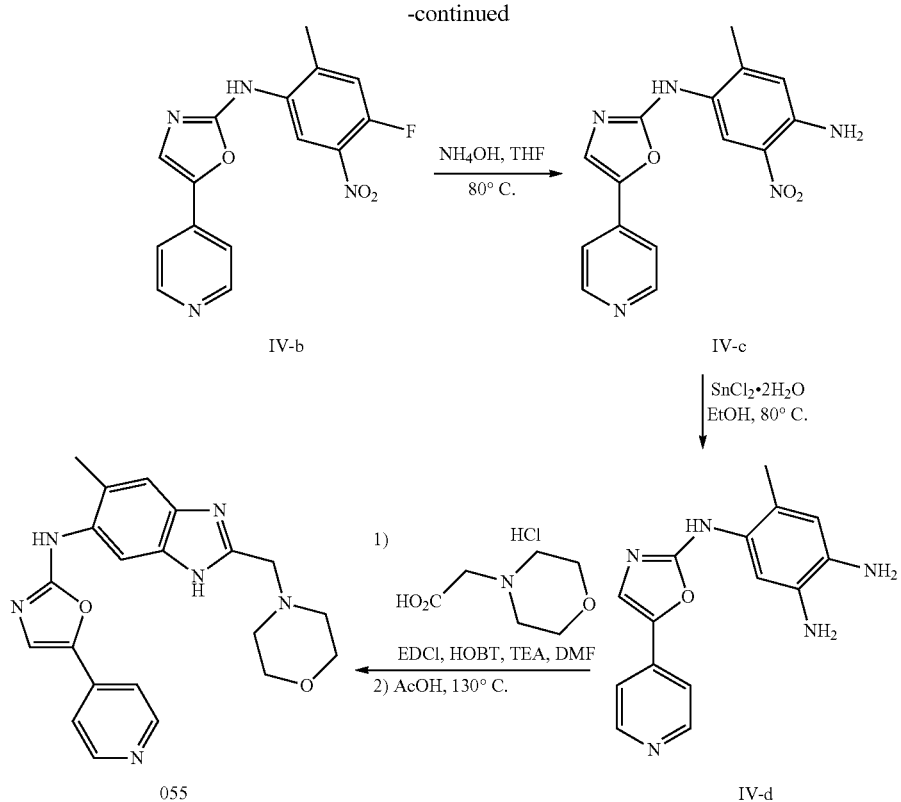

Preparation of 1-fluoro-4-isothiocyanato-5-methyl-2-nitro-benzene IV-a

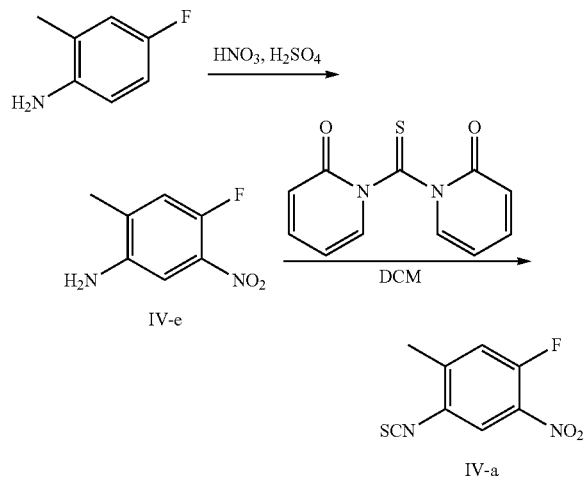

Fuming nitric acid (3.35 mL, 84 mmol) in concentrated sulfuric acid (10 mL) was added dropwise to a −5° C. cooled solution of 4-fluoro-2-methyl-phenylamine (10.5 g, 84 mmol) in 90 mL of concentrated sulfuric acid. The reaction mixture was stirred at 0° C. for 2 h and cold water added (300 mL). Then, a cold solution of NaOH (10 N) was slowly added until pH=10 and the resultant precipitate was filtered off to give intermediate IV-e as yellow solid (12.7 g, 89%).

$^1$H NMR (400 MHz, DMSO-$d_6$) δ 7.30 (d, J=6.8 Hz, 1H), 7.17 (d, J=12.3 Hz, 1H), 5.39 (s, 2H), 2.14 (s, 3H).

To a solution of IV-e (600 mg, 3.53 mmol) in DCM (40 mL) was added 1,1'-Thiocarbonyldi-2(1H)-pyridone (232 mg, 3.88 mmol) and the reaction mixture was stirred for 4 h. After evaporation of solvent the resulting crude product was purified by silica gel chromatography using 25% AcOEt in cyclohexane as eluent to give 1-fluoro-4-isothiocyanato-5-methyl-2-nitro-benzene IV-a as a yellow syrup (740 mg, 99%).

Preparation of (4-fluoro-2-methyl-5-nitro-phenyl)-(5-pyridin-4-yl-oxazol-2-yl)-amine IV-b To a stirred solution of 4-bromoacetylpyridine hydrobromide II-a (1.2 g, 4.27 mmol) in 20 mL of water was added portionwise sodium azide (305 mg, 4.69 mmol). The reaction mixture was stirred at room temperature for 2 h and treated with saturated aqueous NaHCO$_3$ until pH=7. The resultant mixture was extracted with DCM and the combined organic layers were concentrated under vacuum at room temperature to give 4-azidoacetylpyridine as a brown syrup which was used without further purification. To a solution of 4-azidoacetylpyridine in dioxane 35 mL was added 1-fluoro-4-isothiocyanato-5-methyl-2-nitro-benzene IV-a (760 mg, 3.55 mmol) and triphenylphosphine (931 mg, 3.55 mmol). The reaction mixture was heated to 100° C. for 45 min. After cooling the precipitate was isolated by filtration and washed with AcOEt to give the title compound IV-b as yellow solid (552 mg, 50%). $^1$H NMR (400 MHz, DMSO-$d_6$) δ 9.97 (s, 1H), 8.87 (d, J=7.0 Hz, 1H), 8.71-8.53 (m, 2H), 7.87-7.82 (m, 1H), 7.58-7.47 (m, 3H), 2.43 (s, 3H).

Preparation of 2-methyl-5-nitro-$N^1$-(5-pyridin-4-yl-oxazol-2-yl)-benzene-1,4-diamine IV-c In a sealed tube a solution of IV-b (500 mg, 1.59 mmol) and 30% NH$_4$OH (10 mL) in THF (10 mL) was heated at 80° C. for 16 h. After cooling and evaporation of THF under vacuum, the precipitate was isolated by filtration and washed with water to give the title compound IV-c as yellow solid (420 mg, 88%). $^1$H NMR (400 MHz, DMSO-d$_6$) δ 9.51 (br s, 1H), 8.56 (d, J=6.2 Hz, 2H), 8.41 (s, 1H), 7.76 (s, 1H), 7.47 (d, J=6.1 Hz, 2H), 7.31 (s, 2H), 6.89 (s, 1H), 2.26 (s, 3H).

Preparation of 5-methyl-$N^4$-(5-pyridin-4-yl-oxazol-2-yl)-benzene-1,2,4-triamine IV-d A mixture of compound IV-c (400 mg, 1.29 mmol) and tin(II) chloride dihydrate (1.46 g, 6.45 mmol) in ethanol (30 mL) was heated under reflux for 16 h. The reaction mixture was cooled to room temperature, concentrated and saturated aqueous NaHCO$_3$ was added dropwise until pH=8. The resultant suspension was extracted with hot AcOEt and the combined organic layers were washed with water, saturated solution of NaCl, dried over MgSO$_4$ and concentrated. The crude product was purified by silica gel chromatography using DCM/EtOH/NH$_4$OH: 90/9/1 as eluent to give the title compound IV-d as a yellow solid (220 mg, 61%). $^1$H NMR (300 MHz, DMSO-d$_6$) δ 9.05 (s, 1H), 8.50 (dd, J=4.7, 1.4 Hz, 2H), 7.64 (s, 1H), 7.38 (dd, J=4.7, 1.5 Hz, 2H), 6.65 (s, 1H), 6.36 (s, 1H), 4.36 (s, 4H), 2.01 (s, 3H).

Preparation of (6-methyl-2-morpholin-4-ylmethyl-3H-benzoimidazol-5-yl)-(5-pyridin-4-yl-oxazol-2-yl)-amine 055

A mixture of dianiline IV-d (40 mg, 0.14 mmol), morpholin-4-yl-acetic acid hydrochloride (28 mg, 0.15 mmol), 1-hydroxybenzotriazole hydrate (21 mg, 0.16 mmol), N-(3-dimethylaminopropyl)-N'-ethylcarbodiimide hydrochloride (30 mg, 0.16 mmol) and triethylamine (40 μL, 0.32 mmol) in DMF (2 mL) was stirred at room temperature overnight. The reaction mixture was then evaporated, diluted with ethyl acetate, washed with water, dried over MgSO$_4$, and concentrated. The residue was dissolved in AcOH (1 mL) and heated at 130° C. for 15 min. After cooling, a saturated solution of NaHCO$_3$ (10 mL) and AcOEt (10 mL) were added and the organic layer was washed with water, then with a saturated solution of NaCl, dried over MgSO$_4$ and concentrated. The crude product was purified by silica gel chromatography using 5% EtOH in DCM as eluent to give compound 055 as a yellow solid (17 mg, 31%). $^1$H NMR (400 MHz, DMSO-d$_6$) δ 12.25 (br s, 1H), 9.48 (s, 1H), 8.55 (d, J=6.0 Hz, 2H), 7.82 (s, 1H), 7.74 (s, 1H), 7.46 (d, J=6.1 Hz, 2H), 7.36 (s, 1H), 3.72 (s, 2H), 3.67-3.52 (m, 4H), 2.50-2.43 (m, 4H), 2.36 (s, 3H). LCMS: (ESI−) m/z 389 (M-H)$^−$, Retention time=1.17 mins.

Example 076

Synthetic Approach of Example 076

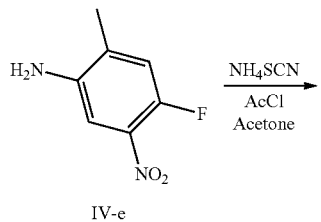

IV-e

V-a

V-b

1) NH$_4$OH, THF
   80° C.
2) SnCl$_2$·2H$_2$O
   EtOH, 80° C.

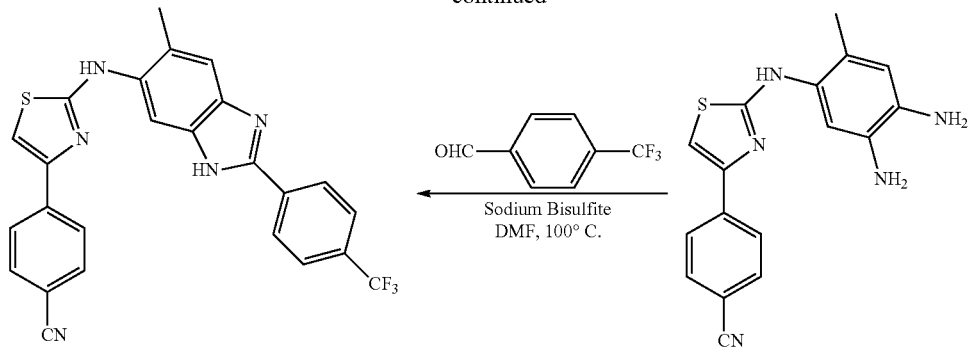

Preparation of 1-acetyl-3-(4-fluoro-2-methyl-5-nitro-phenyl)-thiourea V-a

To a solution of ammonium thiocyanate (805 mg, 10.6 mmol) in acetone (15 mL) was added dropwise AcCl (0.76 mL, 10.6 mmol). The reaction mixture was heated at 60° C. for 1 h. After cooling a solution of compound IV-e (1.5 g, 8.82 mmol) in acetone (5 mL) was added and the reaction mixture stirred for 2 h at room temperature. Water (60 mL) was added and the mixture was stirred for 1 h. The precipitate filtered, washed with water and dried under vacuum to give the title compound V-a (2.05 g, 86%). $^{1}$H NMR (400 MHz, DMSO-$d_6$) δ 12.20 (s, 1H), 11.67 (s, 1H), 8.48 (d, J=7.4 Hz, 1H), 7.59 (d, J=12.2 Hz, 1H), 2.31 (s, 3H), 2.18 (s, 3H).

Preparation of 4-[2-(4-fluoro-2-methyl-5-nitro-phenylamino)-thiazol-4-yl]-benzonitrile V-b A solution of compound V-a (1 g, 3.7 mmol) and potassium carbonate (1.03 g, 7.4 mmol) in methanol (15 mL) was stirred at room temperature for 1 h. 4-(2-Bromo-acetyl)-benzonitrile (911 mg, 4.07 mmol) was then added and the reaction mixture stirred for 3 h. Water (100 mL) was added and the precipitate filtered, washed with water and dried under vacuum to give the title compound V-b as a yellow solid (1.11 g, 85%).

Preparation of 4-[2-(4-amino-2-methyl-5-nitro-phenylamino)-thiazol-4-yl]-benzonitrile V-c The title compound was prepared as described for compound IV-c using compound V-b (1 g, 2.82 mmol), 30% NH$_4$OH (20 mL) and THF (20 mL). $^{1}$H NMR (400 MHz, DMSO-$d_6$) δ 9.42 (s, 1H), 8.77 (s, 1H), 8.07 (d, J=8.4 Hz, 2H), 7.87 (d, J=8.5 Hz, 2H), 7.60 (s, 1H), 7.33 (s, 2H), 6.90 (s, 1H), 2.27 (s, 3H).

Preparation of 4-[2-(4,5-diamino-2-methyl-phenylamino)-thiazol-4-yl]-benzonitrile V-d The title compound was prepared as described for compound IV-d using compound V-c (700 mg, 2.18 mmol), tin(II) chloride dihydrate (2.46 g, 10.9 mmol) in ethanol (80 mL). $^{1}$H NMR (400 MHz, DMSO-$d_6$) δ 9.01 (s, 1H), 8.00 (d, J=8.1 Hz, 2H), 7.82 (d, J=8.0 Hz, 2H), 7.34 (s, 1H), 6.58 (s, 1H), 6.40 (s, 1H), 4.43 (s, 2H), 4.40 (s, 2H), 2.00 (s, 3H).

Preparation of 4-{2-[6-methyl-2-(4-trifluoromethyl-phenyl)-3H-benzoimidazol-5-ylamino]-thiazol-4-yl}-benzonitrile 076

The title compound was prepared as described for compound 025 using compound V-d (80 mg, 0.25 mmol), 4-trifluoromethyl-benzaldehyde (49 mg, 0.28 mmol) and sodium bisulfite (70 mg, 0.67 mmol) in DMF (2.5 mL). LCMS: (ESI−) m/z=474 (M-H)$^{-}$, Retention time=3.25 mins.

Example 117

Synthetic Approach of Example 117

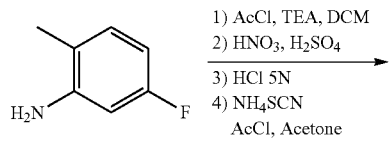

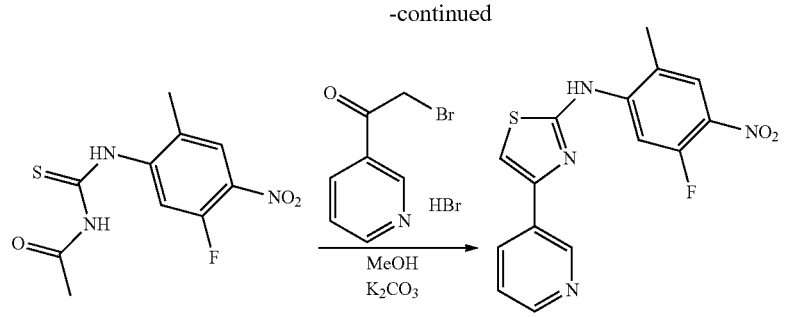

VI-a

VI-b

1) MeNH₂, THF
2) Hydrazine hydrate
   Pd/C 10%, EtOH

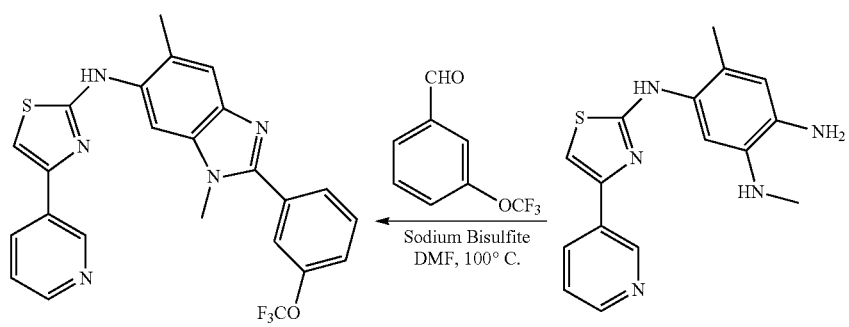

117

VI-d

Preparation of N-(5-Fluoro-2-methyl-phenyl)-acetamide VI-e

Preparation of N-(5-Fluoro-2-methyl-4-nitro-phenyl)-acetamide VI-f

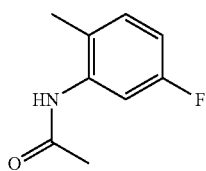

VI-e

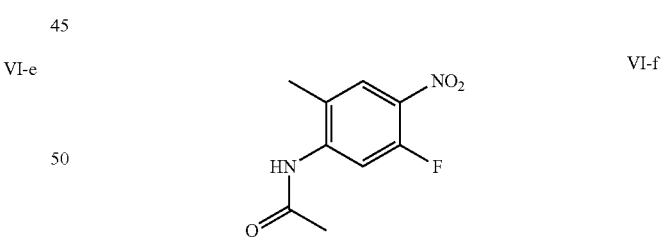

VI-f

To a solution of 5-Fluoro-2-methyl-phenylamine (12.5 g, 0.1 mmol) in DCM (600 mL) were successively added TEA (30.5 mL, 0.22 mmol) and dropwise at 0° C. AcCl (14.3 mL, 0.2 mmol). After stirring at room temperature for 24 h, water (400 mL) was added and the organic layer was dried over MgSO₄ and concentrated. The obtained crude solid was triturated with cyclohexane, to afford 14.5 g (86%) of the title compound as yellow crystals. ¹H NMR (400 MHz, DMSO-d₆) δ 9.31 (s, 1H), 7.43 (dd, J=11.0, 1.9 Hz, 1H), 7.21 (t, J=7.5 Hz, 1H), 6.88 (dt, J=8.3, 2.3 Hz, 1H), 2.19 (s, 3H), 2.09 (s, 3H).

To a solution of N-(5-Fluoro-2-methyl-phenyl)-acetamide VI-e (13.1 g, 79.4 mmol) in sulfuric acid (75 mL) was added dropwise at 0° C. a solution of 70% nitric acid (7.17 g, d=1.42). After stirring 1 h at 0° C., the reaction mixture was poured dropwise into 1 l of ice water. The precipitate was filtered, washed with water and dissolved in EtOAc (750 mL). The organic solution was washed successively with a saturated solution of NaHCO₃ and NaCl, dried over MgSO₄ and concentrated to afford the compound VI-f as yellow solid (12.6 g, 75%). ¹H NMR (400 MHz, DMSO-d₆) δ 9.57 (br s, 1H), 8.23-7.94 (m, 2H), 2.32 (s, 3H), 2.19 (s, 3H).

Preparation of 5-Fluoro-2-methyl-4-nitro-phenylamine VI-g

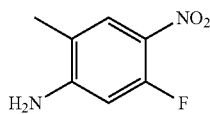

N-(5-Fluoro-2-methyl-4-nitro-phenyl)-acetamide VI-f (12.6 g) in 5N HCl (150 mL) was heated under reflux for 1 h 30 min. The reaction mixture was cooling and a 32% aqueous NaOH solution was added dropwise until pH=8-9. The crude product was extracted with EtOAc (2 times) and the organic layer was washed with water, then with a saturated solution of NaCl, dried over MgSO4 and concentrated to give VI-g as yellow solid (9.1 g, 94%). $^1$H NMR (400 MHz, DMSO-$d_6$) δ 7.80 (d, J=8.7 Hz, 1H), 6.72 (br s, 2H), 6.45 (d, J=14.5 Hz, 1H), 2.07 (s, 3H).

Preparation of 1-acetyl-3-(4-fluoro-2-methyl-5-nitro-phenyl)-thiourea VI-a

The title compound was prepared as described for intermediate V-a using compound VI-g (3 g, 17.64 mmol), ammonium thiocyanate (1.61 g, 21.15 mmol), AcCl (1.52 mL, 21.15 mmol) and acetone (50 mL).

Preparation of (5-Fluoro-2-methyl-4-nitro-phenyl)-(4-pyridin-3-yl-thiazol-2-yl)-amine VI-b The title compound was prepared as described for intermediate V-b using compound VI-a (3.3 g, 12.92 mmol), potassium carbonate (1.03 g, 51.68 mmol), 2-bromo-1-pyridin-3-yl-ethanone, HBr salt I-a (4 g, 14.21 mmol) and MeOH (50 mL).

Preparation of Preparation of N1-methyl-4-methyl-6-nitro-N3-(4-pyridin-3-yl-thiazol-2-yl)-benzene-1,3-diamine VI-c The title compound VI-c was prepared as described for compound IV-c using compound VI-b (1 g, 3.03 mmol), MeNH$_2$ (2M in THF, 10 mL) and THF (10 mL). $^1$H NMR (400 MHz, DMSO-$d_6$) δ 9.84 (s, 1H), 9.18 (d, J=1.7 Hz, 1H), 8.64-8.46 (m, 1H), 8.42 (s, 1H), 8.36-8.13 (m, 2H), 7.91 (s, 1H), 7.76 (s, 1H), 7.48 (dd, J=7.9, 4.8 Hz, 1H), 3.06 (d, J=4.9 Hz, 3H), 2.28 (s, 3H).

Preparation of Preparation of (5-Fluoro-2-methyl-4-nitro-phenyl)-(4-pyridin-3-yl-thiazol-2-yl)-amine VI-d The title compound VI-d was prepared as described for compound I-f using compound VI-c (490 mg, 1.44 mmol), 10% Pd/C (65 mg), hydrazine monohydrate (0.358 mL) and EtOH (25 mL). $^1$H NMR (400 MHz, DMSO-$d_6$) δ 9.13 (s, 1H), 9.05 (s, 1H), 8.47 (d, J=4.1 Hz, 1H), 8.15 (d, J=7.8 Hz, 1H), 7.46-7.32 (m, 1H), 7.23 (s, 1H), 6.50 (s, 1H), 6.43 (s, 1H), 4.63-4.54 (m, 1H), 4.49 (s, 2H), 2.68 (d, J=4.5 Hz, 3H), 2.05 (s, 3H).

Preparation of [3,6-Dimethyl-2-(3-trifluoromethoxyphenyl)-3H-benzoimidazol-5-yl]-(4-pyridin-3-yl-thiazol-2-yl)-amine 117

The title compound was prepared as described for compound 025 using compound VI-d (50 mg, 0.161 mmol), 3-trifluoromethoxy-benzaldehyde (34 mg, 0.177 mmol) and sodium bisulfite (48 mg, 0.47 mmol) in DMF (1.5 mL). $^1$H NMR (400 MHz, DMSO-$d_6$) δ 9.58 (s, 1H), 9.12 (s, 1H), 8.50 (d, J=3.6 Hz, 1H), 8.35-8.08 (m, 2H), 7.92 (d, J=7.7 Hz, 1H), 7.86 (s, 1H), 7.73 (t, J=7.9 Hz, 1H), 7.61 (s, 1H), 7.57 (d, J=8.1 Hz, 1H), 7.49-7.38 (m, 2H), 3.90 (s, 3H), 2.42 (s, 3H). LCMS: (ESI-) m/z=480 (M-H)$^-$, Retention time=2.53 mins.

Example 114

Compound 114 was prepared according the synthetic approach described above for compound 076.

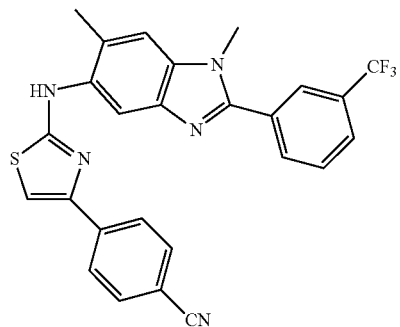

Preparation of 4-[2-(2-Methyl-4-methylamino-5-nitro-phenylamino)-thiazol-4-yl]-benzonitrile VII-a The title compound VII-a was prepared as described for compound IV-c using compound V-b (2.60 g, 7.33 mmol), MeNH$_2$ (2M in THF, 20 mL) and THF (20 mL).

Preparation of 4-[2-(5-Amino-2-methyl-4-methyl-amino-phenylamino)-thiazol-4-yl]-benzonitrile VII-b The title compound VII-b was prepared as described for compound IV-d using compound VII-a (1.23 g, 3.37 mmol), tin(II) chloride dihydrate (7.60 g, 33.7 mmol) in ethanol (100 mL). $^1$H NMR (400 MHz, DMSO-$d_6$) δ 9.05 (s, 1H), 8.01 (d, J=8.4 Hz, 2H), 7.83 (d, J=8.4 Hz, 2H), 7.35 (s, 1H), 6.61 (s, 1H), 6.27 (s, 1H), 4.60 (d, J=5.0 Hz, 1H), 4.43 (s, 2H), 2.73 (d, J=4.9 Hz, 3H), 2.09 (s, 3H).

Preparation of 4-{2-[1,6-Dimethyl-2-(3-trifluoromethyl-phenyl)-1H-benzoimidazol-5-ylamino]-thiazol-4-yl}-benzonitrile 114

The title compound was prepared as described for compound 025 using compound VII-b (66 mg, 0.2 mmol), 3-trifluoromethyl-benzaldehyde (38 mg, 0.22 mmol) and sodium bisulfite (62 mg, 0.6 mmol) in DMF (5 mL). $^1$H NMR (400 MHz, DMSO-$d_6$) δ 9.49 (s, 1H), 8.18 (d, J=7.2 Hz, 2H), 8.08 (s, 1H), 8.04 (d, J=8.2 Hz, 2H), 7.93 (d, J=7.6 Hz, 1H), 7.90-7.78 (m, 3H), 7.57 (s, 1H), 7.51 (s, 1H), 3.91 (s, 3H), 2.45 (s, 3H). LCMS: (ESI-) m/z=488 (M-H)-, Retention time=3.39 mins.

Other compounds were prepared according to the most appropriate synthetic approach described above with appropriate reactants to lead to the specific compound referred to.

In another aspect, the invention relates to compositions, in particular to a pharmaceutical composition, comprising at least one compound as depicted above.

Such a pharmaceutical composition can be adapted for oral administration, and can be formulated using pharmaceutically acceptable carriers well known in the art in suitable dosages. Such carriers enable the pharmaceutical compositions to be formulated as tablets, pills, dragees, capsules, liquids, gels, syrups, slurries, suspensions, and the like, for ingestion by the patient. In addition to the active ingredients, these pharmaceutical compositions may contain suitable pharmaceutically-acceptable carriers comprising excipients and auxiliaries which facilitate processing of the active compounds into preparations which can be used pharmaceutically. Further details on techniques for formulation and administration may be found in the latest edition of Remington's Pharmaceutical Sciences (Maack Publishing Co., Easton, Pa.).

The composition of the invention can also take the form of a pharmaceutical or cosmetic composition for topical administration.

Such compositions may be presented in the form of a gel, paste, ointment, cream, lotion, liquid suspension aqueous, aqueous-alcoholic or, oily solutions, or dispersions of the lotion or serum type, or anhydrous or lipophilic gels, or emulsions of liquid or semi-solid consistency of the milk type, obtained by dispersing a fatty phase in an aqueous phase or vice versa, or of suspensions or emulsions of soft, semi-solid consistency of the cream or gel type, or alternatively of microemulsions, of microcapsules, of microparticles or of vesicular dispersions to the ionic and/or nonionic type. These compositions are prepared according to standard methods.

The composition according to the invention comprises any ingredient commonly used in dermatology and cosmetic. It may comprise at least one ingredient selected from hydrophilic or lipophilic gelling agents, hydrophilic or lipophilic active agents, preservatives, emollients, viscosity enhancing polymers, humectants, surfactants, preservatives, antioxidants, solvents, and fillers, antioxidants, solvents, perfumes, fillers, screening agents, bactericides, odor absorbers and coloring matter.

As oils which can be used in the invention, mineral oils (liquid paraffin), vegetable oils (liquid fraction of shea butter, sunflower oil), animal oils, synthetic oils, silicone oils (cyclomethicone) and fluorinated oils may be mentioned. Fatty alcohols, fatty acids (stearic acid) and waxes (paraffin, carnauba, beeswax) may also be used as fatty substances.

As emulsifiers, glycerols, polysorbates, glycerides, and PEGs can be used in the invention.

As hydrophilic gelling agents, carboxyvinyl polymers (carbomer), acrylic copolymers such as acrylate/alkylacrylate copolymers, polyacrylamides, polysaccharides such as hydroxypropylcellulose, clays and natural gums may be mentioned, and as lipophilic gelling agents, modified clays such as bentones, metal salts of fatty acids such as aluminum stearates and hydrophobic silica, or alternatively ethylcellulose and polyethylene may be mentioned.

As hydrophilic active agents, proteins or protein hydrolysates, amino acids, polyols, urea, allantoin, sugars and sugar derivatives, vitamins, starch and plant extracts, in particular those of Aloe vera may be used.

As lipophilic active, agents, retinol (vitamin A) and its derivatives, tocopherol (vitamin E) and its derivatives, essential fatty acids, ceramides and essential oils may be used. These agents add extra moisturizing or skin softening features when utilized.

In addition, a surfactant can be included in the composition so as to provide deeper penetration of the compound capable of depleting mast cells, such as a tyrosine kinase inhibitor, preferably a c-kit inhibitor.

Among the contemplated ingredients, the invention embraces penetration enhancing agents selected for example from the group consisting of mineral oil, water, ethanol, triacetin, glycerin and propylene glycol; cohesion agents selected for example from the group consisting of polyisobutylene, polyvinyl acetate and polyvinyl alcohol, and thickening agents.

Chemical methods of enhancing topical absorption of drugs are well known in the art. For example, compounds with penetration enhancing properties include sodium lauryl sulfate (Dugard, P. H. and Sheuplein, R. J., "Effects of Ionic Surfactants on the Permeability of Human Epidermis: An Electrometric Study," J. Ivest. Dermatol., V.60, pp. 263-69, 1973), lauryl amine oxide (Johnson et. al., U.S. Pat. No. 4,411,893), azone (Rajadhyaksha, U.S. Pat. Nos. 4,405,616 and 3,989,816) and decylmethyl sulfoxide (Sekura, D. L. and Scala, J., "The Percutaneous Absorption of Alkylmethyl Sulfides," Pharmacology of the Skin, Advances In Biolocy of Skin, (Appleton-Century Craft) V. 12, pp. 257-69, 1972). It has been observed that increasing the polarity of the head group in amphoteric molecules increases their penetration-enhancing properties but at the expense of increasing their skin irritating properties (Cooper, E. R. and Berner, B., "Interaction of Surfactants with Epidermal Tissues: Physiochemical Aspects," Surfactant Science Series, V. 16, Reiger, M. M. ed. (Marcel Dekker, Inc.) pp. 195-210, 1987).

A second class of chemical enhancers are generally referred to as co-solvents. These materials are absorbed topically relatively easily, and, by a variety of mechanisms, achieve permeation enhancement for some drugs. Ethanol (Gale et. al., U.S. Pat. No. 4,615,699 and Campbell et. al., U.S. Pat. Nos. 4,460,372 and 4,379,454), dimethyl sulfoxide (U.S. Pat. Nos. 3,740,420 and 3,743,727, and U.S. Pat. No. 4,575,515), and glycerine derivatives (U.S. Pat. No. 4,322, 433) are a few examples of compounds which have shown an ability to enhance the absorption of various compounds.

This invention covers medical devices comprising a composition of the invention.

The pharmaceutical compositions of the invention can also be intended for administration as an aerosolized formulation to target areas of a patient's respiratory tract.

Devices and methodologies for delivering aerosolized bursts of a formulation of a drug are disclosed in U.S. Pat. No. 5,906,202. Formulations are preferably solutions, e.g. aqueous solutions, ethanoic solutions, aqueous/ethanoic solutions, saline solutions, colloidal suspensions and microcrystalline suspensions. For example aerosolized particles comprise the active ingredient mentioned above and a carrier, (e.g., a pharmaceutically active respiratory drug and carrier) which are formed upon forcing the formulation through a nozzle which nozzle is preferably in the form of a flexible porous membrane. The particles have a size which is sufficiently small such that when the particles are formed they remain suspended in the air for a sufficient amount of time such that the patient can inhale the particles into the patient's lungs.

The invention encompasses the systems described in U.S. Pat. No. 5,556,611:
   liquid gas systems (a liquefied gas is used as propellent gas (e.g. low-boiling FCHC or propane, butane) in a pressure container,
   suspension aerosol (the active substance particles are suspended in solid form in the liquid propellent phase), pressurized gas system (a compressed gas such as nitrogen, carbon dioxide, dinitrogen monoxide, air is used.

Thus, according to the invention the pharmaceutical preparation is made in that the active substance is dissolved or dispersed in a suitable nontoxic medium and said solution or dispersion atomized to an aerosol, i.e. distributed extremely finely in a carrier gas. This is technically possible for example in the form of aerosol propellent gas packs, pump aerosols or other devices known per se for liquid misting and solid atomizing which in particular permit an exact individual dosage.

Therefore, the invention is also directed to aerosol devices comprising the compound as defined above and such a formulation, preferably with metered dose valves.

The pharmaceutical compositions of the invention can also be intended for intranasal administration.

In this regard, pharmaceutically acceptable carriers for administering the compound to the nasal mucosal surfaces will be readily appreciated by the ordinary artisan. These carriers are described in the Remington's Pharmaceutical Sciences" 16th edition, 1980, Ed. By Arthur Osol, the disclosure of which is incorporated herein by reference.

The selection of appropriate carriers depends upon the particular type of administration that is contemplated. For administration via the upper respiratory tract, the composition can be formulated into a solution, e.g., water or isotonic saline, buffered or unbuffered, or as a suspension, for intranasal administration as drops or as a spray. Preferably, such solutions or suspensions are isotonic relative to nasal secretions and of about the same pH, ranging e.g., from about pH 4.0 to about pH 7.4 or, from pH 6.0 to pH 7.0. Buffers should be physiologically compatible and include, simply by way of example, phosphate buffers. For example, a representative nasal decongestant is described as being buffered to a pH of about 6.2 (Remington's, Id. at page 1445). Of course, the ordinary artisan can readily determine a suitable saline content and pH for an innocuous aqueous carrier for nasal and/or upper respiratory administration.

Common intranasal carriers include nasal gels, creams, pastes or ointments with a viscosity of, e.g., from about 10 to about 3000 cps, or from about 2500 to 6500 cps, or greater, may also be used to provide a more sustained contact with the nasal mucosal surfaces. Such carrier viscous formulations may be based upon, simply by way of example, alkylcelluloses and/or other biocompatible carriers of high viscosity well known to the art (see e.g., Remington's, cited supra. A preferred alkylcellulose is, e.g., methylcellulose in a concentration ranging from about 5 to about 1000 or more mg per 100 ml of carrier. A more preferred concentration of methyl cellulose is, simply by way of example, from about 25 mg to about 150 mg per 100 ml of carrier.

Other ingredients, such as art known preservatives, colorants, lubricating or viscous mineral or vegetable oils, perfumes, natural or synthetic plant extracts such as aromatic oils, and humectants and viscosity enhancers such as, e.g., glycerol, can also be included to provide additional viscosity, moisture retention and a pleasant texture and odor for the formulation. For nasal administration of solutions or suspensions according to the invention, various devices are available in the art for the generation of drops, droplets and sprays.

A premeasured unit dosage dispenser including a dropper or spray device containing a solution or suspension for delivery as drops or as a spray is prepared containing one or more doses of the drug to be administered and is another object of the invention. The invention also includes a kit containing one or more unit dehydrated doses of the compound, together with any required salts and/or buffer agents, preservatives, colorants and the like, ready for preparation of a solution or suspension by the addition of a suitable amount of water.

Another aspect of the invention is directed to the use of at least one compound of the invention to manufacture a medicament. The invention is also directed to compounds of the invention for use as a medicament or in the methods of treatment of the invention. In other words, the invention embraces a method for treating a disease related to unregulated c-kit transduction comprising administering an effective amount of at least one compound as defined above to a mammal in need of such treatment.

More particularly, the invention is aimed at a method for treating a disease selected from autoimmune diseases, allergic diseases, bone loss, cancers such as leukemia and GIST, tumor angiogenesis, inflammatory diseases, inflammatory bowel diseases (IBD), interstitial cystitis, mastocytosis, infections diseases, metabolic disorders, fibrosis, diabetes and CNS disorders comprising administering an effective amount of at least one compound depicted above to a mammal in need of such treatment.

The above described compounds are useful for manufacturing a medicament for the treatment of diseases related to unregulated c-kit transduction, including, but not limited to:

neoplastic diseases such as mastocytosis, canine mastocytoma, solid tumours, human gastrointestinal stromal tumor ("GIST"), small cell lung cancer, non-small cell lung cancer, acute myelocytic leukemia, acute lymphocytic leukemia, myelodysplastic syndrome, chronic myelogenous leukemia, colorectal carcinomas, gastric carcinomas, gastrointestinal stromal tumors, testicular cancers, glioblastomas, solid tumors and astrocytomas.

tumor angiogenesis.

metabolic diseases such as diabetes mellitus and its chronic complications; obesity; diabete type II; hyperlipidemias and dyslipidemias; atherosclerosis; hypertension; and cardiovascular disease.

allergic diseases such as asthma, allergic rhinitis, allergic sinusitis, anaphylactic syndrome, urticaria, angioedema, atopic dermatitis, allergic contact dermatitis, erythema nodosum, erythema multiforme, cutaneous necrotizing venulitis and insect bite skin inflammation and blood sucking parasitic infestation.

interstitial cystitis.

bone loss (osteoporosis).

inflammatory diseases such as rheumatoid arthritis, conjunctivitis, rheumatoid spondylitis, osteoarthritis, gouty arthritis and other arthritic conditions.

autoimmune diseases such as multiple sclerosis, psoriasis, intestine inflammatory disease, ulcerative colitis, Crohn's disease, rheumatoid arthritis and polyarthritis, local and systemic scleroderma, systemic lupus erythematosus, discoid lupus erythematosus, cutaneous lupus, dermatomyositis, polymyositis, Sjogren's syndrome, nodular panarteritis, autoimmune enteropathy, as well as proliferative glomerulonephritis.

graft-versus-host disease or graft rejection in any organ transplantation including kidney, pancreas, liver, heart, lung, and bone marrow.

other autoimmune diseases embraced by the invention active chronic hepatitis and chronic fatigue syndrome.

subepidermal blistering disorders such as pemphigus.

vasculitis.

melanocyte dysfunction associated diseases such as hypermelanosis resulting from melanocyte dysfunction and including lentigines, solar and senile lentigo, Dubreuilh melanosis, moles as well as malignant melanomas. In this regard, the invention embraces the use of the compounds defined above to manufacture a medicament or a cosmetic composition for whitening human skin.

CNS disorders such as psychiatric disorders, migraine, pain, memory loss and nerve cells degeneracy. More particularly, the method according to the invention is useful for the treatment of the following disorders: Depression including dysthymic disorder, cyclothymic disorder, bipolar depression, severe or "melancholic" depression, atypical depression, refractory depression, seasonal depression, anorexia, bulimia, premenstrual syndrome, post-menopause syndrome, other syndromes such as mental slowing and loss of concentration, pessimistic worry, agitation, self-deprecation, decreased libido, pain including, acute pain, postoperative pain, chronic pain, nociceptive pain, cancer pain, neuropathic pain, psychogenic pain syndromes, anxiety disorders including anxiety associated with hyperventilation and cardiac arrhythmias, phobic disorders, obsessive-compulsive disorder, posttraumatic stress disorder, acute stress disorder, generalized anxiety disorder, psychiatric emergencies such as panic attacks, including psychosis, delusional disorders, conversion disorders, phobias, mania, delirium, dissociative episodes including dissociative amnesia, dissociative fugue and dissociative identity disorder, depersonalization, catatonia, seizures, severe psychiatric emergencies including suicidal behaviour, self-neglect, violent or aggressive behaviour, trauma, borderline personality, and acute psychosis, schizophrenia including paranoid schizophrenia, disorganized schizophrenia, catatonic schizophrenia, and undifferentiated schizophrenia, neurodegenerative diseases including Alzheimer's disease, Parkinson's disease, Huntington's disease, the prion diseases, Motor Neurone Disease (MND), and Amyotrophic Lateral Sclerosis (ALS).

substance use disorders as referred herein include but are not limited to drug addiction, drug abuse, drug habituation, drug dependence, withdrawal syndrome and overdose.

cerebral ischemia.

fibrosis.

Duchenne muscular dystrophy.

Regarding mastocytosis, the invention contemplates the use of the compounds as defined above for treating the different categories which can be classified as follows:

Category I is composed by two sub-categories (IA and IB). Category IA is made by diseases in which mast cell infiltration is strictly localized to the skin. This category represents the most frequent form of the disease and includes: i) urticaria pigmentosa, the most common form of cutaneous mastocytosis, particularly encountered in children, ii) diffuse cutaneous mastocytosis, iii) solitary mastocytoma and iv) some rare subtypes like bullous, erythrodermic and teleangiectatic mastocytosis. These forms are characterized by their excellent prognosis with spontaneous remissions in children and a very indolent course in adults. Long term survival of this form of disease is generally comparable to that of the normal population and the translation into another form of mastocytosis is rare.

Category IB is represented by indolent systemic disease (SM) with or without cutaneous involvement. These forms are much more usual in adults than in children. The course of the disease is often indolent, but sometimes signs of aggressive or malignant mastocytosis can occur, leading to progressive impaired organ function.

Category II includes mastocytosis with an associated hematological disorder, such as a myeloproliferative or myelodysplastic syndrome, or acute leukemia. These malignant mastocytosis does not usually involve the skin. The progression of the disease depends generally on the type of associated hematological disorder that conditions the prognosis.

Category III is represented by aggressive systemic mastocytosis in which massive infiltration of multiple organs by abnormal mast cells is common. In patients who pursue this kind of aggressive clinical course, peripheral blood features suggestive of a myeloproliferative disorder are more prominent. The progression of the disease can be very rapid, similar to acute leukemia, or some patients can show a longer survival time.

Finally, category IV of mastocytosis includes the mast cell leukemia, characterized by the presence of circulating mast cells and mast cell progenitors representing more than 10% of the white blood cells. This entity represents probably the rarest type of leukemia in humans, and has a very poor prognosis, similar to the rapidly progressing variant of malignant mastocytosis. Mast cell leukemia can occur either de novo or as the terminal phase of urticaria pigmentosa or systemic mastocytosis.

The invention also contemplates the method as depicted for the treatment of recurrent bacterial infections, resurging infections after asymptomatic periods such as bacterial cystitis. More particularly, the invention can be practiced for treating FimH expressing bacteria infections such as Gram-negative enterobacteria including *E. coli, Klebsiella pneumoniae, Serratia marcescens, Citrobactor freudii* and *Salmonella typhimurium*.

In this method for treating bacterial infection, separate, sequential or concomitant administration of at least one antibiotic selected bacitracin, the cephalosporins, the penicillins, the aminoglycosides, the tetracyclines, the streptomycins and the macrolide antibiotics such as erythromycin; the fluoroquinolones, actinomycin, the sulfonamides and trimethoprim, is of interest.

In one preferred embodiment, the invention is directed to a method for treating neoplastic diseases such as mastocytosis, canine mastocytoma, solid tumours, human gastrointestinal stromal tumor ("GIST"), small cell lung cancer, non-small cell lung cancer, acute myelocytic leukemia, acute lymphocytic leukemia, myelodysplastic syndrome, chronic myelogenous leukemia, colorectal carcinomas, gastric carcinomas, gastrointestinal stromal tumors, testicular cancers, glioblastomas, and astrocytomas comprising administering a compound as defined herein to a human or mammal, especially dogs and cats, in need of such treatment.

In one other preferred embodiment, the invention is directed to a method for treating allergic diseases such as asthma, allergic rhinitis, allergic sinusitis, anaphylactic syndrome, urticaria, angioedema, atopic dermatitis, allergic contact dermatitis, erythema nodosum, erythema multiforme, cutaneous necrotizing venulitis and insect bite skin inflammation and blood sucking parasitic infestation comprising administering a compound as defined herein to a human or mammal, especially dogs and cats, in need of such treatment.

In still another preferred embodiment, the invention is directed to a method for treating inflammatory diseases such as rheumatoid arthritis, conjunctivitis, rheumatoid spondylitis, osteoarthritis, gouty arthritis and other arthritic conditions comprising administering a compound as defined herein to a human in need of such treatment.

In still another preferred embodiment, the invention is directed to a method for treating neurodegenerative diseases such as Alzheimer's disease, Parkinson's disease, Huntington's disease, Motor Neurone Disease (MND), and Amyotrophic Lateral Sclerosis (ALS).

In still another preferred embodiment, the invention is directed to a method for treating autoimmune diseases such as multiple sclerosis, psoriasis, intestine inflammatory disease, ulcerative colitis, Crohn's disease, rheumatoid arthritis and polyarthritis, local and systemic scleroderma, systemic lupus erythematosus, discoid lupus erythematosus, cutaneous lupus, dermatomyositis, polymyositis, Sjogren's syndrome, nodular panarteritis, autoimmune enteropathy, as well as proliferative glomerulonephritis comprising administering a compound as defined herein to a human in need of such treatment.

In still another preferred embodiment, the invention is directed to a method for treating graft-versus-host disease or graft rejection in any organ transplantation including kidney, pancreas, liver, heart, lung, and bone marrow comprising administering a compound as defined herein to a human in need of such treatment.

In yet a further embodiment, the compounds of the invention or pharmaceutically acceptable salts thereof can be administered in combination with one or more other active pharmaceutical agents in amounts sufficient to provide a therapeutic effect. In one implementation, the co-administration of the compounds of the invention and the other agent(s) is simultaneous. In another implementation, the co-administration of the compounds of the invention and the other agent(s) is sequential.

Examples of In Vitro TK Inhibition Assays
Procedures of C-Kit WT Inhibition Assays:
Proliferation Assays Colorimetric cell proliferation and viability assay (reagent CellTiter-Blue purchased from Promega cat N°G8081) was performed on BaF3 Kit WT cell line.

A total of $2.10^4$ cells/50 µl were seeded per well of a 96-wells plate. Treatment was initiated by addition of a 2× drug solution of ½ serial dilutions ranging from 0 to 10 µM. After incubating for 48 hours at 37° C., 10 µl of a ½ dilution of CellTiter-Blue reagent was added to each well and the plates were returned to the incubator for an additional 4 hours. The fluorescence intensity from the CellTiter-Blue reagent is proportional to the number of viable cells and data were recorded ($544_{Ex}/590_{Em}$) using a POLARstar OMEGA microplate reader (BMG LabteckSarl). A background control without cells was used as a blank. The positive control of the assay corresponds to the cell proliferation obtained in the absence of drug treatment (100% proliferation). Each sample was done in triplicate. The results were expressed as a percentage of the proliferation obtained in absence of treatment. All drugs were prepared as 20 mM stock solutions in DMSO and conserved at −80° C. Drug dilutions were made fresh in medium before each experiment. A DMSO control was included in each experiment.

Cells

The cell line expressing Human Kit WT was derived from the murine IL3-dependent Ba/F3 proB lymphoid cells. Ba/F3 Kit WT cells were maintained in RPMI medium containing 10% FCS and supplemented with 250 ng/ml of recombinant murine SCF.

EXPERIMENTAL RESULTS

The experimental results for various compounds according to the invention using the above-described protocols are set forth in Table 2:

TABLE 2 in vitro inhibitions of various compounds of the invention against c-kit WT

| Target | $IC_{50}$ (microM) | Compounds |
|---|---|---|
| c-kit WT | $IC_{50} \leq 1$ | 003, 005, 008, 010, 011, 020, 024, 025, 026, 028, 029, 030, 031, 032, 033, 034, 035, 041, 045, 047, 049, 050, 056, 057, 058, 061, 062, 069, 070, 071, 072, 073, 074, 075, 078, 079, 081, 082, 083, 084, 085, 086, 087, 089, 093, 094, 097, 100, 101, 102, 103, 104, 105, 106, 107, 108, 109, 110, 111, 112, 114, 115, 119, 120, 121, 124, 125, 126, 127, 128, 129, 130, 131, 132, 133, 136, 137, 138, 139, 140, 141, 142, 143, 144, 145, 146, 147, 148, 149, 150, 151, 152, 153, 154 |
| c-kit WT | $1 <$ $IC_{50} < 10$ | 001, 002, 004, 006, 007, 009, 012, 013, 014, 015, 016, 017, 018, 019, 021, 022, 023, 027, 036, 037, 038, 039, 040, 042, 043, 044, 046, 048, 051, 052, 053, 054, 055, 059, 060, 063, 064, 065, 066, 067, 068, 076, 077, 080, 088, 090, 091, 092, 095, 096, 098, 099, 113, 116, 117, 118, 122, 123, 134, 135 |

The inventors observed a very effective inhibition of a protein kinase and more particularly of native c-kit by the class of compounds of formula (I) of the invention. The listed compounds in Table 2 are well representing the class of compounds of formula (I).

The invention claimed is:
1. A compound of formula I:

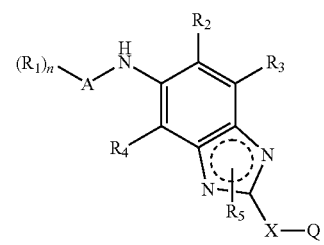

wherein:
A is a heteroaryl group selected from the group consisting of thiazolyl, oxazolyl, and pyrimidinyl;
n is 1 or 2;
each $R_1$ is independently selected from the group consisting of hydrogen, an aryl group, and a heteroaryl group, wherein the aryl group and heteroaryl group are unsubstituted or substituted by one or more substituents selected from the group consisting of a halogen, an aryl group, a heteroaryl group, a cyano, a —CONRR' group, and a —SO$_2$NRR' group, wherein R and R' are each independently selected from hydrogen and an alkyl group;
$R_2$, $R_3$ and $R_4$ are each independently selected from the group consisting of hydrogen, a $C_1$-$C_6$ alkyl group, and a $C_1$-$C_4$ haloalkyl group;
$R_5$ is selected from hydrogen and a $C_1$-$C_6$ alkyl group;
X is —(CH$_2$)$_n$— wherein n is 0, 1 or 2;
Q is selected from the group consisting of an aryl group, a heteroaryl group and a heterocycloalkyl group, wherein the aryl group, heteroaryl group and heterocycloalkyl group are unsubstituted or substituted by one or more substituents selected from the group consisting of a halogen, a halomethyl, a linear or branched $C_1$-$C_6$ alkyl group, a $C_1$-$C_4$ alkoxy group, an $C_1$-$C_4$ haloalkyl group, a $C_3$-$C_7$ cycloalkyl group, an aryl group, a heteroaryl group, a heterocycloalkyl group, a thioalkyl, a cyano, a haloalkoxy, a —C≡C—R, —NRR', —NR—CO—R', —CONRR', —SO₂R, —SO₂NRR', —NRSO₂R', —(CH₂)ₚ—NRR', —O—(CH₂)q—NRR', —(CH₂)ₚ—R", and —O—(CH₂)q—R" group, wherein R and R' are each independently selected from hydrogen and an alkyl group, R" is selected from a heteroaryl and a heterocycloalkyl group, p is 1 or 2, and q is 2 or 3.

2. The compound according to claim 1, wherein the compound is of formula II:

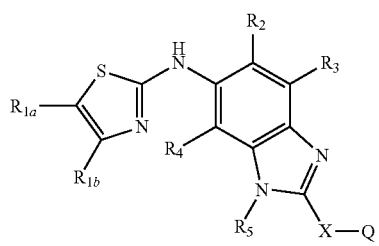

II wherein:

R₁ₐ is selected from the group consisting of a hydrogen, an aryl group and a heteroaryl group, wherein the aryl group and heteroaryl group are unsubstituted or substituted by one or more substituents selected from the group consisting of a halogen, an aryl group, a heteroaryl group, a cyano, —CONRR', and —SO₂NRR' group wherein R and R' are each independently selected from hydrogen and an alkyl group;

R₁ᵦ is selected from the group consisting of hydrogen, an aryl group and a heteroaryl group, wherein the aryl group and heteroaryl group are unsubstituted or substituted by one or more substituents selected from a halogen, an aryl group, a heteroaryl group, a cyano, —CONRR' and —SO₂NRR' group wherein R and R' are each independently selected from hydrogen and an alkyl group;

R₂, R₃ and R₄ are each independently selected from hydrogen, a C₁-C₆ alkyl group, and a C₁-C₄ haloalkyl group;

R₅ is selected from hydrogen and a C₁-C₆ alkyl group;

X is —(CH₂)ₙ— wherein n is 0, 1 or 2;

Q is selected from the group consisting of an aryl group, heteroaryl group and heterocycloalkyl group, wherein the aryl group, heteroaryl group and heterocycloalkyl group are unsubstituted or substituted by one or more substituents selected from an halogen, an halomethyl, a linear or branched C₁-C₆ alkyl group, a C₁-C₄ alkoxy group, an C₁-C₄ haloalkyl group, a C₃-C₇ cycloalkyl group, an aryl group, a heteroaryl group, a heterocycloalkyl group, a thioalkyl, a cyano, a haloalkoxy, a —C≡C—R, —NRR', —NR—CO—R', —CONRR', —SO₂R, —SO₂NRR', —NRSO₂R', —(CH₂)ₚ—NRR', —O—(CH₂)q—NRR', —(CH₂)ₚ—R", and —O—(CH₂)q—R" group; wherein R and R' are each independently selected from hydrogen and an alkyl group, R" is selected from a heteroaryl and a heterocycloalkyl group, p is 1 or 2, and q is 2 or 3.

3. The compound according to claim 1, wherein the compound is of formula III:

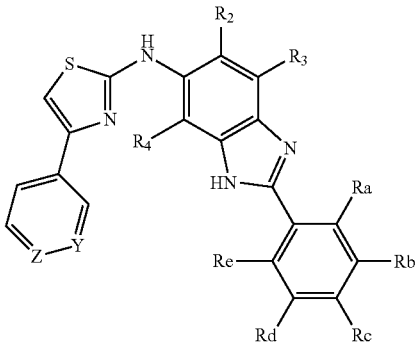

III wherein:

R₂, R₃ and R₄ are each independently selected from hydrogen, a C₁-C₆ alkyl group, and a C₁-C₄ haloalkyl group;

Z is selected from N and CR₇, wherein R₇ is selected from the group consisting of hydrogen, halogen, cyano, and a —CONRR' group wherein R and R' are each independently selected from hydrogen and a C₁-C₆ alkyl group;

Y is selected from N and CR₈, wherein R₈ is selected from the group consisting of hydrogen, halogen, cyano and a —CONRR' group wherein R and R' are each independently selected from hydrogen and a C₁-C₆ alkyl group;

Ra, Rb, Rc, Rd and Re are each independently selected from the group consisting of a hydrogen, a halogen, a halomethyl, a linear or branched C₁-C₆ alkyl group, a C₁-C₄ alkoxy group, a C₁-C₄ haloalkyl group, a C₃-C₇ cycloalkyl group, an aryl group, a heteroaryl group, a heterocycloalkyl group, a thioalkyl, a cyano, a haloalkoxy, a —C≡C—R, —NRR', —NR—CO—R', —CONRR', —SO₂NRR', —NRSO₂R', —(CH₂)ₚ—NRR', —O—(CH₂)q—NRR', —(CH₂)ₚ—R", and —O—(CH₂)q—R" group wherein R and R' are each independently selected from hydrogen and an alkyl group, R" is selected from a heteroaryl or a heterocycloalkyl group, p is 1 or 2, and q is 2 or 3.

4. The compound according to claim 1, wherein the compound is of formula IV:

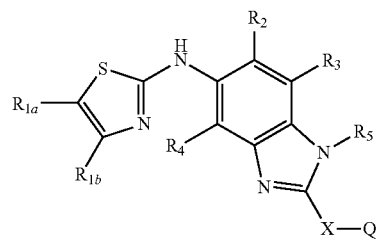

IV wherein:

R₁ₐ is selected from the group consisting of hydrogen, an aryl group, and a heteroaryl group, wherein the aryl group and heteroaryl group are unsubstituted or substituted by one or more substituents selected from the group consisting of a halogen, an aryl group, a heteroaryl group, a cyano, —CONRR', and —SO₂NRR' group wherein R and R' are each independently selected from hydrogen and an alkyl group;

$R_{1b}$ is selected from the group consisting of hydrogen, an aryl group and a heteroaryl group, wherein the aryl group and heteroaryl group are unsubstituted or substituted by one or more substituents selected from the group consisting of a halogen, an aryl group, a cyano, —CONRR', and —SO$_2$NRR', group wherein R and R' are each independently selected from hydrogen and an alkyl group;

$R_2$, $R_3$ and $R_4$ are independently selected from the group consisting of hydrogen, a $C_1$-$C_6$ alkyl group, and a $C_1$-$C_4$ haloalkyl group;

$R_5$ is selected from hydrogen and a $C_1$-$C_6$ alkyl group;

X is —(CH$_2$)$_n$— wherein n is 0, 1 or 2;

Q is selected from the group consisting of an aryl group, heteroaryl group, and heterocycloalkyl group, wherein the aryl group, heteroaryl group and heterocycloalkyl group are unsubstituted or substituted by one or more substituents selected from a halogen, a halomethyl, a linear or branched $C_1$-$C_6$ alkyl group, a $C_1$-$C_4$ alkoxy group, an $C_1$-$C_4$ haloalkyl group, a $C_3$-$C_7$ cycloalkyl group, an aryl group, a heteroaryl group, a heterocycloalkyl group, a thioalkyl, a cyano, a haloalkoxy, a —C≡C—R, —NRR', —NR—CO—R', —CONRR', SO$_2$R, —SO$_2$NRR', —NRSO$_2$R', —(CH$_2$)$_p$—NRR', —O—(CH$_2$)$_q$—NRR', —(CH$_2$)$_p$—R", and —O—(CH$_2$)$_q$—R" group wherein R and R' are each independently selected from hydrogen and an alkyl group, R" is selected from a heteroaryl and a heterocycloalkyl group, p is 1 or 2, and q is 2 or 3.

5. The compound according to claim 1, wherein the compound is of formula V:

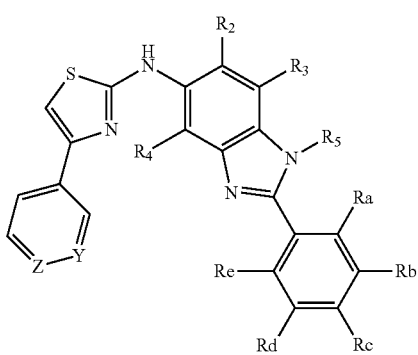

V wherein:

$R_2$, $R_3$ and $R_4$ are each independently selected from the group consisting of hydrogen, a $C_1$-$C_6$ alkyl group, and a $C_1$-$C_4$ haloalkyl group;

$R_5$ is selected from hydrogen and a $C_1$-$C_6$ alkyl group;

Z is selected from N and CR$_7$, wherein R$_7$ is selected from the group consisting of hydrogen, halogen, cyano, and a —CONRR' group wherein R and R' are each independently selected from hydrogen and a $C_1$-$C_6$ alkyl group;

Y is selected from N and CR$_8$, wherein R$_8$ is selected from the group consisting of hydrogen, halogen, cyano, —CONRR' group wherein R and R' are each independently selected from hydrogen and a $C_1$-$C_6$ alkyl group;

Ra, Rb, Rc, Rd and Re are each independently selected from the group consisting of a hydrogen, a halogen, a halomethyl, a linear or branched $C_1$-$C_6$ alkyl group, a $C_1$-$C_4$ alkoxy group, a $C_1$-$C_4$ haloalkyl group, a $C_3$-$C_7$ cycloalkyl group, an aryl group, a heteroaryl group, a heterocycloalkyl group, a thioalkyl, a cyano, a haloalkoxy, a —C≡C—R, —NRR', —NR—CO—R', —CONRR', —SO$_2$NRR', —NRSO$_2$R', —(CH$_2$)$_p$—NRR', —O—(CH$_2$)$_q$—NRR', —(CH$_2$)$_p$—R", and —O—(CH$_2$)$_q$—R" group wherein R and R' are each independently selected from hydrogen and an alkyl group, R" is selected from a heteroaryl and a heterocycloalkyl group, p is 1 or 2, and q is 2 or 3.

6. The compound according to claim 1, or a pharmaceutically acceptable salt thereof, selected from the group consisting of: (6-Methyl-2-o-tolyl-3H-benzoimidazol-5-yl)-(4-pyridin-3-yl-thiazol-2-yl)-amine; [2-(4-Methoxy-phenyl)-6-methyl-3H-benzoimidazol-5-yl]-(4-pyridin-3-yl-thiazol-2-yl)-amine; {6-Methyl-2-[4-(4-methyl-piperazin-1-ylmethyl)-phenyl]-3H-benzoimidazol-5-yl}-(4-pyridin-3-yl-thiazol-2-yl)-amine; (6-Methyl-2-p-tolyl-3H-benzoimidazol-5-yl)-(4-pyridin-3-yl-thiazol-2-yl)-amine; [6-Methyl-2-(3-trifluoromethyl-phenyl)-3H-benzoimidazol-5-yl]-(4-pyridin-3-yl-thiazol-2-yl)-amine; {6-Methyl-2-[4-(4-methyl-piperazin-1-ylmethyl)-phenyl]-3H-benzoimidazol-5-yl}-(5-pyridin-3-yl-oxazol-2-yl)-amine; [6-Methyl-2-(3-trifluoromethyl-phenyl)-3H-benzoimidazol-5-yl]-(5-pyridin-3-yl-oxazol-2-yl)-amine; [6-Methyl-2-(3-trifluoromethyl-phenyl)-3H-benzoimidazol-5-yl]-(4-pyridin-3-yl-pyrimidin-2-yl)-amine; {6-Methyl-2-[4-(4-methyl-piperazin-1-ylmethyl)-phenyl]-3H-benzoimidazol-5-yl}-(4-pyridin-3-yl-pyrimidin-2-yl)-amine; 3-[5-Methyl-6-(4-pyridin-3-yl-thiazol-2-ylamino)-1H-benzoimidazol-2-yl]-benzonitrile; (6-Methyl-2-m-tolyl-3H-benzoimidazol-5-yl)-(4-pyridin-3-yl-thiazol-2-yl)-amine; (6-Methyl-2-m-tolyl-3H-benzoimidazol-5-yl)-(4-pyridin-3-yl-pyrimidin-2-yl)-amine; 3-[5-Methyl-6-(4-pyridin-3-yl-pyrimidin-2-ylamino)-1H-benzoimidazol-2-yl]-benzonitrile; (6-Methyl-2-pyridin-3-yl-3H-benzoimidazol-5-yl)-(4-pyridin-3-yl-pyrimidin-2-yl)-amine; {6-Methyl-2-[3-(4-methyl-piperazin-1-yl)-phenyl]-3H-benzoimidazol-5-yl}-(4-pyridin-3-yl-pyrimidin-2-yl)-amine; {2-[3-(2-Dimethylamino-ethoxy)-phenyl]-6-methyl-3H-benzoimidazol-5-yl}-(4-pyridin-3-yl-pyrimidin-2-yl)-amine; (6-Methyl-2-quinolin-3-yl-3H-benzoimidazol-5-yl)-(4-pyridin-3-yl-pyrimidin-2-yl)-amine; [6-Methyl-2-(3-morpholin-4-ylmethyl-phenyl)-3H-benzoimidazol-5-yl]-(4-pyridin-3-yl-pyrimidin-2-yl)-amine; [2-(3-Fluoro-phenyl)-6-methyl-3H-benzoimidazol-5-yl]-(4-pyridin-3-yl-pyrimidin-2-yl)-amine; [6-Methyl-2-(3-morpholin-4-ylmethyl-5-trifluoromethyl-phenyl)-3H-benzoimidazol-5-yl]-(4-pyridin-3-yl-thiazol-2-yl)-amine; [6-Methyl-2-(4-trifluoromethyl-phenyl)-3H-benzoimidazol-5-yl]-(4-pyridin-3-yl-thiazol-2-yl)-amine; (2-Benzyl-6-methyl-3H-benzoimidazol-5-yl)-(4-pyridin-3-yl-thiazol-2-yl)-amine; [6-Methyl-2-(3-pyrrolidin-1-ylmethyl-5-trifluoromethyl-phenyl)-3H-benzoimidazol-5-yl]-(4-pyridin-3-yl-thiazol-2-yl)-amine; [6-Methyl-2-(3-piperidin-1-ylmethyl-5-trifluoromethyl-phenyl)-3H-benzoimidazol-5-yl]-(4-pyridin-3-yl-thiazol-2-yl)-amine; [2-(3-Difluoromethyl-phenyl)-6-methyl-3H-benzoimidazol-5-yl]-(4-pyridin-3-yl-thiazol-2-yl)-amine; [6-Methyl-2-(3-trifluoromethoxy-phenyl)-3H-benzoimidazol-5-yl]-(4-pyridin-3-yl-thiazol-2-yl)-amine; [6-Methyl-2-(4-trifluoromethyl-phenyl)-3H-benzoimidazol-5-yl]-(4-pyridin-3-yl-pyrimidin-2-yl)-amine; [6-Methyl-2-(3-morpholin-4-ylmethyl-5-trifluoromethyl-phenyl)-3H-benzoimidazol-5-yl]-(4-pyridin-3-yl-pyrimidin-2-yl)-amine; [6-Methyl-2-(3-pyrrolidin-1-ylmethyl-5-trifluoromethyl-phenyl)-3H-benzoimidazol-5-yl]-(4- pyridin-3-yl-pyrimidin-2-yl)-amine; [2-(3-Difluoromethyl-phenyl)-6-methyl-3H-benzoimidazol-5-yl]-(4-pyridin-3-yl-pyrimidin-2-yl)-amine; [2-(3-Chloro-phenyl)-6-methyl-3H-benzoimidazol-5-yl]-(4-pyridin-3-yl-pyrimidin-2-yl)-amine; [2-(3-Chloro-phenyl)-6-methyl-3H-benzoimidazol-5-yl]-(4-pyridin-3-yl-thiazol-2-yl)-amine; [6-Methyl-2-(3-trifluoromethyl-phenyl)-3H-benzoimidazol-5-yl]-(4-pyridin-4-yl-thiazol-2-yl)-amine; (6-Methyl-2-m-tolyl-3H-benzoimidazol-5-yl)-(4-pyridin-4-yl-thiazol-2-yl)-amine; [6-Methyl-2-(3-piperidin-1-ylmethyl-5-trifluoromethyl-phenyl)-3H-benzoimidazol-5-yl]-(4-pyridin-3-yl-pyrimidin-2-yl)-amine; {2-[5-tert-Butyl-2-(2-dimethylamino-ethoxy)-phenyl]-6-methyl-3H-benzoimidazol-5-yl}-(4-pyridin-3-yl-pyrimidin-2-yl)-amine; [6-Methyl-2-(3-trifluoromethoxy-phenyl)-3H-benzoimidazol-5-yl]-(4-pyridin-3-yl-pyrimidin-2-yl)-amine; [2-(3-Methanesulfonyl-phenyl)-6-methyl-3H-benzoimidazol-5-yl]-(4-pyridin-3-yl-pyrimidin-2-yl)-amine; {6-Methyl-2-[3-(4-methyl-piperazin-1-ylmethyl)-5-oxazol-5-yl-phenyl]-3H-benzoimidazol-5-yl}-(4-pyridin-3-yl-pyrimidin-2-yl)-amine; {6-Methyl-2-[3-(4-methyl-piperazin-1-ylmethyl)-5-trifluoromethyl-phenyl]-3H-benzoimidazol-5-yl}-(4-pyridin-3-yl-pyrimidin-2-yl)-amine; [6-Methyl-2-(4-methyl-3-trifluoromethyl-phenyl)-3H-benzoimidazol-5-yl]-(4-pyridin-3-yl-pyrimidin-2-yl)-amine; [6-Methyl-2-(5-trifluoromethyl-pyridin-3-yl)-3H-benzoimidazol-5-yl]-(4-pyridin-3-yl-pyrimidin-2-yl)-amine; {6-Methyl-2-[3-(4-methyl-piperazin-1-ylmethyl)-phenyl]-3H-benzoimidazol-5-yl}-(4-pyridin-3-yl-pyrimidin-2-yl)-amine; {6-Methyl-2-[3-(4-methyl-piperazin-1-ylmethyl)-phenyl]-1H-benzoimidazol-5-yl}-(4-pyridin-3-yl-thiazol-2-yl)-amine; [2-(3-Difluoromethyl-phenyl)-6-methyl-3H-benzoimidazol-5-yl]-(4-pyridin-4-yl-thiazol-2-yl)-amine; {6-Methyl-2-[3-(4-methyl-piperazin-1-ylmethyl)-phenyl]-1H-benzoimidazol-5-yl}-(4-pyridin-4-yl-thiazol-2-yl)-amine; [6-Methyl-2-(3-trifluoromethoxy-phenyl)-3H-benzoimidazol-5-yl]-(4-pyridin-4-yl-thiazol-2-yl)-amine; {6-Methyl-2-[4-(4-methyl-piperazin-1-ylmethyl)-phenyl]-1H-benzoimidazol-5-yl}-(4-pyridin-4-yl-thiazol-2-yl)-amine; [6-Methyl-2-(5-trifluoromethyl-pyridin-3-yl)-3H-benzoimidazol-5-yl]-(4-pyridin-3-yl-thiazol-2-yl)-amine; [6-Methyl-2-(4-trifluoromethyl-phenyl)-3H-benzoimidazol-5-yl]-(4-pyridin-4-yl-thiazol-2-yl)-amine; [6-Methyl-2-(3-trifluoromethyl-benzyl)-3H-benzoimidazol-5-yl]-(5-pyridin-4-yl-oxazol-2-yl)-amine; [2-(3-Fluoro-benzyl)-6-methyl-3H-benzoimidazol-5-yl]-(5-pyridin-4-yl-oxazol-2-yl)-amine; [6-Methyl-2-(3-trifluoromethyl-phenyl)-3H-benzoimidazol-5-yl]-(5-pyridin-4-yl-oxazol-2-yl)-amine; [6-Methyl-2-(4-trifluoromethyl-benzyl)-3H-benzoimidazol-5-yl]-(5-pyridin-4-yl-oxazol-2-yl)-amine; (6-Methyl-2-morpholin-4-ylmethyl-3H-benzoimidazol-5-yl)-(5-pyridin-4-yl-oxazol-2-yl)-amine; [6-Methyl-2-(4-methyl-3-trifluoromethyl-phenyl)-3H-benzoimidazol-5-yl]-(4-pyridin-3-yl-thiazol-2-yl)-amine; [6-Methyl-2-(4-pyrazol-1-yl-phenyl)-3H-benzoimidazol-5-yl]-(4-pyridin-3-yl-thiazol-2-yl)-amine; [2-(3-Fluoro-5-trifluoromethyl-phenyl)-6-methyl-3H-benzoimidazol-5-yl]-(4-pyridin-3-yl-thiazol-2-yl)-amine; [2-(4-Chloro-phenyl)-6-methyl-1H-benzoimidazol-5-yl]-(4-pyridin-3-yl-thiazol-2-yl)-amine; [2-(4-Fluoro-phenyl)-6-methyl-1H-benzoimidazol-5-yl]-(4-pyridin-3-yl-thiazol-2-yl)-amine; [2-(3-Difluoromethyl-phenyl)-6-methyl-3H-benzoimidazol-5-yl]-(4-pyrimidin-5-yl-thiazol-2-yl)-amine; [6-Methyl-2-(3-trifluoromethyl-phenyl)-3H-benzoimidazol-5-yl]-(4-pyrimidin-5-yl-thiazol-2-yl)-amine; [6-Methyl-2-(3-trifluoromethoxy-phenyl)-3H-benzoimidazol-5-yl]-(4-pyrimidin-5-yl-thiazol-2-yl)-amine; (6-Methyl-2-morpholin-4-ylmethyl-3H-benzoimidazol-5-yl)-(4-pyridin-3-yl-thiazol-2-yl)-amine; {6-Methyl-2-[4-(4-methyl-piperazin-1-ylmethyl)-phenyl]-3H-benzoimidazol-5-yl}-(4-pyrimidin-5-yl-thiazol-2-yl)-amine; (6-Methyl-2-m-tolyl-1H-benzoimidazol-5-yl)-(4-pyrimidin-5-yl-thiazol-2-yl)-amine; [6-Methyl-2-(4-trifluoromethyl-phenyl)-1H-benzoimidazol-5-yl]-(4-pyrimidin-5-yl-thiazol-2-yl)-amine; [2-(3-Chloro-phenyl)-6-methyl-1H-benzoimidazol-5-yl]-(4-pyrimidin-5-yl-thiazol-2-yl)-amine; 4-{2-[2-(3-Difluoromethyl-phenyl)-6-methyl-3H-benzoimidazol-5-ylamino]-thiazol-4-yl}-benzonitrile; 4-{2-[6-Methyl-2-(3-trifluoromethyl-phenyl)-3H-benzoimidazol-5-ylamino]-thiazol-4-yl}-benzonitrile; 4-{2-[2-(3-Difluoromethyl-phenyl)-6-methyl-3H-benzoimidazol-5-ylamino]-thiazol-4-yl}-benzamide; 4-{2-[6-Methyl-2-(4-trifluoromethyl-phenyl)-3H-benzoimidazol-5-ylamino]-thiazol-4-yl}-benzamide; 4-{2-[6-Methyl-2-(3-trifluoromethoxy-phenyl)-3H-benzoimidazol-5-ylamino]-thiazol-4-yl}-benzamide; 4-[2-(6-Methyl-2-m-tolyl-3H-benzoimidazol-5-ylamino)-thiazol-4-yl]-benzonitrile; 4-{2-[6-Methyl-2-(3-trifluoromethoxy-phenyl)-3H-benzoimidazol-5-ylamino]-thiazol-4-yl}-benzonitrile; 4-{2-[6-Methyl-2-(4-trifluoromethyl-phenyl)-3H-benzoimidazol-5-ylamino]-thiazol-4-yl}-benzonitrile; [6-Methyl-2-(3-methyl-3H-imidazol-4-yl)-3H-benzoimidazol-5-yl]-(4-pyridin-3-yl-thiazol-2-yl)-amine; [6-Methyl-2-(5-methyl-thiophen-2-yl)-3H-benzoimidazol-5-yl]-(4-pyridin-3-yl-thiazol-2-yl)-amine; [6-Methyl-2-(5-methyl-thiophen-2-yl)-1H-benzoimidazol-5-yl]-(4-pyridin-4-yl-thiazol-2-yl)-amine; [6-Methyl-2-(3-methyl-3H-imidazol-4-yl)-1H-benzoimidazol-5-yl]-(4-pyridin-4-yl-thiazol-2-yl)-amine; [2-(3-Difluoromethyl-phenyl)-1,6-dimethyl-1H-benzoimidazol-5-yl]-(4-pyridin-4-yl-thiazol-2-yl)-amine; [1,6-Dimethyl-2-(3-trifluoromethyl-phenyl)-1H-benzoimidazol-5-yl]-(4-pyridin-4-yl-thiazol-2-yl)-amine; [1,6-Dimethyl-2-(3-trifluoromethoxy-phenyl)-1H-benzoimidazol-5-yl]-(4-pyridin-4-yl-thiazol-2-yl)-amine; [2-(3-Difluoromethyl-phenyl)-1,6-dimethyl-1H-benzoimidazol-5-yl]-(4-pyridin-3-yl-thiazol-2-yl)-amine; [1,6-Dimethyl-2-(3-trifluoromethyl-phenyl)-1H-benzoimidazol-5-yl]-(4-pyridin-3-yl-thiazol-2-yl)-amine; [1,6-Dimethyl-2-(3-trifluoromethoxy-phenyl)-1H-benzoimidazol-5-yl]-(4-pyridin-3-yl-thiazol-2-yl)-amine; [2-(3-Difluoromethyl-phenyl)-1H-benzoimidazol-5-yl]-(4-pyridin-3-yl-thiazol-2-yl)-amine; (4-Pyridin-3-yl-thiazol-2-yl)-[2-(3-trifluoromethyl-phenyl)-1H-benzoimidazol-5-yl]-amine; (4-Pyridin-3-yl-thiazol-2-yl)-[2-(3-trifluoromethoxy-phenyl)-1H-benzoimidazol-5-yl]-amine; [2-(3-Difluoromethyl-phenyl)-1-methyl-1H-benzoimidazol-5-yl]-(4-pyridin-3-yl-thiazol-2-yl)-amine; [1-Methyl-2-(3-trifluoromethyl-phenyl)-1H-benzoimidazol-5-yl]-(4-pyridin-3-yl-thiazol-2-yl)-amine; [1-Methyl-2-(3-trifluoromethoxy-phenyl)-1H-benzoimidazol-5-yl]-(4-pyridin-3-yl-thiazol-2-yl)-amine; [2-(4-Difluoromethyl-phenyl)-1,6-dimethyl-1H-benzoimidazol-5-yl]-(4-pyridin-3-yl-thiazol-2-yl)-amine; [2-(4-Difluoromethyl-phenyl)-1,6-dimethyl-1H-benzoimidazol-5-yl]-(4-pyridin-4-yl-thiazol-2-yl)-amine; {1,6-Dimethyl-2-[3-(4-methyl-piperazin-1-yl)-phenyl]-1H-benzoimidazol-5-yl}-(4-pyridin-3-yl-thiazol-2-yl)-amine; {1,6-Dimethyl-2-[3-(4-methyl-piperazin-1-yl)-phenyl]-1H-benzoimidazol-5-yl}-(4-pyridin-4-yl-thiazol-2-yl)-amine; [2-(4-Difluoromethyl-phenyl)-6-methyl-1H-benzoimidazol-5-yl]-(4-pyridin-3-yl-thiazol-2-yl)-amine; {1,6-Dimethyl-2-[4-(4-methyl-piperazin-1-ylmethyl)-phenyl]-1H-benzoimidazol-5-yl}-(4-pyridin-3-yl-thiazol-2-yl)-amine; {1,6-Dimethyl-2-[4-(4-methyl-piperazin-1-ylmethyl)-phenyl]-1H-benzoimidazol-5-yl}-(4-pyridin-4-yl-thiazol-2-yl)-amine; [2-(3-Difluoromethyl-phenyl)-1-isopropyl-6-methyl-1H-benzoimidazol-5-yl]-(4-pyridin-4-yl-thiazol-2-yl)-amine;

[1-Isopropyl-6-methyl-2-(3-trifluoromethyl-phenyl)-1H-benzoimidazol-5-yl]-(4-pyridin-4-yl-thiazol-2-yl)-amine; (1-Isopropyl-6-methyl-2-m-tolyl-1H-benzoimidazol-5-yl)-(4-pyridin-4-yl-thiazol-2-yl)-amine; [2-(3-Difluoromethyl-phenyl)-1-ethyl-6-methyl-1H-benzoimidazol-5-yl]-(4-pyridin-4-yl-thiazol-2-yl)-amine; (1-Ethyl-6-methyl-2-m-tolyl-1H-benzoimidazol-5-yl)-(4-pyridin-4-yl-thiazol-2-yl)-amine; [1-Ethyl-6-methyl-2-(3-trifluoromethyl-phenyl)-1H-benzoimidazol-5-yl]-(4-pyridin-4-yl-thiazol-2-yl)-amine; [4-(2-Chloro-pyridin-4-yl)-thiazol-2-yl]-[6-methyl-2-(3-trifluoromethyl-phenyl)-1H-benzoimidazol-5-yl]-amine; [4-(2-Chloro-pyridin-4-yl)-thiazol-2-yl]-(6-methyl-2-m-tolyl-1H-benzoimidazol-5-yl)-amine; [4-(2-Chloro-pyridin-4-yl)-thiazol-2-yl]-[2-(3-difluoromethyl-phenyl)-6-methyl-1H-benzoimidazol-5-yl]-amine; [2-(3-Difluoromethyl-phenyl)-1-ethyl-6-methyl-1H-benzoimidazol-5-yl]-(4-pyridin-3-yl-thiazol-2-yl)-amine; [1-Ethyl-6-methyl-2-(3-trifluoromethyl-phenyl)-1H-benzoimidazol-5-yl]-(4-pyridin-3-yl-thiazol-2-yl)-amine; 4-{2-[2-(3-Difluoromethyl-phenyl)-1,6-dimethyl-1H-benzoimidazol-5-ylamino]-thiazol-4-yl}-benzonitrile; 4-[2-(1,6-Dimethyl-2-m-tolyl-1H-benzoimidazol-5-ylamino)-thiazol-4-yl]-benzonitrile; [2-(3-Difluoromethyl-phenyl)-3,6-dimethyl-3H-benzoimidazol-5-yl]-(4-pyridin-3-yl-thiazol-2-yl)-amine; 4-{2-[1,6-Dimethyl-2-(3-trifluoromethyl-phenyl)-1H-benzoimidazol-5-ylamino]-thiazol-4-yl}-benzonitrile; [1-Ethyl-6-methyl-2-(3-trifluoromethoxy-phenyl)-1H-benzoimidazol-5-yl]-(4-pyridin-3-yl-thiazol-2-yl)-amine; [3,6-Dimethyl-2-(3-trifluoromethyl-phenyl)-3H-benzoimidazol-5-yl]-(4-pyridin-3-yl-thiazol-2-yl)-amine; [3,6-Dimethyl-2-(3-trifluoromethoxy-phenyl)-3H-benzoimidazol-5-yl]-(4-pyridin-3-yl-thiazol-2-yl)-amine; (3,6-Dimethyl-2-m-tolyl-3H-benzoimidazol-5-yl)-(4-pyridin-3-yl-thiazol-2-yl)-amine; [4-(2-Chloro-pyridin-4-yl)-thiazol-2-yl]-[2-(3-difluoromethyl-phenyl)-1,6-dimethyl-1H-benzoimidazol-5-yl]-amine; [2-(3-Methanesulfonyl-phenyl)-1,6-dimethyl-1H-benzoimidazol-5-yl]-(4-pyridin-4-yl-thiazol-2-yl)-amine; [2-(3-Methanesulfonyl-phenyl)-6-methyl-1H-benzoimidazol-5-yl]-(4-pyridin-3-yl-thiazol-2-yl)-amine; Ethenesulfonic acid {3-[1,6-dimethyl-5-(4-pyridin-4-yl-thiazol-2-ylamino)-1H-benzoimidazol-2-yl]-5-trifluoromethyl-phenyl}-amide; [2-(3-Fluoro-phenyl)-6-methyl-1H-benzoimidazol-5-yl]-(4-pyridin-3-yl-thiazol-2-yl)-amine; [2-(3-Fluoro-phenyl)-1,6-dimethyl-1H-benzoimidazol-5-yl]-(4-pyridin-4-yl-thiazol-2-yl)-amine; [2-(3-Methoxy-phenyl)-1,6-dimethyl-1H-benzoimidazol-5-yl]-(4-pyridin-4-yl-thiazol-2-yl)-amine; [2-(3-Methoxy-phenyl)-6-methyl-1H-benzoimidazol-5-yl]-(4-pyridin-3-yl-thiazol-2-yl)-amine; 3-{2-[2-(3-Difluoromethyl-phenyl)-6-methyl-3H-benzoimidazol-5-ylamino]-thiazol-4-yl}-benzonitrile; 4-{2-[2-(3-Methoxy-phenyl)-6-methyl-1H-benzoimidazol-5-ylamino]-thiazol-4-yl}-benzonitrile; 3-[2-(6-Methyl-2-m-tolyl-1H-benzoimidazol-5-ylamino)-thiazol-4-yl]-benzonitrile; 3-{2-[6-Methyl-2-(3-trifluoromethyl-phenyl)-1H-benzoimidazol-5-ylamino]-thiazol-4-yl}-benzonitrile; 4-{2-[2-(3-Methanesulfonyl-phenyl)-6-methyl-1H-benzoimidazol-5-ylamino]-thiazol-4-yl}-benzonitrile; [2-(3-Dimethylamino-phenyl)-6-methyl-3H-benzoimidazol-5-yl]-(4-pyridin-3-yl-thiazol-2-yl)-amine; [2-(3-Dimethylamino-phenyl)-1,6-dimethyl-1H-benzoimidazol-5-yl]-(4-pyridin-4-yl-thiazol-2-yl)-amine; Ethanesulfonic acid {3-[1,6-dimethyl-5-(4-pyridin-4-yl-thiazol-2-ylamino)-1H-benzoimidazol-2-yl]-phenyl}-amide; Ethenesulfonic acid {3-[1,6-dimethyl-5-(4-pyridin-4-yl-thiazol-2-ylamino)-1H-benzoimidazol-2-yl]-phenyl}-amide; [2-(3-Isopropyl-phenyl)-6-methyl-1H-benzoimidazol-5-yl]-(4-pyridin-3-yl-thiazol-2-yl)-amine; [2-(3-tert-Butyl-phenyl)-6-methyl-1H-benzoimidazol-5-yl]-(4-pyridin-3-yl-thiazol-2-yl)-amine; 4-{2-[2-(3-Fluoro-5-trifluoromethyl-phenyl)-1,6-dimethyl-1H-benzoimidazol-5-ylamino]-thiazol-4-yl}-benzonitrile; [2-(3-Ethynyl-phenyl)-6-methyl-1H-benzoimidazol-5-yl]-(4-pyridin-3-yl-thiazol-2-yl)-amine; [2-(3-Isopropyl-phenyl)-1,6-dimethyl-1H-benzoimidazol-5-yl]-(4-pyridin-3-yl-thiazol-2-yl)-amine; 4-{2-[2-(3-Ethynyl-phenyl)-6-methyl-1H-benzoimidazol-5-ylamino]-thiazol-4-yl}-benzonitrile; 4-{2-[2-(3-Isopropyl-phenyl)-1,6-dimethyl-1H-benzoimidazol-5-ylamino]-thiazol-4-yl}-benzonitrile; 4-{2-[2-(3-Isopropyl-phenyl)-6-methyl-1H-benzoimidazol-5-ylamino]-thiazol-4-yl}-benzonitrile; 4-{2-[2-(3-tert-Butyl-phenyl)-1,6-dimethyl-1H-benzoimidazol-5-ylamino]-thiazol-4-yl}-benzonitrile; [2-(3-tert-Butyl-phenyl)-1,6-dimethyl-1H-benzoimidazol-5-yl]-(4-pyridin-3-yl-thiazol-2-yl)-amine; [2-(3-Ethynyl-phenyl)-1,6-dimethyl-1H-benzoimidazol-5-yl]-(4-pyridin-3-yl-thiazol-2-yl)-amine; [2-(3-Fluoro-5-trifluoromethyl-phenyl)-1,6-dimethyl-1H-benzoimidazol-5-yl]-(4-pyridin-4-yl-thiazol-2-yl)-amine; [2-(3-Fluoro-5-trifluoromethyl-phenyl)-1,6-dimethyl-1H-benzoimidazol-5-yl]-(4-pyridin-3-yl-thiazol-2-yl)-amine; [2-(3-Fluoro-5-trifluoromethyl-phenyl)-6-methyl-1H-benzoimidazol-5-yl]-(4-pyridin-4-yl-thiazol-2-yl)-amine; [2-(3-Isopropyl-phenyl)-6-methyl-1H-benzoimidazol-5-yl]-(4-pyridin-4-yl-thiazol-2-yl)-amine; [2-(3-Isopropyl-phenyl)-1,6-dimethyl-1H-benzoimidazol-5-yl]-(4-pyridin-4-yl-thiazol-2-yl)-amine; [2-(3-tert-Butyl-phenyl)-1,6-dimethyl-1H-benzoimidazol-5-yl]-(4-pyridin-4-yl-thiazol-2-yl)-amine; [2-(3-tert-Butyl-phenyl)-6-methyl-1H-benzoimidazol-5-yl]-(4-pyridin-4-yl-thiazol-2-yl)-amine; and 4-{2-[2-(3-tert-Butyl-phenyl)-6-methyl-1H-benzoimidazol-5-ylamino]-thiazol-4-yl}-benzonitrile.

7. A pharmaceutical composition comprising a compound according to claim 1 or a pharmaceutically acceptable salt thereof.

8. A cosmetic composition comprising a compound according to claim 1 or a pharmaceutically acceptable salt thereof.

* * * * *